(12) United States Patent
Schally et al.

(10) Patent No.: US 10,555,987 B2
(45) Date of Patent: *Feb. 11, 2020

(54) GHRH AGONISTS FOR THE TREATMENT OF ISCHEMIC DISORDERS

(71) Applicants: UNIVERSITY OF MIAMI, Miami, FL (US); U.S.A., REPRESENTED BY THE DEPARTMENT OF VETERANS AFFAIRS, Washington, DC (US)

(72) Inventors: Andrew Schally, Miami Beach, FL (US); Joshua M. Hare, Miami Beach, FL (US); Norman Block, Hollywood, FL (US); Samirah Gomes, Miami Beach, FL (US); Rosemeire M. Kanashiro-Takeuchi, Miami, FL (US)

(73) Assignees: UNIVERSITY OF MIAMI, Miami, FL (US); U.S.A., REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,079

(22) Filed: Nov. 21, 2017

(65) Prior Publication Data

US 2018/0250358 A1 Sep. 6, 2018

Related U.S. Application Data

(62) Division of application No. 14/138,391, filed on Dec. 23, 2013, now Pat. No. 9,855,312.

(60) Provisional application No. 61/892,963, filed on Oct. 18, 2013, provisional application No. 61/745,051, filed on Dec. 21, 2012.

(51) Int. Cl.
| | | |
|---|---|---|
| A61K 38/25 | (2006.01) | |
| C07K 14/60 | (2006.01) | |
| A61K 38/16 | (2006.01) | |

(52) U.S. Cl.
CPC .................................. *A61K 38/16* (2013.01)

(58) Field of Classification Search
None
See application file for complete search history.

(56) References Cited

U.S. PATENT DOCUMENTS

| | | | |
|---|---|---|---|
| 4,622,312 A | 11/1986 | Felix et al. | |
| 4,649,131 A | 3/1987 | Felix et al. | |
| 4,659,693 A | 4/1987 | Nestor | |
| 4,689,318 A | 8/1987 | Kaiser et al. | |
| 4,784,987 A | 11/1988 | Rivier et al. | |
| 4,914,189 A | 4/1990 | Schally et al. | |
| 5,023,322 A | 6/1991 | Kovacs et al. | |
| 5,262,519 A | 11/1993 | Rivier et al. | |
| 5,756,458 A | 5/1998 | Kubiak et al. | |
| 5,792,747 A | 8/1998 | Schally et al. | |
| 5,846,936 A | 12/1998 | Felix et al. | |
| 6,458,764 B1 | 10/2002 | Gravel et al. | |
| 7,241,744 B2 | 7/2007 | Draghia-Akli et al. | |
| 7,268,113 B2 | 9/2007 | Bridon et al. | |
| 7,928,063 B2 | 4/2011 | Izdebski et al. | |
| 8,507,333 B2 | 8/2013 | Bryant et al. | |
| 8,507,433 B1 | 8/2013 | Schally et al. | |
| 9,079,974 B2 * | 7/2015 | Schally .................. C07K 14/60 |
| 2005/0261201 A1 | 11/2005 | Polvino et al. | |
| 2007/0042950 A1 | 2/2007 | Schally et al. | |
| 2008/0312157 A1 | 12/2008 | Levy et al. | |
| 2009/0023646 A1 | 1/2009 | Gaudreau | |
| 2010/0092539 A1 | 4/2010 | Schally et al. | |
| 2011/0066230 A1* | 3/2011 | Schally ................ A61K 9/0019 623/1.46 |
| 2013/0195807 A1 | 8/2013 | Schally et al. | |
| 2013/0261058 A1 | 10/2013 | Schally et al. | |
| 2014/0057847 A1 | 2/2014 | Schally et al. | |

(Continued)

FOREIGN PATENT DOCUMENTS

| | | |
|---|---|---|
| CN | 1328570 A | 12/2001 |
| CN | 1871020 A | 11/2006 |
| EP | 0413839 A1 | 2/1991 |

(Continued)

OTHER PUBLICATIONS

Izdebski et al. "Synthesis and biological evaluation of superactive agonists of growth hormone-releasing hormone" Proc. Natl. Acad. Sci. 92:4872-4876. (Year: 1995).*

(Continued)

*Primary Examiner* — Christina Bradley
*Assistant Examiner* — Zachary J Miknis
(74) *Attorney, Agent, or Firm* — Marshall, Gerstein & Borun LLP

(57) ABSTRACT

Disclosed herein are compositions of GHRH agonists and peptides, and methods to treat disorders, such as ischemia and reperfusion injury. In one embodiment, a method of treating a reperfusion injury in a subject in need may involve administering a therapeutically effective amount of at least one GHRH agonist peptide to the subject. In additional embodiment, a method of promoting vasculogenesis in a mammal may involve administering a therapeutically effective amount of at least one GHRH agonist peptide to the subject. In a further embodiment, a method of promoting differentiation of mesenchymal stem cells into endothelial cells may involve contacting mesenchymal stem cells with at least one GHRH agonist peptide.

1 Claim, 53 Drawing Sheets
Specification includes a Sequence Listing.

(56) References Cited

U.S. PATENT DOCUMENTS

| | | | |
|---|---|---|---|
| 2014/0058068 A1* | 2/2014 | Schally | C07K 14/60 530/399 |
| 2014/0193378 A1 | 7/2014 | Schally et al. | |

FOREIGN PATENT DOCUMENTS

| | | |
|---|---|---|
| WO | WO-9012810 A1 | 11/1990 |
| WO | WO-94/11396 A1 | 5/1994 |
| WO | WO-9622782 A1 | 8/1996 |
| WO | WO-9742223 A1 | 11/1997 |
| WO | WO-03037928 A2 | 5/2003 |
| WO | WO-2009/009727 A2 | 1/2009 |
| WO | WO-2011034976 A1 | 3/2011 |
| WO | WO-2011153491 A2 | 12/2011 |
| WO | WO-2012/037519 A2 | 3/2012 |
| WO | WO-2013095903 A1 | 6/2013 |

OTHER PUBLICATIONS

Soule et al. "Incorporation of D-Ala2 in Growth Hormone-Releasing Hormone-(1-29)-NH2 Increases the Half-life and Decreases Metabolic Clearance in Normal Men" J. Clin. Endocrinol. Metab. 79:1208-1211 (Year: 1994).*

Kanashiro-Takeuchi et al. "Activation of growth hormone releasing hormone (GHRH) receptor stimulates cardiac reverse remodeling after myocardial infarction (MI)" Proc. Natl. Acad. Sci. 109:559-563 (Year: 2012).*

Siejka et al. "Antineoplastic Action of Growth Hormone-Releasing Hormone (GHRH) Agonists" Recent Patents on Anti-Cancer Drug Discovery 7:56-63. (Year: 2012).*

Aimaretti, et al. "GHRH and GH Secretagogues: Clinical Perspectives and Safety", Pediatr Endocrine/ Rev 2, (Nov. 2004) 2(1):86-92.

Anonymous "Ischemia" accessed on Feb. 9, 2015 at en.wikipedia.org/wiki/Ischemia. Published Jun. 29, 2004.

Anonymous. "Myocardial Infarction (Heart Attack)" http://www.hopkinsmedicine.org/heart_vascular_institute/conditions_treatments/conditions/myocardial_infarction.htm. Published Mar. 12, 2009.

Armann et al., "Quantification of basal and stimulated ROS levels as predictors of islet potency and function," Am J Transplant, (2007), 7:38-47.

Bajusz et al. in Peptides, 1982, Blaha and Melon, Eds. de Gruyter, Berlin-N.Y., 1983, pp. 643-647.

Bollano, et al. "Growth hormone alone or combined with metoprolol preserves cardiac function after myocardial infarction in rats", Eur J Heart Fail, (2001) 3:651-660.

Bonner-Weir, "In vitro cultivation of human islets from expanded ductal tissue," Proc Natl Acad Sci USA, (Jul. 5, 2000), 97(14):7999-8004.

Bork, "Powers and Pitfalls in Sequence Analysis: The 70% Hurdle", Genome Research, (2000), 10:398-400.

Brenner, "Errors in genome annotation", Trends in Genetics, (Apr. 1999), 15(4):132-133.

Broglio et al., Patients with dilated cardiomyopathy show reduction of the somatotroph responsiveness to GHRH both alone and combined with arginine, European Journal of Endocrinology (2000), 142:157-163.

Cai et al., "Synthesis of new potent agonistic analogs of growth hormone-releasing hormone (GHRH) and evaluation of their endocrine and cardiac activities," Peptides (Feb. 2014), 52:104-112. Epub: Dec. 25, 2013.

Campbell et al., "GRF analogs and fragments: Correlation between receptor binding, activity and structure," Peptides (May/Jun. 1991), 12(3):569-574.

Campbell, R. M. et al., "Rational Design, Synthesis and Biological Evaluation of Novel Growth Hormone Releasing Factor Analogues", Biopolymers 37(2), Jan. 1, 1995.

Cittadini, et al. "Growth Hormone Attenuates Early Left Ventricular Remodeling and Improves Cardiac Function in Rats With Large Myocardial Infarction", J Am Coll/Cardio, (Apr. 1997) 29(5):1109-1116.

Corpas et al., "Growth Hormone (GH)-Releasing Hormone-(1-29) Twice Daily Reverses the Decreased GH and Insulin-Like Growth Factor-I Levels in Old Men", J. Clin. Endoc. Metabol., (Aug. 1992) 75(2):530-535.

Doerks, et al., "Protein annotation: detective work for function prediction", Trends in Genetics, (Jun. 1998), 14(6):248-250.

Dor et al., "Adult pancreatic B-cells are formed by self-duplication rather than stem-cell differentiation." Nature, (May 6, 2004), 429:41-44.

Ehlers, "Recombinant Human GHRH(1-44)NH2", Endocrine (Feb. 2001), 14(1)137-141.

Falutz et al., "Effects of Tesamorelin, a Growth Hormone-Releasing Factor, in HIV_Infected Patients with Abdominal Fat Accumulation: A Randomized Placebo-Controlled Trial With a Safety Extension," Acquir Immune Defic Syndr. (2010), 53: 311-322.

Felix et al., "Synthesis, biological activity and conformational analysis of cyclic GRF analogs," Int. J. Peptide Protein Res. (Dec. 1988), 32(6): 441-454.

Ferninandi et al., "Non-Clinical Pharmacology and Safety Evaluation of TH9507, a Human Growth Hormone-Releasing Factor Analogue," Basic & Clin Pharmacol Toxicol. (2007), 100: 49-58.

Fiaschi-Taesch et al., "Hepatocyte Growth Factor Enhances Engraftment and Function of Nonhuman Primate Islets," Diabetes, (Oct. 2008), 57:2745-2754.

Frascarelli et al., "Effect of ghrelin and synthetic growth hormone secretagogues in normal and ischemic rat heart", Basic Res Cardiol, (Aug. 21, 2003) 98:401-405.

Frohman et al., "Dipeptidylpeptidase IV and Trypsin-like Enzymatic Degradation of Human Growth Hormone-releasing Hormone in Plasma," ./. Clin. Invest. (1989), 83, 1533-1540.

Gomes et al., "S-nitrosoglutathione reductase (GSNOR) enhances vasculogenesis by mesenchymal stem cells", Proc Natl Acad Sci USA, (Feb. 19, 2013), 110(8):2834-2839.

Gomes et al., Submission ID#13475. S-nitrosoglutathione Reductase (GSNOR) Enhances Vasculogenesis by Mesenchymal Stem Cells, World Stem Cell Summit, (Dec. 5, 2012), [retrieved from the Internet Jun. 8, 2014: http://www.worldstemcellsummit.com/files/2012-AbstractSubmissions.pdf] p. 1 and 2.

Goodman & Gilman's The Pharmaceutical Basis of Therapeutics, 6th Ed., MacMillan Publishing Co., New York, (1980).

Granata et al. "Growth hormone-releasing hormone promotes survival of cardiac myocytes in vitro and protects against ischaemia-reperfusion injury in rat heart", Cardiovasc Res, (Mar. 17, 2009) 83:303-312.

Granata et al., "Obestatin promotes survival of pancreatic beta-cells and human islets and induces expression of genes involved in the regulation of beta-cell mass and function," Diabetes, (Apr. 2008), 57:967-979.

Guarcello et al., "Growth hormone releasing hormone receptors on thymocytes and splenocytes from rats," Cell Immunol, (1991), 136:291-902.

Havt et al., "The expression of the pituitary growth hormone-releasing hormone receptor and its splice variants in normal and neoplastic human tissues," Proc Natl Acad Sci USA (Nov. 29, 2005), 102(48):17424-17429.

Houssay. "Role of the hvDophysis in carbohydrate metabolism and diabetes]." Folia Endoctrinol Mens Incretologia Incretoterapia,(1950) 3(2):127-136.

Huising et al., "CRFR1 is expressed on pancreatic B cells, promotes B cell proliferation, and potentiates insulin secretion in a glucose-dependent manner," Proc Natl Acad Sci USA, (Jan. 12, 2010), 107(2): 912-917.

International Search Report for PCT/US2012/067690 dated Mar. 28, 2013.

International Search Report for PCT/US2013/077453 dated Jul. 11, 2014.

Izdebski et al., Synthesis and biological evaluation of superactive agonists of growth hormone-releasing hormone, Proc. Natl. Acad. Sci. USA, (May 1995), 92:4872-4876.

(56) References Cited

OTHER PUBLICATIONS

Jabs et al., "Reduced insulin secretion and content in VEGF—a deficient mouse pancreatic islets," *Exp Clin Endoctrinol Diabetes* (2008), 116 Suppl. 1:S46-49.

Kanashiro-Takeuchi et al., Activation of growth hormone releasing hormone (GHRH) receptor stimulates cardiac reverse remodeling after myocardial infarction (MI), *Proc. Natl. Acad. Sci. USA*, (Jan. 2012), 109(2):559-563.

Kanashiro-Takeuchi, et al. "Cardioprotective effects of growth hormone-releasing hormone agonist after myocardial infarction", *Proc Natl Acad Sci USA*, (Jan. 21, 2010) 107(6):2604-2609.

Kanashiro-Takeuchi, et al., "Growth Hormone Releasing Hormone (GHRH) Agonist Improves Cardiac Performance in the Chronic Model of Myocardial Infarction (MI) in Rats", *Best of AHA Specialty Conferences Poster Session: BCVS 2010*, Chicago, Illinois, Nov. 15, 2010 (Abstract).

Kanashiro-Takeuchi, et al., "Growth Hormone Releasing Hormone (GHRH) Agonist Improves Cardiac Performance in the Chronic Model of Myocardial Infarction (MI) in Rats", *The Heart Failure Society of America (HFSA) 14th Annual Scientific Meeting*, San Diego, California, Sep. 12-15, 2010 (Abstract).

Kanashiro-Takeuchi, et al., "Growth Hormone Releasing Hormone (GHRH) Receptor Dependency for Cardioprotective Repair", *American Heart Association Scientific Sessions*, Orlando, Florida, Nov. 12-16, 2011 (Abstract).

Khorram et al., "Effects of [Norleucine27] Growth Hormone-Releasing Hormone (GHRH) (1-29)-NH2 Administration on the Immune System of Aging Men and Women," *J Clin Endocrinol Metab*, (1997), 82(11):3590-3596.

Kiaris et al., "Extrapituitary effects of the Growth Hormone-Releasing Hormone", *Vitam Horm*, (2005) 70:1-24.

Kiaris, et al., "Ligand-dependent and -independent effects of splice variant 1 of growth hormone-releasing hormone receptor", *Proc Natl Acad Sci USA*, (Aug. 5, 2003), 100(16):9512-9517.

Kirk et al., "Treatment with GHRH(1-29)NH2 in children with idiopathic short stature induces a sustained increase in growth velocity," *Clinical Endocrinol.* (Oct. 1994) 41(4):487-493.

Kovacs et al., "An evaluation of intravenous, subcutaneous, and in vitro activity of new agmatine analogs of growth-hormone releasing hormone hGH-RW (1-29)NH2," *Life Science*, (1988), 42(1): 27-35.

Lehmann et al., "Has time come for new goals in human islet transplantation?," *Am J Transplant*, (2008), 8:1096-1100.

Letsch et al., "Growth hormone-releasing hormone (GHRH) antagonists inhibit the proliferation of androgen-dependent and -independent prostate cancers," *Proc Natl Adac Sci USA*, (Feb. 4, 2003), 100(3):1250-1255.

Ling et al., "Isolation, primary structure, and synthesis of human hypothalamic somatocrini: growth hormone-releasing factor," *Proc Natl Acad Sci USA*, (1984), 81:4302-4306.

Marleau et al., "Cardiac and peripheral actions of growth hormone and its releasing peptides: Relevance for the treatment of cardiomyopathies", *Cardiovasc Res*, (2006) 69:26-35.

Mayo Clinic "Intestinal Ischemia" accessed on Feb. 9, 2015 at www.mayoclinic.org/diseases-conditions/intestinal-ischemia/basics/causes/con-20023818. Published Aug. 17, 2012.

Merrifield, Solid Phase Peptide Synthesis. I. The Synthesis of a Tetrapeptide, *Journal of the American Chemical Society*, (1963), 85(14):2149-2154.

Mill et al. "The Early Administration of Growth Hormone Results in Deleterious Effects on Ventricular Remodeling After Acute Myocardial Infarction", *Arq Bras Cardiol*, (Feb. 2005) 84(2):115-121.

Modern Pharmaceutics, Banker & Rhodes, Marcel Dekker, Inc., New York and Basel, (1979).

Muranishi et al., "Lipophilic Peptides: Synthesis of Lauroyl Thyrotropin-Releasing Hormone and Its Biological Activity," *Pharm. Res.* (May 1991), 8(5)649-652.

Ngo, et al., "Computational Complexity, Protein Structure Prediction, and the Levinthal Paradox", *The Protein Folding Problem and Tertiary Structure Prediction*, (1994), pp. 433-440 and 492-495 only.

Nielsen et al., "Beta cell proliferation and growth factors," *J. Mol. Med.* (1999), 77:62-66.

Office Action cited in Chinese Application No. 201280070383.9 dated Oct. 21, 2015.

Omerovic, et al. "Growth Hormone Improves Bioenergetics and Decreases Catecholamines in Postinfarct Rat Hearts", *Endocrinology*, (2000) 141(12):4592-4599.

Phillips, "The challenge of gene therapy and DNA delivery", *J. Pharm Pharmacology*, (May 2001), 53:1169-1174.

Rekasi et al., "Isolation and sequencing of cDNAs for splice variants of growth hormone-releasing hormone receptors from human cancers," *Proc Natl Acad Sci USA*, (Sep. 12, 2000), 97(19): 10561-10566.

Rivier et al., "Potent Long-Acting Growth Hormone Releasing Factor Analogues" *Annals NY Acad. Sci.* 572:44-550. Published 1988.

Ross et al., "Treatment of Growth-Hormone Deficiency with Growth-Hormone-Releasing Hormone," *Lancet* 1 (Jan. 3, 1987), 8523:5-8.

Schally et al., Growth Hormone *Secretagogues in Clinical Practice*, (Ch. 10), (1998), pp. 131-142, Marcel Dekker, Inc., New York.

Shapiro et al., "International trial of the Edmonton protocol for islet transplantation," *N Engl J Med*, (2006), 355:1318-1330.

Shen et al. "GH replacement fails to improve ventricular function in hypophysectomized rats with myocardial infarction", *Am J Physiol*, (Nov. 1996) 271(5 Pt 2):H1721-H1727.

Skolnick et al., "From genes to protein structure and function: novel applications of computational approaches in the genomic era", *Trends in Biotech*, (Jan. 2000), 18(1):34-39.

Soule et al. "Incorporation of D-Ala2 in growth hormone-releasing hormone (1-29)-NH2 increases the half-life and decreases metabolic clearance in normal men" J. Clin. Endocrinol. Metab. 79:1208-1211. Published 1994.

Supplementary European Search Report for EP12860298 dated Sep. 11, 2015.

Takano et al., "Human growth hormone-releasing hormone (hGH-RH; hGRF) treatment of four patients with GH deficiency," *Endocrinol. Japan* (1988) 35(5); 775-781.

Takeuchi, et al. "Growth-Hormone-Releasing-Hormone (GHRH) Agonist as a Potential Cardioprotective Agent in Rats with Post-Myocardial Infarction (MI)", *American Heart Association*, Jun. 8, 2009 (Abstract).

The Effect of GHRH Therapy on Myocardial Structure and Fuction in Congestive Heart Failure, accessed at <http://www.clinicaltrials.gov/show/NCT00791843>, first received Nov. 13, 2008, last verified Dec. 2013.

Thorner et al., "Acceleration of Growth in Two Children Treated with Human Growth Hormone-Releasing Factor," *N. Engl. J. Med.* (Jan. 3, 1985), 312(1):4-9.

Tivesten et al. "The Growth Hormone Secretagogue Hexarelin Improves Cardiac Function in Rats After Experimental Myocardial Infarction", *Endocrinology*, (2000), 141(1):60-66.

Umprot Direct Submission P01286 (Oct. 31, 2012) [Retrieved from the Internet on Jun. 9, 2014: <<http://www.uniprot.org/uniproUP01286.txt?version=124>>].

Vance, "Growth hormone for the elderly?," *N. Eng. J. Med* (1990), 323(1):52-54.

Vance, "Growth-Hormone-Releasing Hormone," *Clin Chem*, (1990), 36:415-420.

Vasavada et al., "Growth factors and beta cell replication," *Int J. Biochem Cell Biol, Epub 31*, (Aug. 2005), 38(5-6):931-950.

Wells, "Additivity of Mutational Effects in Proteins", *Biochemistry*, (Sep. 18, 1990), 29(37):8509-8517.

Witkowska E.W. et al., "Tryptic Hydrolysis of HGH-RH(1-29)-NH2 Analogues Containing Lys or Orn in Positions 21 and 21", Journal of Peptide Science, 7(1), Jan. 1, 2001.

Zarandi et al., "Synthesis and in vitro and in vivo activity of analogs of growth hormone-releasing hormone (GH-RH) with C-terminal agmatine," *Int. J. Peptide Protein Res.* (Dec. 1990), 36(6):499-505.

(56) References Cited

OTHER PUBLICATIONS

Zarandi et al., Potent agonists of growth hormone-releasing hormone. Part I. *Int. J. Peptide Res.* 39: 211-7 (1992).

Ziegler et al., "Dehydroepiandrosterone induces a neuroendocrine phenotype in nerve growth factor-stimulated chromaffin pheochromocytoma PC12 cells," *Endocrinology*, (2008), 149:320-328.

Ziegler et al., "Expression of neuropeptide hormone receptors in human adrenal tumors and cell lines: Antiproliferative effects of peptide analogues," *Proc Natl Acad Sci USA*, (Sep. 15, 2009), 106(37):15879-15884.

\* cited by examiner

SEQUENCE LISTING

<160> NUMBER OF SEQ ID NOS: 39

<210> SEQ ID NO 1
<211> LENGTH: 30
<212> TYPE: PRT
<213> ORGANISM: Artificial Sequence
<220> FEATURE:
<223> OTHER INFORMATION: synthetic peptide

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 2

Xaa Ala Asp Ala Ile Xaa Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE

```
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 3

Xaa Ala Asp Ala Ile Xaa Thr Ala Ser Tyr Arg Xaa Val Leu Xaa Gln
 1               5                  10                  15

Leu Ser Ala Arg Xaa Leu Leu Gln Asp Ile Xaa Asp Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 4

Xaa Ala Asp Ala Ile Xaa Thr Asn Ser Tyr Arg Xaa Val Leu Xaa Gln
 1               5                  10                  15

Leu Ser Ala Arg Xaa Leu Leu Gln Asp Ile Xaa Asp Xaa
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 5

Xaa Ala Asp Ala Ile Xaa Thr Thr Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 6

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 7
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 7

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 8

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 9
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 9

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 10

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Xaa
            20                  25
```

```
<210> SEQ ID NO 11
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 11

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 12

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25
```

<210> SEQ ID NO 13
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 13

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 14
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 8-Aminocaprylyl-NH2

<400> SEQUENCE: 14

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 15

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 16

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa

```
<210> SEQ ID NO 17
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 17

Xaa Ala Asp Ala Ile Phe Thr Asn Ser Tyr Arg Xaa Val Leu Xaa Gln
 1               5                  10                  15

Leu Ser Ala Arg Xaa Leu Leu Gln Asp Ile Xaa Asp Arg Xaa
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 18

Xaa Ala Asp Ala Ile Phe Thr Asn Ser Tyr Arg Xaa Val Leu Xaa Gln
 1               5                  10                  15
```

Leu Ser Ala Arg Xaa Leu Leu Gln Asp Ile Xaa Ser Arg Xaa
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 19

Xaa Ala Asp Ala Ile Phe Thr Thr Ser Tyr Arg Xaa Val Leu Xaa Gln
1               5                   10                  15
Leu Ser Ala Arg Xaa Leu Leu Gln Asp Ile Xaa Asp Arg Xaa
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 20

Xaa Ala Asp Ala Ile Phe Thr Ala Ser Tyr Arg Xaa Val Leu Xaa Gln
1               5                   10                  15

```
Leu Ser Ala Arg Xaa Leu Leu Gln Asp Ile Xaa Asp Arg Xaa
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 21

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 22

Xaa Ala Asp Ala Ile Phe Thr Asn Ser Tyr Arg Xaa Val Leu Xaa Gln
```

Leu Ser Ala Arg Xaa Leu Leu Gln Asp Ile Xaa Asp Arg Xaa
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 23

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 24

-continued

```
Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

<210> SEQ ID NO 25
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 25

```
Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

<210> SEQ ID NO 26
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 26

```
Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

<210> SEQ ID NO 27
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 27

```
Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

<210> SEQ ID NO 28
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 28

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 6-aminohexanoyl-NH2

<400> SEQUENCE: 29

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 6-aminohexanoyl-NH2

<400> SEQUENCE: 30

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (2)..(2)
<223> OTHER INFORMATION: Xaa is alpha-aminobutyric acid
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is gamma-amino butanoyl-NH2

<400> SEQUENCE: 31

Xaa Xaa Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 32
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)

<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 32

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 33
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 33

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE

```
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 34

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 35
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 35

Xaa Ala Asp Ala Ile Phe Thr Gln Ser Tyr His Xaa Val Leu Xaa Gln
1               5                   10                  15

Leu Ser Ala His Xaa Leu Leu Gln Asp Ile Xaa Asp Xaa
            20                  25

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
```

```
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is gamma-amino butanoyl-NH-CH3

<400> SEQUENCE: 36

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 37
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is acetyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 37

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
```

```
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 38

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 39
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is Gln-gamma-amino butanoyl-NH2

<400> SEQUENCE: 39

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30
```

US 10,555,987 B2

GHRH AGONISTS FOR THE TREATMENT OF ISCHEMIC DISORDERS

CROSS-REFERENCE TO RELATED APPLICATIONS

This application is a divisional of U.S. patent application Ser. No. 14/138,391, filed Dec. 23, 2013, which in turn claims priority to U.S. Provisional Application No. 61/745,051 filed on Dec. 21, 2012, and to U.S. Provisional Application No. 61/892,963 filed on Oct. 18, 2013, each of which are hereby incorporated by reference in their entireties.

GOVERNMENT INTERESTS

This work is funded by US National Institutes of Health grant NIH RO1 HL-107110. This work was supported by Medical Research Service grants from the Veterans Affairs Department, USA. The government may have certain rights in this application.

INCORPORATION BY REFERENCE OF A SEQUENCE LISTING SUBMITTED AS A TEXT FILE VIA EFS-WEB

This application contains, as a separate part of disclosure, a Sequence Listing in computer-readable form (filename: 51875A_Seqlisting.txt; Size: 32,768 bytes; created Nov. 21, 2017), which is incorporated by reference in its entirety.

BRIEF SUMMARY OF THE INVENTION

Embodiments of the present disclosure are directed to GHRH agonists and peptide compositions, and methods to treat disorders, such as ischemia and reperfusion injury. In one embodiment, a method of treating a reperfusion injury in a subject in need may involve administering a therapeutically effective amount of a GHRH agonist peptide to the subject. In an additional embodiment, the reperfusion injury may be caused by ischemia or hypoxia.

In a further embodiment, a method of treating a subject with ischemic disorder in a subject in need thereof may involve administering a therapeutically effective amount of a GHRH agonist peptide to the subject. The ischemic disorder may be caused by cardiovascular disease, cardiomyopathy, myocardial stunning, peripheral vascular disease, intermittent claudication, tachycardia, ischemia-reperfusion, myocardial infarction, cardiac fibrosis, cardiac weakness, acute renal failure, stroke, hypotension, embolism, thromboembolism (blood clot), sickle cell disease, localized pressure to extremities to the body, or tumors.

In an additional embodiment, a method of promoting vasculogenesis in a subject in need thereof may involve administering a therapeutically effective amount of a GHRH agonist peptide to the subject.

In a further embodiment, a method of promoting differentiation of mesenchymal stem cells into endothelial cells may involve contacting mesenchymal stem cells with a GHRH agonist peptide in vitro or in vivo.

In the foregoing embodiments, the GHRH agonist peptide comprises a peptide of formula:

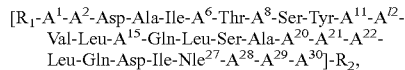

[$R_1$-$A^1$-$A^2$-Asp-Ala-Ile-$A^6$-Thr-$A^8$-Ser-Tyr-$A^{11}$-$A^{12}$-Val-Leu-$A^{15}$-Gln-Leu-Ser-Ala-$A^{20}$-$A^{21}$-$A^{22}$-Leu-Gln-Asp-Ile-Nle$^{27}$-$A^{28}$-$A^{29}$-$A^{30}$]-$R_2$, wherein $R_1$ is Ac, Tfa, or is absent,
$A^1$ is Tyr, Dat, or N-Me-Tyr,
$A^2$ is Ala, D-Ala, Abu, or D-Abu,
$A^6$ is Phe or Fpa5,
$A^8$ is Asn, Ala, Gln, Thr, or N-Me-Ala,
$A^{11}$ is Arg, His, or Har,
$A^{12}$ is Orn, or Lys(Me)$_2$,
$A^{15}$ is Abu or Ala,
$A^{20}$ is Arg, His, or Har,
$A^{21}$ is Orn, or Lys(Me)$_2$,
$A^{22}$ is Leu, or Orn,
$A^{28}$ is Ser, or Asp,
$A^{29}$ is Arg, Har, Agm, D-Arg, or D-Har,
$A^{30}$ is Arg, Agm, Ada, Amc, Aha, Apa, Har, D-Arg, D-Har, Gab, Gln, D-Gln, Gln-Gab, D-Gln-Gab, or is absent,
$R_2$ is —NH$_2$, —NH—CH$_3$, —NH—CH$_2$—CH$_3$, —OH, —NHR$_3$, —N(R$_3$)$_2$, or —OR$_3$, wherein R$_3$ is any of C$_{1-12}$ alkyl, C$_{2-12}$ alkenyl, or C$_{2-12}$ alkynyl,
and pharmaceutically acceptable salts thereof, and wherein the agonist peptide is different from SEQ ID NO: 1 in at least one amino acid residue.

DETAILED DESCRIPTION

Figure 1:
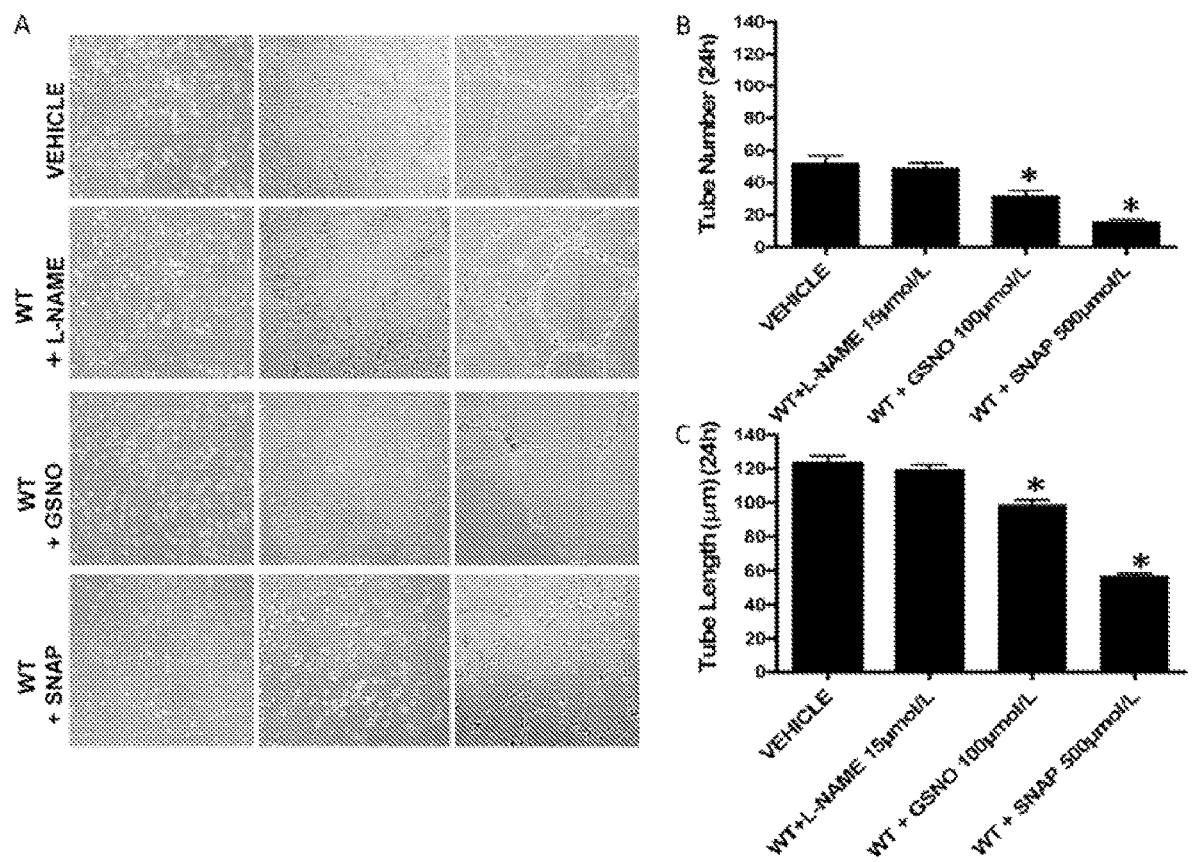
FIG. 1 illustrates the effect of GHRH agonist peptides MR-356 (P-20356) and MR-409 (P-27409) on nitrosoglutathione reductase$^{-/-}$ (GSNOR$^{-/-}$) mesenchymal stem cells (MSCs) and tube formation. Panel A represents images of tube formation in Matrigel and Panel B represents bar graphs quantifying the tubes formed.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

As used herein and in the appended claims, the singular forms "a", "an", and "the" include plural reference unless the context clearly dictates otherwise. Thus, for example, reference to an "antioxidant" is a reference to one or more antioxidants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic to a patient whereby the therapeutic positively impacts the tissue to which it is targeted. The peptides/compounds described herein can be administered either alone or in combination (concurrently or serially) with other pharmaceuticals. For example, the peptides/compounds can be administered in combination with other anti-cancer or anti-neoplastic agents, or in combination with other cancer therapies other than chemotherapy, such as, for example, surgery or radiotherapy. In some embodiments, the peptides/compounds described herein can also be administered in combination with (i.e., as a combined formulation or as separate formulations) other therapeutics.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, prevent or improve an unwanted condition, disease or symptom of a patient.

A "therapeutically effective amount" or "effective amount" of a composition is a predetermined amount calculated to achieve the desired effect, i.e., to ameliorate, prevent or improve an unwanted condition, disease or symptom of a patient. The activity contemplated by the present methods may include both therapeutic and/or prophylactic treatment, as appropriate. The specific dose of the peptides/compounds or the peptides administered according to this invention to obtain therapeutic and/or prophylactic effects will, of course, be determined by the particular circumstances surrounding the case, including, for example, the peptides/compounds administered, the route of administration, and the condition being treated. The effective amount administered may be determined by a physician in the light of the relevant circumstances including the condition to be treated, the choice of peptides/compounds to be administered, and the chosen route of administration. A therapeutically effective amount of the peptide/compound of this invention is typically an amount such that when it is administered in a physiologically tolerable excipient composition, it is sufficient to achieve an effective systemic concentration or local concentration in the target tissue.

Generally speaking, the term "tissue" refers to any aggregation of similarly specialized cells which are united in the performance of a particular function.

As used herein, "analog" of polypeptides refers to an amino acid sequence that is altered by one or more amino acid residues. The analog may have "conservative" changes, wherein a substituted amino acid has similar structural or chemical properties (e.g., replacement of leucine with isoleucine). More rarely, an analog may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

By the term "modulate," it is meant that any of the mentioned activities, are, e.g., increased, enhanced, increased, agonized (acts as an agonist), or promoted. Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

The terms "subject", "patient" or "individual" are used interchangeably herein, and refers to a mammalian subject to be treated. In some embodiments, the patient is a human. In some cases, the methods can be used in experimental animals, in veterinary application, and in the development of animal models for disease, including, but not limited to, rodents including mice, rats, and hamsters; and primates. In some embodiments, the patient is a patient in need thereof.

As used herein, the phrase "in need thereof" means that the patient has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

"Treatment" is an intervention performed with the intention of preventing the development or altering the pathology or symptoms of a disorder. Accordingly, "treatment" can refer to therapeutic treatment or prophylactic or preventative measures. In some embodiments, the treatment is for therapeutic treatment. In some embodiments, the treatment is for prophylactic or preventative treatment. Those in need of treatment can include those already with the disorder as well as those in which the disorder is to be prevented.

As used herein, "ameliorated" or "treatment" refers to a symptom which is approaches a normalized value (for example a value obtained in a healthy patient or individual), e.g., is less than 50% different from a normalized value, is less than about 25% different from a normalized value, is less than 10% different from a normalized value, or is not significantly different from a normalized value as determined using routine statistical tests.

"Agonist of GHRH" means a compound or peptide other than GHRH which has the function of binding to and stimulating GHRH receptors, resulting in the release of growth hormone, or another physiological, endocrine or cellular response specific for GHRH. In some embodiments, a GHRH agonist may activate GHRH receptor and may not result in the release of growth hormone. A GHRH agonist may comprise a full length GHRH sequence in which certain modifications have been made, e.g., amino acid residues have been substituted, side groups have been added. The amino acid sequence of hGHRH (1-30), starting at the N-terminal part is: $Tyr^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Lys^{12}$-$Val^{13}$-$Leu^{14}$-$Gly^{15}$-$Gln^{16}$-$Leu^{17}$-$Ser^{18}$-$Ala^{19}$-$Arg^{20}$-$Lys^{21}$-$Leu^{22}$-$Leu^{23}$-$Gln^{24}$-$Asp^{25}$-$Ile^{26}$-$Met^{27}$-$Ser^{28}$-$Arg^{29}$-$Gln^{30}$ (SEQ ID NO: 1). A GHRH agonist may comprise a GHRH sequence to which amino acid deletions, insertions, and/or substitutions have been made. A GHRH agonist may also be a fragment or modified fragment of GHRH having the capability to bind to the GHRH receptor and stimulate release of growth hormone. The biological activity of GHRH is understood to reside in the N-terminal amino acid sequences of the hormone. Thus, fragments or modified fragments between amino acid residues 1 and 30, or between amino acid residues 1 and 29 are expected to be useful.

For example, an agonist of GHRH can include one or more features that protect it against degradation by biological, chemical, and/or other processes. For example, such features can protect the GHRH agonist peptide from proteolytic enzymes in the wound milieu (fluids), e.g., from proteases secreted by neutrophils. Such proteolytic enzymes can inactivate (e.g., degrade or split) unprotected peptides such as unprotected GHRH. Such protective features can include, for example, the replacement of certain amino acids (residues) in the native peptide sequence of GHRH with other different amino acids (residues). In some embodiments, replacement of Arg in position 29 by Agm (agmatine, 4-guanidino-butylamine) may provide resistance to enzymatic degradation of the peptide at the C-terminus. In some embodiments, replacement of Tyr in position 1 by desaminotyrosine (Dat) may result in peptides with increased biological activities as a result of the resistance to N-terminal enzymatic degradation. Similarly, substitutions of hydrophobic groups at the C-terminal of peptides can result in significant increase in specific activity of the peptides.

Tissues deprived of blood and oxygen undergo ischemic necrosis or infarction with possible irreversible organ damage. Once the flow of blood and oxygen is restored to the organ or tissue (reperfusion), the organ does not immediately return to the normal preischemic state. Reperfusion of the blood flow is necessary to resuscitate the ischemic or hypoxic tissue or organ. Timely reperfusion facilitates salvage of cells and decreases morbidity and mortality. However, reperfusion of an ischemic area may result in a paradoxical dysfunction including marked endothelial cell dysfunction, which results in vasoconstriction, and acute immune response due to platelet and leukocyte activation, increased oxidant production, and increased fluid and protein extravasation.

In an effort to provide treatment for ischemia, a number of angiogenesis techniques are now in clinical trial, including gene therapy and the use of growth factors such as vascular endothelial growth factor (VEGF) or basic fibroblast growth factor (bFGF) to induce or augment collateral blood vessel production. Recent studies have demonstrated the role of growth hormone releasing hormone (GHRH) in promoting vasculogenesis, mediated through differentiation of mesenchymal stem cells. The present invention relates to growth hormone releasing hormone (GHRH) analogous peptides having high binding affinity to GHRH receptor in vitro and having influence on the function of the pituitary gland in vivo. More particularly, the present invention relates to hGHRH analogs of 29 or 30 amino acids that show much higher affinity to the GHRH receptor than the native hGHRH(1-30) SEQ ID NO: 1. This invention also relates to a pharmaceutical composition comprising any one of said GHRH agonists and to the use of these agonistic peptides in the treatment of ischemic disorders.

Disclosed herein are a novel series of synthetic peptide analogs of hGHRH(1-29) or hGHRH(1-30). The novel synthetic peptides of this invention exhibit high activities in stimulating the release of pituitary growth hormone (GH) in animals, including humans. They also show extremely high binding capacity to the hGHRH receptor. These synthetic hGHRH analogs also retain their physiological activity in solution for an extended period of time and resist enzymatic degradation in the body. The stronger GH releasing potencies of the new analogs in vivo, as compared to previously described ones, results from combination of replacements in hGHRH(1-29) or hGHRH(1-30) and from resistance to in vivo degradation. Without in any way limiting the invention or its scope, applicants wish to express their understanding that the retention of activity in vitro and resistance to in vivo degradation are due to multiple substitutions in the molecule: incorporation of N-Me-Tyr or des-amino-Tyr (Dat) in position 1 which protect peptides from the degradation at the N-terminus; incorporation of agmatine (Agm) or —NH—CH$_3$ or —NH—CH$_2$—CH$_3$ at position 29 or extension of the C-terminus with an omega-amino acid which protects peptides from degradation at the C-terminus; and also the replacements of both lysines in the synthetic peptides with ornithine (Orn), which is a poor substrate for trypsin-like enzymes; Gly at residue 15 by Abu. To increase chemical stability, Asn at position 8 is replaced by Gln, Thr, or Ala. And Met in position 27 is replaced by norleucine (Nle). Replacement of other residues in the peptides and the combination of these replacements also are found to promote biological activity.

In some embodiments, the GHRH agonist peptide is represented by the formula:

[R$_1$-A$^1$-A$^2$-Asp-Ala-Ile-A$^6$-Thr-A$^8$-Ser-Tyr-A$^{11}$-A$^{12}$-Val-Leu-A$^{15}$-Gln-Leu-Ser-Ala-A$^{20}$-A$^{21}$-A$^{22}$-Leu-Gln-Asp-Ile-Nle$^{27}$-A$^{28}$-A$^{29}$-A$^{30}$]-R$_2$.

In some embodiments, R$_1$ is Ac, Tfa, or is absent;
In some embodiments, A$^1$ is Tyr, Dat, or N-Me-Tyr;
In some embodiments, A$^2$ is Ala, D-Ala, Abu, or D-Abu;
In some embodiments, A$^6$ is Phe or Fpa5;
In some embodiments, A$^8$ is Asn, Ala, Gln, Thr, or N-Me-Ala;
In some embodiments, A$^{11}$ is Arg, His, or Har;
In some embodiments, A$^{12}$ is Orn, or Lys(Me)$_2$;
In some embodiments, A$^{15}$ is Abu or Ala;
In some embodiments, A$^{20}$ is Arg, His, or Har;
In some embodiments, A$^{21}$ is Orn, or Lys(Me)$_2$;
In some embodiments, A$^{22}$ is Leu, or Orn;
In some embodiments, A$^{28}$ is Ser, or Asp;
In some embodiments, A$^{29}$ is Arg, Har, Agm, D-Arg, or D-Har;
In some embodiments, A$^{30}$ is Arg, Agm, Ada, Amc, Aha, Apa, Har, D-Arg, D-Har, Gab, Gln, D-Gln, Gln-Gab, D-Gln-Gab, or is absent;
In some embodiments, R$_2$ is —NH$_2$, —NH—CH$_3$, —NH—CH$_2$—CH$_3$, —OH, —NHR$_3$, —N(R$_3$)$_2$, or —OR$_3$, wherein R$_3$ is any of C$_{1-12}$ alkyl, C$_{2-12}$ alkenyl, or C$_{2-12}$ alkynyl, and pharmaceutically acceptable salts thereof;
In some embodiments, the agonist peptide is different from SEQ ID NO: 1 in at least one amino acid residue; and
In some embodiments, if the A$^{29}$ is Agm, then A$^{30}$ and R$_2$ are absent, and A$^1$ is N-Me-Tyr.

The nomenclature used to define the amino acid residues and synthetic peptides is according to the IUPAC-IUB Commission on Biochemical Nomenclature (European J. Biochem., 1984, 138, 9-37). The naturally occurring amino acids found in proteins are depicted by the following three letter codes: Gly, Ala, Val, Leu, Ile, Ser, Thr, Lys, Arg, Asp, Asn, Glu, Gln, Cys, Met Phe, Tyr, Pro, Trp and His.

Other abbreviations used are:
Aah alpha-amino-hexanoic acid
Aap alpha-amno-pentanoic acid
Abu alpha-aminobutyric acid
Ac acetyl
AcOH acetic acid
Ac2O acetic anhydride
Ada 12-aminododecanoyl
Agrn agmatine
Aha 6-aminohexanoyl
AM aminomethyl
Amc 8-Aminocaprylyl
Apa 5-Aminopentanoyl
Aib alpha-aminoisobutyroyl
Boc tert-butyloxycarbonyl
Bom benzyloxymethyl
2BrZ 2-bromo-benzyloxycarbonyl
Bul tertiary butyl (ester)
Bzl benzyl cHx cyclohexyl
2ClZ 2-chloro-benzyloxycarbonyl
2ClTrt 2-chlorotrityl
Cpa para-chlorophenylalanine
Dat des-amino-tyrosine
DCM dichloromethane
DIC N,N'-diisopropylcarbodiimide
DIEA diisopropylethylamine
DMF dimethylformamide
Et ethyl
Fm fluorenylmethyl
Fmoc fluorenylmethoxycarbonyl
For formyl
Fpa mono-or poly-fluorinated Phe(fluorine substitution on the aromatic ring)
Fpa5 pentafluoro-Phe
Gab gamma-amino butanoyl GH growth hormone
GHRH GH releasing hormone
Har homoarginine
HBTU 2-(1H-Benzotriazol-1-yl)-1,1,3,3-tetramethyluronium hexaflourophosphate
hGHRH human GHRH
HOBt 1-hydroxybenzotriazole
HPLC high performance liquid chromatography
Ibu isobutyryl
MBHA para-methylbenzhydrylamine
Me methyl
MeOH methanol
MeCN acetonitrile
Mmt 4-methoxytrityl
Mtr 4-methoxy-2,3,6-trimethylbenzenesulphonyl
N-Me-Ala N-methyl-Ala
N-Me-Tyr N-methyl-Tyr
Nle norleucine
NMM N-methylmorpholine
Oaa omega-amino acid
Orn ornithine
PAM phenylacetamidomethyl
Pbf 2,2,4,6,7-pentamethyl-dihydrobenzofurane-5-sulfonyl
Ph phenyl
PS polystyrene
rGHRH ratGHRH
RP-HPLC reversed phase HPLC
SPA para-sulfonyl-phenoxyacetyl
tBu tertiary butyl (ether)
TFA trifluoroacetic acid
Tfa trifluoroacetyl
Tos para-toluenesulfonyl
Trt trityl (triphenylmethyl)
Z benzyloxycarbonyl In some embodiments, the GHRH agonist peptide may be of the formula:

[$R_1$-$A^1$-$A^2$-Asp-Ala-Ile-$A^6$-Thr-$A^8$-Ser-Tyr-Arg-$Orn^{12}$-Val-Leu-$Abu^{15}$-Gln-Leu-Ser-Ala-Arg-$Orn^{21}$-Leu-Leu-Gln-Asp-Ile-$Nle^{27}$-$A^{28}$, $A^{29}$, $A^{30}$]-$R_2$, wherein $R_1$ is Ac or is absent,
$A^1$ is Tyr, Dat, or N-Me-Tyr,
$A^2$ is Ala, D-Ala, Abu, or D-Abu,
$A^6$ is Phe or Fpa5,
$A^8$ is Asn, Ala, Gln, or Thr,
$A^{28}$ is Ser, or Asp,
$A^{29}$ is Arg, Agm, or D-Arg,
$A^{30}$ is Arg, Agm, Ada, Amc, Aha, Apa, Har, D-Arg, D-Har, Gab, Gln, D-Gln, or is absent,
$R_2$ is —$NH_2$, —OH, —$NHR_3$, —$N(R_3)_2$, or —$OR_3$, wherein $R_3$ is any of $C_{1-12}$ alkyl, $C_{2-12}$ alkenyl, or $C_{2-12}$ alkynyl,
and pharmaceutically acceptable salts thereof.

In some embodiments, the GHRH agonist peptide may be of the formula:

[$A^1$-$A^2$-Asp-Ala-Ile-$A^6$-Thr-$A^8$-Ser-Tyr-Arg-$Orn^{12}$-Val-Leu-$Abu^{15}$-Gln-Leu-Ser-Ala-Arg-$Orn^{21}$-Leu-Leu-Gln-Asp-Ile-$Nle^{27}$-$A^{28}$, $A^{29}$, $A^{30}$]-$R_2$, wherein $A^1$ is Dat, or N-Me-Tyr,
$A^2$ is Ala, or D-Ala,
$A^6$ is Phe or Fpa5,
$A^8$ is Asn, Gln, or Thr,
$A^{28}$ is Ser, or Asp,
$A^{29}$ is Arg, Agm, or D-Arg,
$A^{30}$ is Arg, Agm, Ada, Amc, Aha, Apa, Har, D-Arg, D-Har, Gab, Gln, D-Gln, or is absent,
$R_2$ is —$NH_2$, —OH, —$NHR_3$, —$N(R_3)_2$, or —$OR_3$, wherein $R_3$ is any of $C_{1-12}$ alkyl, $C_{2-12}$ alkenyl, or $C_{2-12}$ alkynyl,
and pharmaceutically acceptable salts thereof.

The amino acid sequences of the synthetic peptides are numbered in correspondence with the amino acid residues in wild-type hGHRH(1-30) (SEQ ID NO: 1); thus, for example, the synthetic peptide P-20103 may be represented in an abbreviated form as below:

[N-Me-$Tyr^1$, $Fpa5^6$, $Gln^8$, $Orn^{12}$, $Abu^{15}$, $Orn^{21}$, $Nle^{27}$, $Asp^{28}$, $Agm^{29}$]hGHRH(1-29). The residue N-Me-$Tyr^1$ represents substitution at position 1 of wild-type hGHRH(1-30)$NH_2$ (SEQ ID NO: 1) in place of Tyr; $Fpa5^6$ represents substitution position 6 in place of Phe; $Gln^8$ represents substitution at position 8 in place of Asn, and so on. Further, the amino acid residues at the positions which are not recited in the above abbreviated form (positions $A^2$, $A^3$, $A^4$, $A^5$, $A^7$, $A^9$, $A^{10}$, $A^{11}$, $A^{13}$, $A^{14}$, $A^{16}$, $A^{17}$, $A^{18}$, $A^{19}$, $A^{20}$, $A^{22}$, $A^{23}$, $A^{24}$, $A^{25}$, $A^{26}$) correspond to the amino acid residues of the wild-type hGHRH(1-30)$NH_2$ (SEQ ID NO: 1). Thus, the abbreviated form of a synthetic peptide represent different substitutions when compared to the wild-type hGHRH(1-30)$NH_2$ (SEQ ID NO: 1). Further, in some embodiments, the synthetic peptides described herein may be 30 amino acids in length, as represented by hGHRH(1-30). In some embodiments, the synthetic peptides may be 29 amino acids in length, as represented by hGHRH(1-29)$NH_2$. The convention under which the N-terminal of a peptide is placed to the left, and the C-terminal to the right is also followed herein.

Suitable synthetic hGHRH agonist peptides in abbreviated form are disclosed in Table 1.

TABLE 1

P-20103 [N—Me-$Tyr^1$, $Fpa5^6$, $Gln^8$, $Orn^{12}$, $Abu^{15}$, $Orn^{21}$, $Nle^{27}$, $Asp^{28}$, $Agm^{29}$]hGHRH (1-29)$NH_2$;

P-20105 [N—Me-$Tyr^1$, D-$Ala^2$, $Fpa5^6$, $Gln^8$, $Orn^{12}$, $Abu^{15}$, $Orn^{21}$, $Nle^{27}$, $Asp^{28}$, $Agm^{29}$] hGHRH(1-29)$NH_2$;

P-20107 [N—Me-$Tyr^1$, $Fpa5^6$, $Ala^8$, $Orn^{12}$, $Abu^{15}$, $Orn^{21}$, $Nle^{27}$, $Asp^{28}$, $Agm^{29}$]hGHRH(1-29)$NH_2$;

P-20109 [N—Me-$Tyr^1$, D-$Ala^2$, $Fpa5^6$, $Ala^8$, $Orn^{12}$, $Abu^{15}$, $Orn^{21}$, $Nle^{27}$, $Asp^{28}$, $Agm^{29}$] hGHRH(1-29)$NH_2$;

P-20110 [N—Me-$Tyr^1$, D-$Ala^2$, $Fpa5^6$, $Orn^{12}$, $Abu^{15}$, $Orn^{21}$, $Nle^{27}$, $Agm^{29}$]hGHRH(1-29) $NH_2$;

P-20111 [N—Me-$Tyr^1$, D-$Ala^2$, $Fpa5^6$, $Thr^8$, $Orn^{12}$, $Abu^{15}$, $Orn^{21}$, $Nle^{27}$, $Asp^{28}$, $Agm^{29}$] hGHRH(1-29)$NH_2$;

P-20113 [N—Me-$Tyr^1$, $Fpa5^6$, $Orn^{12}$, $Abu^{15}$, $Orn^{21}$, $Nle^{27}$, $Asp^{28}$, $Agm^{29}$]hGHRH(1-29) $NH_2$;

P-20115 [N—Me-$Tyr^1$, $Fpa5^6$, $Thr^8$, $Orn^{12}$, $Abu^{15}$, $Orn^{21}$, $Nle^{27}$, $Asp^{28}$, $Agm^{29}$]hGHRH (1-29)$NH_2$;

TABLE 1-continued

P-20117 [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH (1-29) NH$_2$;

P-20350 [Dat$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29) NH$_2$:

P-20351 [Ac—N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$] hGHRH(1-29)NH$_2$;

P-20356 [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29) NH$_2$;

P-20357 [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH (1-29)NH$_2$;

P-20358 [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$] hGHRH(1-29)NH$_2$;

P-20359 [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH (1-29)NH$_2$;

P-20360 [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$] hGHRH (1-29)NH$_2$;

P-20361 [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$] hGHRH (1-29)NH$_2$;

P-20367 [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29)NH$_2$;

P-20370 [N—Me-Tyr$^1$, Orn$^{12}$, Abu$^{15}$, Orn$^{21}$, Nle$^{27}$, Asp$^{28}$, Agm$^{29}$]hGHRH(1-29)NH$_2$;

P-20371 [N—Me-Tyr$^1$, Thr$^8$, Orn$^{12}$, Abu$^{15}$, Orn$^{21}$, Nle$^{27}$, Asp$^{28}$, Agm$^{29}$]hGHRH(1-29) NH$_2$;

P-20372 [N—Me-Tyr$^1$, Ala$^8$, Orn$^{12}$, Abu$^{15}$, Orn$^{21}$, Nle$^{27}$, Asp$^{28}$, Agm$^{29}$]hGHRH(1-29) NH$_2$;

P-20373 [N—Me-Tyr$^1$, Gln$^8$, Orn$^{12}$, Abu$^{15}$, Orn$^{21}$, Nle$^{27}$, Agm$^{29}$]hGHRH(1-29)NH$_2$;

P-20374 [N—Me-Tyr$^1$, Orn$^{12}$, Abu$^{15}$, Orn$^{21}$, Nle$^{27}$, Agm$^{29}$]hGHRH(1-29) NH$_2$;

P-20375 [N—Me-Tyr$^1$, Thr$^8$, Orn$^{12}$, Abu$^{15}$, Orn$^{21}$, Nle$^{27}$, Agm$^{29}$]hGHRH(1-29)NH$_2$;

P-20376 [N—Me-Tyr$^1$, Ala$^8$, Orn$^{12}$, Abu$^{15}$, Orn$^{21}$, Nle$^{27}$, Agm$^{29}$]hGHRH(1-29)NH$_2$;

P-21300 [Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;

P-21301 [N—Me-Tyr$^1$, Orn$^{12}$, Abu$^{15}$, Orn$^{21}$, Nle$^{27}$, Asp$^{28}$, Amc$^{30}$]hGHRH(1-30)NH$_2$;

P-21303 [N—Me-Tyr$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;

P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;

P-21305 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$] hGHRH(1-30)NH$_2$;

P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;

P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$] hGHRH(1-30)NH$_2$;

P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$;

P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGH-RH(1-30)NH$_2$;

P-21310 [Dat$^1$-D-Ala$^2$, His$^{11}$, Orn$^{12}$, Abu$^{15}$, His$^{20}$, Orn$^{21}$, Nle$^{27}$, Asp$^{28}$, Amc$^{30}$] hGHRH(1-30)NH$_2$;

P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;

P-22325 [N—Me-Tyr$^1$, Gln$^8$, Orn$^{12}$, Abu$^{15}$, Orn$^{21}$, Nle$^{27}$, Asp$^{28}$, Apa$^{30}$]hGHRH (1-30)NH$_2$;

P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-22327 [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$;

P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-22329 [N—Me-Tyr$^1$, D-Ala$^2$, Orn$^{12}$, Abu$^{15}$, Orn$^{21}$, Nle$^{27}$, Apa$^{30}$]hGHRH(1-30)NH$_2$;

P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$] hGHRH(1-30)NH$_2$;

P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$] hGHRH(1-30)NH$_2$;

P-22332 [N—Me-Tyr$^1$, Orn$^{12}$, Abu$^{15}$, Orn$^{21}$, Nle$^{27}$, Asp$^{28}$, Apa$^{30}$]hGHRH(1-30)NH$_2$;

P-22334 [N—Me-Tyr$^1$, Orn$^{12}$, Abu$^{15}$, Orn$^{21}$, Nle$^{27}$, Apa$^{30}$]hGHRH(1-30)NH$_2$;

P-22335 [N—Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$;

P-22336 [N—Me-Tyr$^1$ Ala$^8$, Orn$^{12}$, Abu$^{15}$, Orn$^{21}$, Nle$^{27}$, Asp$^{28}$, Apa$^{30}$]hGHRH(1-30)NH$_2$;

P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;

P-23251 [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$;

P-23252 [Dat$^1$-D-Ala$^2$, Orn$^{12}$, Abu$^{15}$, Orn$^{21}$, Nle$^{27}$, Asp$^{28}$, Har$^{30}$]hGHRH(1-30)NH$^2$;

P-23253 [Dat$^1$, Orn$^{12}$, Abu$^{15}$, Orn$^{21}$, Nle$^{27}$, Asp$^{28}$, Har$^{30}$]hGHRH(1-30)NH$^2$;

P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;

P-23255 [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$;

TABLE 1-continued

P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23257 [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23259 [N—Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23260 [N—Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23261 [N—Me-Tyr$^1$, Orn$^{12}$, Abu$^{15}$, Orn$^{21}$, Nle$^{27}$, Asp$^{28}$, Har$^{30}$]hGHRH(1-30)NH$_2$;
P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23263 [N—Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23265 [N—Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$;
P-24340 [N—Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$;
P-24341 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;
P-24342 [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$;
P-24344 [Dat$^1$-D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;
P-24345 [N—Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$;
P-24346 [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$;
P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$;
P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$;
P-25501 [N—Me-Tyr$^1$, D-Ala$^2$, Orn$^{12}$, Abu$^{15}$, Orn$^{21}$, Nle$^{27}$, Gab$^{30}$]hGHRH(1-30)NH$_2$;
P-25502 [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$;
P-25503 [N—Me-Tyr$^1$, Abu$^2$, Orn$^{12}$, Abu$^{15}$, Orn$^{21}$, Nle$^{27}$, Gab$^{30}$]hGHRH(1-30)NH$_2$;
P-25504 [Dat$^1$, D-Abu$^2$, Orn$^{12}$, Abu$^{15}$, Orn$^{21}$, Nle$^{27}$, Gab$^{30}$]hGHRH(1-30)NH$_2$;
P-25506 [N—Me-Tyr$^1$, D-Abu$^2$, Orn$^{12}$, Abu$^{15}$, Orn$^{21}$, Nle$^{27}$, Gab$^{30}$]hGHRH(1-30)NH$_2$;
P-25508 [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$;
P-25516 [N—Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$;
P-26802 [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$;
P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$;
P-26804 [N—Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$;
P-27400 [Dat$^1$, D-Ala$^2$, Orn$^{12}$, Abu$^{15}$, Orn$^{21}$, Nle$^{27}$, Asp$^{28}$]hGHRH(1-29)NH—CH$_3$;
P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27404 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;
P-27405 [N—Me-Tyr$^1$, Gln$^8$, Orn$^{12}$, Abu$^{15}$, Orn$^{21}$, Nle$^{27}$]hGHRH(1-29)NH—CH$_3$;
P-27406 [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$;
P-27407 [Dat$^1$, Gln$^8$, Orn$^{12}$, Abu$^{15}$, Orn$^{21}$, Nle$^{27}$, Asp$^{28}$]hGHRH(1-29)NH—CH$_3$;
P-27408 [Dat$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_3$;
P-27409 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;
P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$;
P-27411 [N—Me-Tyr$^1$, D-Ala$^2$, Thr$^8$, Orn$^{12}$, Abu$^{15}$, Orn$^{21}$, Nle$^{27}$]hGHRH(1-29)NH—CH$_3$;
P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$;
P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;
P-27414 [N—Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$;
P-27415 [N—Me-Tyr$^1$, Orn$^{12}$, Abu$^{15}$, Orn$^{21}$, Nle$^{27}$, Gab$^{30}$]hGHRH(1-30)NH—CH$_3$;
P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;
P-27417 [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27418 [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;
P-27419 [Ac-Tyr$^1$, Thr$^8$, Orn$^{12}$, Abu$^{15}$, Orn$^{21}$, Nle$^{27}$]hGHRH(1-29)NH—CH$_3$;

TABLE 1-continued

P-27422 27422 [N—Me-D-Tyr$^1$, Gln$^8$, Orn$^{12}$, Abu$^{15}$, Orn$^{21}$, Nle$^{27}$, Asp$^{28}$]hGHRH(1-29) NH—CH$_3$;
P-27423 [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;
P-27424 [Dat$^1$, Thr$^8$, Orn$^{12}$, Abu$^{15}$, Orn$^{21}$, Nle$^{27}$]hGHRH(1-29)NH—CH$_3$;
P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27440 [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27442 [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$;
P-27443 [N—Me-Tyr$^1$, Orn$^{12}$, Abu$^{15}$, Orn$^{21}$, Nle$^{27}$, D-Arg$^{29}$]hGHRH(1-29)NH—CH$_3$;
P-27444 [N—Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$;
P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27446 [N—Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27447 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_3$;
P-27448 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$;
P-27449 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$;
P-27450 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$;
P-27451 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_3$;
P-28420 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28421 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28430 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28431 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$;
P-28460 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28461 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28462 [N—Me-Tyr$^1$, D-Ala$^2$, Fpa5$^6$, Orn$^{12}$, Abu$^{15}$, Orn$^{21}$, Nle$^{27}$]hGHRH(1-29)NH—CH$_2$—CH$_3$;
P-28463 [N—Me-Tyr$^1$, D-Ala$^2$, Orn$^{12}$, Abu$^{15}$, Orn$^{21}$, Nle$^{27}$]hGHRH(1-29)NH—CH$_2$—CH$_3$;
P-28464 [N—Me-Tyr$^1$, D-Ala$^2$, Fpa5$^6$, Gln$^8$, Orn$^{12}$, Abu$^{15}$, Orn$^{21}$, Nle$^{27}$]hGHRH(1-29)NH—CH$_2$—CH$_3$;
P-28465 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28466 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;
P-28467 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28468 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28469 [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28470 [Dat$^1$, D-Ala$^2$, Orn$^{12}$, Abu$^{15}$, Orn$^{21}$, Nle$^{27}$]hGHRH(1-29)NH—CH$_2$—CH$_3$;
P-28471 [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$] hGHRH(1-29)NH—CH$_2$—CH$_3$;
P-28473 [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;
P-28474 [Dat$^1$, D-Ala$^2$, Orn$^{12}$, Abu$^{15}$, Orn$^{21}$, Nle$^{27}$, Asp$^{28}$] hGHRH(1-29)NH—CH$_2$—CH$_3$;
P-28475 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$;
P-28476 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$;
P-28477 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$;
P-28478 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$;
P-28479 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$] hGHRH(1-30)NH—CH$_2$—CH$_3$;
P-29701 [N—Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$]hGHRH](1-30)NH$_2$;
P-29702 [Dat$^1$, D-Ala$^2$, Orn$^{12}$, Abu$^{15}$, Orn$^{21}$, Nle$^{27}$, Gln-Gab$^{30}$]hGHRH(1-30)NH$_2$;
P-29703 [N—Me-Tyr$^1$, Gln$^8$, Orn$^{12}$, Abu$^{15}$, Orn$^{21}$, Nle$^{27}$, Gln-Gab$^{30}$]hGHRH(1-30)NH$_2$;
P-29704 [Dat$^1$, D-Ala$^2$, Gln$^8$, Orn$^{12}$, Abu$^{15}$, Orn$^{21,22}$, Nle$^{27}$, Gln-Gab$^{30}$]hGHRH(1-30)NH$_2$;
P-29706 [Tfa-Tyr$^1$, D-Abu$^2$, Gln$^8$, Orn$^{12}$, Abu$^{15}$, Orn$^{21}$, Nle$^{27}$, Gln-Gab$^{30}$]hGHRH(1-30)NH$_2$;
P-29708 [N—Me-Tyr$^1$, D-Ala$^2$, Fpa5$^6$, Orn$^{12}$, Abu$^{15}$, Orn$^{21}$, Nle$^{27}$, Gln-Gab$^{30}$]hGHRH(1-30)NH$_2$;

TABLE 1-continued

P-29710 [N—Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$;

P-29720 [Dat$^1$, D-Ala$^2$, Orn$^{12}$, Abu$^{15}$, Orn$^{21}$, Nle$^{27}$, Asp$^{28}$, Gln-Gab$^{30}$]hGHRH(1-30)NH$_2$;

P-29721 [Dat$^1$, D-Ala$^2$, Gln$^8$, Orn$^{12}$, Abu$^{15}$, Orn$^{2122}$, Nle$^{27}$, Asp$^{28}$, Gln-Gab$^{30}$]hGHRH(1-30) NH$_2$;

P-29722 [Tfa-Tyr$^1$, D-Abu$^2$, Gln$^8$, Orn$^{12}$, Abu$^{15}$, Orn$^{21}$, Nle$^{27}$, Asp$^{28}$, Gln$^{30}$, Gab$^{31}$]hGHRH(1-30)NH$_2$;

P-29723 [N—Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$] hGHRH (1-30)NH$_2$; and P-29724 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln Gab$^{30}$] hGHRH(1-30)NH$_2$;

Overview of Synthesis

The peptides may be synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, Ill., 1984 (2nd. ed.), and M. Bodanszky, "Principles of Peptide Synthesis", Springer Verlag, 1984. The hGHRH agonist peptides are preferably prepared using solid phase synthesis, such as that generally described by Merrifield, J. Am. Chem. Soc, 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group. In certain cases, protected omega-amino acids are also used during the synthesis. Boc or Fmoc protecting groups are also appropriate for the protection of omega-amino groups.

In solid phase synthesis, the N-alpha-protected or N-omega-protected amino acid moiety which forms the aminoacyl group of the final peptide at the C-terminus is attached to a polymeric resin support via a chemical link. After completion of the coupling reaction, the alpha (or omega) amino protecting group is selectively removed to allow subsequent coupling reactions to take place at the amino-terminus, preferably with 50% TFA in DCM when the N-alpha-(N-omega-) protecting group is Boc, or by 20% piperidine in DMF when the N-alpha-(N-omega-) protecting group is Fmoc. The remaining amino acids with similarly Boc or Fmoc-protected alpha (or omega) amino groups are coupled stepwise to the free amino group of the preceding amino acid on the resin to obtain the desired peptide sequence. Because the amino acid residues are coupled to the alpha (or omega) amino group of the C-terminus residue, growth of the synthetic hGHRH analogue peptides begins at the C terminus and progress towards the N-terminus. When the desired sequence has been obtained, the peptide is acylated, or the amino group is left free at the N-terminus, and the peptide is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha (or omega) amino protecting group prior to the coupling of the next amino acid.

Typical synthesis cycles are shown in Table 2 and Table 3.

TABLE 2

PROTOCOL FOR A TYPICAL SYNTHETIC CYCLE USINQ BOC-STRATEQY

| Step | Reagent | Mixing Time (min) |
|---|---|---|
| 1. Deprotection | 50% TFA in DCM | 5 + 25 |
|  | DCM wash | 1 |
|  | 2-propanol wash | 1 |
| 2. Neutralization | 5% DIEA in DCM | 1 |
|  | DCM wash | 1 |
|  | MeOH wash | 1 |
|  | 5% DIEA in DCM | 3 |
|  | MeOH wash | 1 |
|  | DCM wash (3 times) | 1 |
| 3. Coupling | 3 eq. Boc-amino acid in DCM or DMF + 3 eq. DIC or the preformed HOBt ester of the Boc-amino acid | 60 |
|  | MeOH wash (3 times) | 1 |
|  | DCM wash (3 times) | 1 |
| 4. Acetylation (if appropriate) | Ac$_2$O in pyridine (30%) | 10 + 20 |
|  | MeOH wash (3 times) | 1 |
|  | DCM wash (3 times) | 1 |

TABLE 3

PROTOCOL FOR A TYPICAL SYNTHETIC CYCLE USING FMOC-STRATEQY

| Step | Reagent | Time |
|---|---|---|
| 1. Deprotection | 20% piperidine in DMF | 5 + 15 |
|  | DMF wash (3 times) | 1 |
| 2. Coupling | 3 eq. Fmoc-amino acid in DMF 3 eq. DIC or +3 eq.HBTU + 3 eq. HOBt + 6 eq.DIEA | 60 |
|  | DMF wash (3 times) | 1 |
| 3. Acetylation (if appropriate) | 3 eq. 1-acetyl imidazole in DMF | 30 |
|  | DMF wash (3 times) | 1 |

After completion of the synthesis, the cleavage of the peptide from the resin can be effected using procedures well known in peptide chemistry.

Choice of Support Polymer

The hGHRH agonist peptides may be synthesized on a variety of support polymers, i.e. MBHA, Merrifield, PAM, Rink amide or Wang resins. The peptides can also be synthesized on aminomethyl, MBHA, or other resins that have been previously derivatized with suitable linkers. Examples of such linkers are the base-labile 4-hydroxymethyl benzoic acid (HMBA) linker for the attachment of C-terminal carboxyl groups, the acid-labile para-sulfonylphenoxyacetyl (SPA) linker which permits the attachment of agmatine through its guanidino group, or the acid-labile

[3-[(Methyl-Fmoc-amino)methyl]-indol-1-yl]-acetyl linker which allows the synthesis of peptides with C-terminal methylamide (—NH—CH$_3$).

When peptides with an amidated C-terminus are synthesized by using Boc strategy, the preferred resin is MBHA. Attachment of the C-terminal amino acid to this resin can be accomplished by the standard DIC-mediated coupling method described in Table 2.

In order to prepare peptides with C-terminal methylamide (—NH—CH$_3$) or ethylamide (—NH—CH$_2$—CH$_3$) modification, two methods can be used: a) the Merrifield resin is loaded with the Boc-protected C-terminal amino acid by coupling mediated by potassium fluoride (KF) or cesium salt at elevated temperature; b) [3-[(Methyl-Fmoc-amino)methyl]-indol-1-yl]-acetylAm or 3-[(Ethyl-Fmoc-amino)methyl]-indol-1-yl]-acetyl Am resins may be used, respectively for the synthesis of peptides having C-terminal methylamide (—NH—CH$_3$) or ethylamide (—NH—CH$_2$—CH$_3$) modification. When using these resins, the Fmoc protecting group can be removed from the resin with the methods described in Table 3 before the synthesis.

For the synthesis of peptides having Agm at the C-terminus, two methods may be used. In one embodiment, the support phase is MBHA resin or an aminomethyl resin, and the guanidino group of Boc-Agm is joined to the support polymer through a stable, but readily cleavable linker such as the para-sulfonyl-phenoxyacetyl (SPA) moiety. The alpha-amino-Boc-protected Agm is reacted with the chlorosulfonyl phenoxyacetic acid Cl-SO$_2$—C$_6$H$_4$—O—CH$_2$—COOH to form Boc-Agm-SO$_2$—C$_6$H$_4$—O—CH$_2$—COOH. This compound is then coupled to the support polymer e.g. to MBHA resin using DIC or HBTU-HOBt-DIEA as activating reagent to yield Boc-Agm-SPA-MBHA. In another embodiment, Agm-SO$_2$—PS resin may be used for the synthesis (1% DVB, 100-200 mesh, 2.5 mmol/g, Advanced ChemTech (Louisville, Ky.)) at pH 10-13 to form Boc-Agm-SO$_2$-resin.

Amino Acid Derivatives Used

Bifunctional amino acids, i.e. those not having side chain functional groups, are mostly used in the form of their N-alpha Boc- or Fmoc-derivatives for synthesis. Bifunctional omega-amino acids are also typically used in the form of their N-omega Boc- or Fmoc-derivatives. Thus, Boc-Gly-OH or Fmoc-Gly-OH is typically used for incorporating the Gly residue. The naturally occurring bifunctional amino acids are Gly, Ala, Val, Leu, Ile, Phe, and Pro, and some well-known non-coded bifunctional amino acids used in this invention are Abu, Aib, Gab, Nle, Aah, and Aap.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the coupling reactions.

The following general rules may be followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

When Boc-amino acids are used in the synthesis, the reactive side chain functional groups can be protected as follows: Tos or nitro (NO$_2$) for Arg and Har; cHx or Fm for Asp and Glu; Bom for His; 2ClZ or Fmoc for Lys and Orn; Bzl for Ser and Thr; and 2BrZ for Tyr. The side chains of Asn and Gln are unprotected.

In the case of Fmoc synthesis, the reactive side chain functional groups can be protected by other appropriate protective groups as follows: 2,2,4,6,7-pentamethyl-dihydrobenzofurane-5-sulfonyl (Pbf), 4-methoxy-2,3,6-trimethyl benzenesulphonyl (Mtr), or bis-Boc for Arg and Har; tert-butyl (Bul) for Asp and Glu; no protective group or trityl (Trt) protection for Asn and Gln; Trt for His; Boc or 4-methoxytrityl (Mmt) for Lys and Orn; tBu or Trt for Ser and Thr; and tBu or 2-chlorotrityl (2ClTrt) for Tyr. In addition to the widely known coded and non-coded amino acids mentioned above, some of the peptides of this application contain less common non-coded amino acids such as homoarginine (Har); ornithine (Orn); N-methyl-alanine [N-Me-Ala]; N-methyl-tyrosine [N-Me-Tyr]; pentafluorophenylalanine [Phe(F)5, Fpa5]. These amino acid residues are incorporated into the peptides by coupling the suitable protected amino acid derivatives. A non-exclusive list of such protected amino acid derivatives that can be used is as follows: Boc-Har(Tos)-OH, Boc-Orn(2ClZ)—OH, Boc-N-Me-Ala-OH, Boc-N-Me-Tyr(2BrZ)—OH, Boc-Fpa5-OH, Fmoc-Har(Pbf)-OH, Fmoc-Orn(Boc)-OH, Fmoc-N-Me-Ala-OH, and Fmoc-N-Me-Tyr(2ClTrt)-OH. The protected derivatives of noncoded amino acids mentioned above are commonly available from several commercial suppliers, including Novabiochem (San Diego, Calif.), Advanced ChemTech (Louisville, Ky.), Bachem (King of Prussia, Pa.), Peptides International (Louisville, Ky.), RSP Amino Acid Analogues DBA (Worcester, Mass.), and AnaSpec (San Jose, Calif.).

Stepwise Coupling of Amino Acid Residues

Utilizing the above mentioned support polymers and after loading of the protected C-terminal amino acid or Agm residue, the peptide itself may suitably be built up by solid phase synthesis in the conventional manner. Each protected amino acid is coupled in about a three-fold molar excess, with respect to resin-bound free amino residues, and the coupling may be carried out in a medium such as DMF-DCM (1:1) or in DMF or DCM alone. The selection of an appropriate coupling reagent is within the skill of the art. Particularly suitable as coupling reagents are N,N'-diisopropyl carbodiimide (DIC), or HBTU combined with HOBt in the presence of DIEA. The success of the coupling reaction at each stage of the synthesis is preferably monitored by the ninhydrin reaction. In cases where incomplete coupling occurs, either the coupling procedure is repeated, or the resin-bound unreacted amino residues are acetylated using a capping reagent, before removal of the alpha (or omega) amino protecting group. Suitable capping reagents are 1-acetylimidazole and Ac$_2$O in pyridine.

Cleavage of the Peptide from the Support Polymer and Removal of the Side-Chain Protecting Groups When the synthesis is complete, the peptide is cleaved from the support phase and its side-chain protecting groups are removed.

In cases where peptides with an amidated C-terminus (—CONH$_2$) or with a C-terminal carboxyl group (—COOH) are prepared by Boc strategy on an MBHA, Merrifield, or PAM resin, the removal of the peptide from the resin is performed by treatment with a reagent such as liquid hydrogen fluoride (HF). This is also the case for peptides synthesized on the Boc-Agm-SPA-MBHA or Bos-Agm-tosyl-resin. In some instances, the liquid HF also cleaves all the remaining side chain protecting groups. However, if side chain protecting groups resistant to HF treatment are present on the peptide, additional cleavage steps should be performed in order to remove these protecting groups. Thus, Fm and Fmoc protecting groups are removed by treatment with 20% piperidine in DMF, prior to or after the HF treatment.

Suitably, the dried and protected peptide-resin is treated with a mixture consisting of 1.0 mL m-cresol and 10 mL anhydrous hydrogen fluoride per gram of peptide-resin for 60-120 min at 0° C. to cleave the peptide from the resin as well as to remove the HF-labile side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

In cases where peptides with a methyl- (—NH—CH3), or ethyl-amide (—NH—CH$_2$—CH$_3$) C-terminus are prepared by Boc strategy on the Merrifield or HMBA-MBHA resin, the protected peptides are first cleaved from the resin by methylamine (CH$_3$NH$_2$) or ethylamine (CH$_3$CH$_2$NH$_2$) mediated aminolysis. Suitably, liquid CH$_3$NH$_2$ or CH$_3$CH$_2$NH$_2$ is transferred into a cooled, heavy-walled glass flask that contains the dried and protected peptide-resin. The quantity of liquid CH$_3$NH$_2$ or CH$_3$CH$_2$NH$_2$ should be sufficient to cover the peptide-resin. The flask is stoppered, and shaken with the liquid CH$_3$NH$_2$ or CH$_3$CH$_2$NH$_2$ for 3.5 hours at room temperature in order to allow for the reaction to take place. After this, the flask is cooled in a dry ice bath, opened, and the liquid CH$_3$NH$_2$ or CH$_3$CH$_2$NH$_2$ is filtered off the solid residue that contains a mixture of resin and cleaved peptide, the peptide still having the protecting groups attached. The solid residue is dried and subjected to HF treatment as described above, in order to remove the side chain protecting groups of the peptide.

In cases when peptides with a methyl- (—NH—CH$_3$), or ethyl-amide (—NH—CH$_2$—CH$_3$) C-terminus are prepared by Fmoc strategy on [3-[(Methyl-Fmoc-amino)methyl]-30 indol-1-yl]-acetyl AM or 3-[(Ethyl-Fmoc-amino)methyl]-indol-1-yl]-acetyl AM resins, respectively, the protected peptides are cleaved from the resin with a cleavage cocktail. Since no single cleavage and deprotection procedure is optimal for all peptides due to the nature of the linker and the amino acid composition of the peptide, the following cleavage cocktail proved to be the most suitable for cleavage and deprotection of GHRH agonists: 94% TFA, 3% H$_2$O, 1.5% m-cresol, and 1.5% phenol. Cleavage cocktail must be prepared fresh and have to use high quality TFA and scavengers. The amount of cleavage cocktail used depends on both the amount of the peptide-resin and its properties. Enough cocktail solution should be used to saturate and swell the resin during the reaction, with about 2-3 mm of clear solution below the floating beads. Generally 5 mL of cleavage cocktail is used for 0.5 g of resin. The choice of reaction time depends on the linker and the side-chain protecting groups of the peptide. Preferably, 3-hour reaction time is used for the cleavage and deprotection of GHRH agonists. To induce peptide precipitation, the cleavage mixture is added dropwise to cold (preferably −20° C.) ether. The non-peptide products remain in the ether solution. The precipitated material is collected by filtration or centrifugation and is washed three times with cold ether to remove any residual scavengers. The cleaved and deprotected peptide is dissolved in 50% acetic acid and separated from the resin by filtration and, after dilution with water, the solution is lyophilized.

Purification

The purification of the crude peptides can be effected using procedures well known in peptide chemistry. For example, purification may be performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0 using an XBridge Prep OBD™ reversed phase column (4.6×250 mm, packed with C$_{18}$ silica gel, 300 A pore size, 5 82 m particle size) (Waters Co., Milford, Mass.). The column is eluted with a solvent system consisting of (A) 0.1% aqueous TFA and (B) 0.1% TFA in 70% aqueous MeCN in a linear gradient mode (e.g., 30-55% B in 120 min); flow rate of 12 mL/min. The eluent is monitored at 220 nm, and fractions are examined by analytical HPLC using a Hewlett-Packard Model HP-1090 liquid chromatograph and pooled to give maximum purity. Analytical HPLC is carried out on a Supelco Discovery HS C18 reversed-phase column (2.1×50 mm, C18, 300 A pore size, 3 µm particle size) (Supelco, Bellefonte, Pa.) using isocratic elution with a solvent system consisting of (A) and (B) defined above with a flow rate of 0.2 mL/min. The peaks are monitored at 220 and 280 nm. The peptides are judged to be substantially (>95%) pure by analytical HPLC. Molecular masses are checked by electrospray mass spectrometry (Agilent Technologies 6210 Time-of-Light LC/MS, Santa Clara, Calif.) and the expected amino acid compositions are confirmed by amino acid analysis.

Methods

In some embodiments, the GHRH peptides and agonists described herein may be administered to a subject in need for treating reperfusion injury. The reperfusion injury may be due to ischemia or hypoxia.

In some embodiments, the GHRH agonists may be used to treat ischemia. Ischemia may be an absolute or relative shortage of blood supply to a body component. Relative shortage may be a mismatch, however small, of blood supplied (oxygen delivery) to a body component vs. blood required to a body component for the adequate oxygenation. Ischemia may also be an inadequate flow of blood to a part of the body due to a constriction or blockage of blood vessels supplying it and may affect any body component in the body. Insufficient blood supply causes body components to become hypoxic, or, if no oxygen is supplied at all, anoxic. This may cause necrosis. The mechanisms of ischemia may vary greatly. For example, ischemia to any body component may be due to tachycardia (abnormally rapid beating of the heart), atherosclerosis (lipid-laden plaque obstructing the lumen of arteries), hypotension (low blood pressure in septic shock, heart failure), thromboembolisms (blood clots), outside compression of blood vessels (tumor), embolisms (foreign bodies in the circulation, e.g., amniontic fluid embolism), sickle cell disease (abnormally shaped hemoglobin), infarctions, induced g-forces which restrict the blood flow and force the blood to extremities of the body, localized extreme cold due to frostbite, ice, improper cold compression therapy, and any other force that restricts blood flow to the extremities such as a tourniquet. Force to restrict blood flow to extremities may be required due to severe lacerations, incisions, puncture such as a knifing, crushing injuries due to blunt force trauma, and ballistic trauma due to gunshot or shrapnel wounds. Ischemia may be a feature of heart diseases, ischemic colitis, transient ischemia attacks, cerebrovascular accidents, acute renal injury, ruptured arteriovenous malformations, and peripheral artery occlusive disease. Ischemia may also result due to cardiovascular disease, cardiomyopathy, myocardial stunning, peripheral vascular disease, intermittent claudication, ischemia-reperfusion, myocardial infarction, cardiac fibrosis, cardiac weakness, acute renal failure, stroke, thromboembolism (blood clot), sickle cell disease, localized pressure to extremities to the body, and tumors. The GHRH agonists may also be administered to patients to treat ischemia during or post heart surgery, organ transplantation, angioplasty and stenting. In some embodiments, the method comprises administering at least one GHRH agonist peptide, or a combination of GHRH agonist peptides to achieve the desired effect.

In some embodiments, the GHRH agonists may be used to treat hypoxia. Hypoxia may be a deprivation of adequate supply of oxygen. Hypoxia may be pathological condition in which the body as a whole (generalized hypoxia) or region of the body (tissue hypoxia) is deprived of adequate oxygen supply. A variation in levels of arterial oxygen may be due to a mismatch between supply and demand of oxygen by body components. A complete deprivation of oxygen supply is anoxia. Hypoxia may be hypoxemic hypoxia, anemic hypoxia, hypoxemic hypoxia, histotoxic hypoxia, histotoxic hypoxia, and ischemic hypoxia. In some embodiments, the method comprises administering at least one GHRH agonist peptide, or a combination of GHRH agonist peptides to achieve the desired effect.

The GHRH agonists described herein may also be used for promoting differentiation of mesenchymal stem cells into endothelial cells in vitro. The mesenchymal cells may be in suspension or adhered to cell culture dishes or any other substrate. In some embodiments, the GHRH agonists may also be used for promoting differentiation of mesenchymal stem cells into endothelial cells in vivo by administering a therapeutically effective amount of at least one agonist of GHRH to the subject. The GHRH agonists may also be used in promoting differentiation of mesenchymal stem cells into endothelial cells in animal models, such as rodents and primates. In some embodiments, the method comprises administering at least one GHRH agonist peptide, or a combination of GHRH agonist peptides to achieve the desired effect.

The GHRH agonists of the present invention may be used for controlling all type of blood vessel development, e.g., vasculogenesis, angiogenesis and the differentiation of endothelial cells from pluripotent stem cells. For example, the GHRH agonists described herein are useful for targeting all aspects of blood vessel development, from early endothelial cell differentiation to angiogenesis. In addition, the GHRH agonists of the present invention may also be used for therapeutic role in modulating endothelial cell differentiation. For example, circulating stem cells, which are capable of differentiating into endothelial cells can migrate into regions of the body where angiogenesis and/or vasculogenesis occurs. Similarly, angiogenesis can be increased by increasing the differentiation of these migrating stem cells into endothelial cells. In some embodiments, the GHRH peptides may be used for promoting vasculogenesis in a mammal may involve administering a therapeutically effective amount of growth hormone releasing hormone (GHRH) and/or at least one agonist of GHRH to the subject. In addition, the GHRH peptides may also be used for promoting vasculogenesis in in vitro setting or other experimental models. In some embodiments, the method comprises administering at least one GHRH agonist peptide, or a combination of GHRH agonist peptides to achieve the desired effect.

The GHRH agonists of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred agonists are salts of low solubility, e.g., pamoate salts and the like. These exhibit long duration of activity.

Formulations containing the GHRH agonists of the present invention and a suitable carrier can be solid dosage forms which include, but are not limited to, softgels, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. In some embodiments, a single dose may comprise one or more softgels, tablets, capsules, cachets, pellets, pills, or the like. Specific examples include, for example, a dose comprising 1, 2, 3, or 4 softgels, tablets, capsules, cachets, pellets, pills or the like.

In some embodiments, one or more softgels, tablets, capsules, cachets, pellets, pills, or the like can be taken to achieve the desired dosing. In some embodiments, one or more softgels, tablets, capsules, cachets, pellets, pills, or the like can be taken simultaneously to achieve the desired dosing. In yet another embodiment one or more softgels, tablets, capsules, cachets, pellets, pills, or the like can be taken separately during the course of a specified time period such as for example, a 24 hour period. For example, one or more softgels, tablets, capsules, cachets, pellets, pills, or the like can be taken twice in a 24 hour period to achieve the desired dose. In some embodiments, one or more softgels, tablets, capsules, cachets, pellets, pills, or the like can be taken with a meal. For example one or more softgels, tablets, capsules, cachets, pellets, pills, or the like can be taken with each meal during the course of a 24 hour period to achieve the desired dose.

It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and Goodman & Gilman's *The Pharmaceutical Basis of Therapeutics,* 6th Edition, MacMillan Publishing Co., New York (1980) can be consulted.

In some embodiments, the pharmaceutical excipient may include, without limitation, binders, coating, disintegrants, fillers, diluents, flavors, colors, lubricants, glidants, preservatives, sorbents, sweeteners, conjugated linoleic acid (CLA), gelatin, beeswax, purified water, glycerol, any type of oil, including, without limitation, fish oil or soybean oil, or the like. Pharmaceutical compositions of the peptides/compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The peptides/compounds of the present invention can be administered in the conventional manner by any route where they are active. Administration can be systemic, parenteral, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the peptides/compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Alternatively, the GHRH agonists may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed agonistic compounds.

Specific modes of administration will depend on the indication. The selection of the specific route of administration and the dose regimen is to be adjusted or titrated by the clinician according to methods known to the clinician in order to obtain the optimal clinical response. The amount of compounds to be administered is that amount which is therapeutically effective. The dosage to be administered will depend on the characteristics of the subject being treated, e.g., the particular animal or human being treated, age, weight, health, types of concurrent treatment, if any, and frequency of treatments, and can be easily determined by one of skill in the art (e.g., by the clinician).

The amount of GHRH agonists needed depends on the type of pharmaceutical composition and on the mode of administration. In cases where human subjects receive solutions of GHRH agonists, administered by i.m. or s.c. injection, or in the form of intranasal spray or pulmonary inhalation, the typical doses are between 2-20 mg/day/patient, given once a day or divided into 2-4 administrations/day. When the GHRH agonists are administered intravenously to human patients, typical doses are in the range of 8-80 ug/kg of body weight/day, divided into 1-4 bolus injections/day or given as a continuous infusion. When depot preparations of the GHRH agonists are used, e.g. by i.m. injection of pamoate salts or other salts of low solubility, or by i.m. 10 or s.c. administration of microcapsules, microgranules, or implants containing the agonistic compounds dispersed in a biodegradable polymer, the typical doses are between 1-10 mg agonist/day/patient.

The GHRH agonists of the present invention can be formulated for parenteral administration by injection, e.g., by bolus injection or continuous infusion. The peptides/compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the GHRH agonists can be formulated readily by combining these peptides/compounds with pharmaceutically acceptable carriers well known in the art. Such carriers enable the peptides/compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores.

Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active peptides/compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active peptides/compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the peptides/compound and a suitable powder base such as lactose or starch.

The compositions of the present invention can also be formulated in rectal compositions such as suppositories or retention enemas, e.g., containing conventional suppository bases such as cocoa butter or other glycerides.

In addition to the formulations described previously, the compositions of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the peptides/compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions of the present invention, for example, can be applied to a plaster, or can be applied by transdermal, therapeutic systems that are consequently supplied to the organism.

The compositions of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

This invention and embodiments illustrating the method and materials used may be further understood by reference to the following non-limiting examples. The present invention is described in connection with the following examples which are set forth for the purposes of illustration only. In the examples, optically active protected amino acids in the L-configuration are used except where specifically noted. The following Examples set forth suitable methods of synthesizing the novel GHRH agonists by the solid-phase technique.

EXAMPLES

Example 1

Synthesis of N-Me-Tyr$^1$-Ala$^2$-Asp$^3$-Ala$^4$-Ile$^5$-Fpa5$^6$-Thr$^7$-Gln$^8$-Ser$^9$-Tyr$^{10}$-Arg$^{11}$-Orn$^{12}$-Var$^3$-Leo$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Agm$^{29}$ or [N-Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH (1-29) (Peptide 20103)

The synthesis is conducted in a stepwise manner using manual solid phase peptide synthesis equipment. Two methods have been used for the synthesis of peptides having Agm at the C-terminus. In one case, the starting material of the synthesis is Boc-agmatine-NG-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin is well known in the art. Briefly, Boc-Agm-SPA-MBHA resin (1.67 g, 0.50 mmol) is pre-swollen in DCM and then the deprotection and neutralization protocols described in Table 2 are performed in order to remove the Boc protecting group and prepare the peptide-resin for coupling of the next amino acid. In another case, Agm-sulfonyl-polystyrene (PS) resin is used [1% DVB, 100-200 mesh, 0.74 mmol/g, American Peptide Company (Sunnyvale, Calif.)]. Briefly, Agm-sulfonyl-PS resin (680 mg, 0.50 mmol) is neutralized with 5% DIEA in DCM and washed according to the protocol described in Table 2. The solution of Boc-Asp(OcHx)-OH (475 mg, 1.5 mmol) in DMF-DCM (1:1) is shaken with the neutralized resin and DIC (235 µl, 1.5 mmol) in a manual solid phase peptide synthesis apparatus for 1 hour. Then, the deprotection and neutralization protocols described in Table 2 are performed in order to remove the Boc protecting group and prepare the peptide-resin for coupling of the next amino acid. The synthesis is continued in a stepwise manner using manual solid phase peptide synthesis equipment in both cases, and the peptide chain is built stepwise by coupling the following protected amino acids in the indicated order on the resin to obtain the desired peptide sequence: Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)—OH.

These protected amino acid residues (also commonly available from NovaBiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 ul, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 68 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 A pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 68 mg of crude peptide is dissolved in AcOH/H$_2$O, stirred, filtered and applied on an XBridge Prep OBD™ reversed phase column (4.6×250 mm, packed with C$_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 18 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 20105, Peptide 20107, Peptide 20109, Peptide 20110, Peptide 20111, Peptide 20113, Peptide 20115, Peptide 20350, Peptide 20351, Peptide 20356, Peptide 20357, Peptide 20358, Peptide 20359, Peptide 20360, Peptide 20361, Peptide 20363, Peptide 20367, Peptide 20370, Peptide 20371, Peptide 20372, Peptide 20373, Peptide 20374, Peptide 20375, Peptide 20376, are synthesized in the same manner as Peptide 20103, except that these peptides also contain other amino acid substitutions in the peptide sequence, and acyl moieties at their N-termini. The details for these syntheses are set forth below.

For the synthesis of Peptide 20105, the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20107, the chemical structure of which is [[N-Me-Tyr1, Fpa5$^6$, Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 20109, the chemical structure of which is [N-Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20110, the chemical structure of which is [N-Me-Tyr$^1$, D-Ala$^2$, Fpa5$^6$, OM$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20111, the chemical structure of which is [N-Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20113, the chemical structure of which is [N-Me-Tyr$^1$, Fpa5$^6$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20115, the chemical structure of which is [N-Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH(1-29) the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 20117 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20350 the chemical structure of which is [Dat$^1$, D-Ala$^2$, Gln$^8$, Orn$^{12}$, Abu$^{15}$, Orn$^{21}$, Nle$^{27}$, Asp$^{28}$, Agm$^{29}$]liGHRH(1-29), the following protected amino acids are coupled in the indicated order on the resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 20351 the chemical structure of which [Ac-N-Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Ac-N-Me-Tyr(2BrZ)—OH.

For the synthesis of Peptide 20356, the chemical structure of which [N-Me-Tyr$^1$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20357 the chemical structure of which [Dat$^1$, D-Ala$^2$, N-Me-Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-N-Me-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 20358 the chemical structure of which [Dat$^1$, D-Ala$^2$, N-Me-Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-N-Me-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20359, the chemical structure of which is [N-Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20360, the chemical structure of which is [N-Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20361, the chemical structure of which is [N-Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20367, the chemical structure of which is [N-Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20370, the chemical structure of which is [N-Me-Tyr$^1$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 20371, the chemical structure of which is [N-Me-Tyr$^1$, Thr$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20372, the chemical structure of which is [N-Me-Tyr$^1$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20373, the chemical structure of which is [N-Me-Tyr$^1$, Gln$^8$, Orn$^{12}$, Abu$^{15}$, Orn$^{21}$, Nle$^{27}$, Agm$^{29}$]hGHRH(1-29), the following protected amino acids are coupled in the indicated order on the Agm-SO2-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 20374, the chemical structure of which is [N-Me-Tyr$^1$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 20375, the chemical structure of which is [N-Me-Tyr$^1$, Thr$^8$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 20376, the chemical structure of which is [N-Me-Tyr$^1$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

HF cleavage and deprotection, and subsequent purification by semipreparative HPLC of Peptide 20105, Peptide 20107, Peptide 20109, Peptide 20110, Peptide 20111, Peptide 20113, Peptide 20115, Peptide 20350, Peptide 20351, Peptide 20356, Peptide 357, Peptide 20358, Peptide 20359, Peptide 20360, Peptide 20361, Peptide 20363, Peptide 20367, Peptide 20370, Peptide 20371, Peptide 20372, Peptide 20373, Peptide 20374, Peptide 20375, Peptide 20376 are done as described in the case of Peptide 20103. The purified compounds are judged to be substantially (>95%) pure by analytical HPLC. Their molecular masses are checked by electrospray mass spectrometry, and the expected amino acid compositions are confirmed by amino acid analysis.

Example 2

Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Gln$^{24}$-Asp$^{25}$-Ile$^{26}$-Nle$^{27}$-Asp$^{28}$-Arg$^{29}$-Amc$^{30}$-NH$_2$ (Peptide 21300)[Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$. The synthesis is conducted in a stepwise manner using manual solid phase peptide synthesis equipment. Briefly, para-methylbenzhydrylamine (MBHA) resin (100-200 mesh, 1% DVB, 0.7 mmol/g, Advanced Chemtech, Louisville, Ky.) (350 mg, 0.50 mmol) is neutralized with 5% DIEA in DCM and washed according to the protocol described in Table 2. The solution of Boc-Amc-OH (390 mg, 1.5 mmol) in DMF-DCM (1:1) is shaken with the neutralized MBHA resin and DIC (235 µl, 1.5 mmol) in a manual solid phase peptide synthesis apparatus for 1 hour. After the completion of the coupling reaction is proved by negative ninhydrin test, the deprotection and neutralization protocols described in Table 2 are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free. The protected amino acids (1.5 mmol each) are coupled with DIC (235 µL, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 130 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with $C_{18}$ silica gel, 300 A pore size, 3 μm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 130 mg of crude peptide is dissolved in AcOH/H$_2$O, stirred, filtered and applied on an XBridge Prep OBD™ reversed phase column (4.6×250 mm, packed with $C_{18}$ silica gel, 300 A pore size, 5 μm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 28 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 21301, Peptide 21303, Peptide 21304, Peptide 21305, Peptide 21306, Peptide 21307, Peptide 21308, Peptide 21309, Peptide 21310, Peptide 21311, Peptide 22325, Peptide 22326, Peptide 22327, Peptide 22328, Peptide 22329, Peptide 22330, Peptide 22331, Peptide 22332, Peptide 22334, Peptide 22335, Peptide 22336, Peptide 22337, Peptide 23250, Peptide 23251, Peptide 23252, Peptide 23253, Peptide 23254, Peptide 23255, Peptide 23256, Peptide 23257, Peptide 23258, Peptide 23259, Peptide 23260, Peptide 23261, Peptide 23262, Peptide 23263, Peptide 23264, Peptide 23265, Peptide 24340, Peptide 24341, Peptide 24342, Peptide 24344, Peptide 24345, Peptide 24346, Peptide 24347, Peptide 24348, Peptide 25501, Peptide 25502, Peptide 25503, Peptide 25504, Peptide 25506, Peptide 25508, Peptide 25516, Peptide 26802, Peptide 26803, Peptide 2680,are synthesized in the same manner as Peptide 20300, except that these peptides also contain other amino acid substitutions in the peptide sequence, and/or different alpha- or omega-amino acid moieties at their C-termini. The details for these syntheses are set forth below.

For the synthesis of Peptide 21301, the chemical structure of which [N-Me-Tyr$^1$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 21303, the chemical structure of which [N-Me-Tyr$^1$, D-Ala$^2$, Orn$^{12}$, Abu$^{15}$, Orn$^{21}$, Nle$^{27}$, Asp$^{28}$, Ame$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 21304, the chemical structure of which [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21305, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 21306, the chemical structure of which [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$), the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21307, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg (Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 21308, the chemical structure of which [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21309, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_{25}$ the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 21310, the chemical structure of which [Dat$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-His(Bom)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21311, the chemical structure of which [N-Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-His(Bom)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 22325, the chemical structure of which [N-Me-Tyr$^1$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 22326, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 22327, the chemical structure of which [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 22328, the chemical structure of which [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Ac-Tyr(2BrZ)—OH.

For the synthesis of Peptide 22329, the chemical structure of which [N-Me-Tyr$^1$, D-Ala$^2$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 22330, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-

OH, Boc-Gln-OH, Boc-Leu-OH, Boc-Leu-OH, Boc-Orn (2ClZ)—OH, Boc-Arg(Tos)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)—OH, Boc-Arg (Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 22331, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)—OH, Boc-Arg(Tos)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)—OH, Boc-Arg (Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 22332, the chemical structure of which [N-Me-Tyr$^1$, Orn$^{12}$, Abu$^{15}$, Orn$^{21}$, Nle$^{27}$, Asp$^2$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr (2BrZ)—OH, Boc-Ser(Bzl)-OH, Boc-Asn-OH, Boc-Thr (Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 22334, the chemical structure of which [N-Me-Tyr$^1$, Orn$^{12}$, Abu$^{15}$, Orn$^{21}$, Nle$^{27}$, Apa$^{30}$]hGHRH(1-30)NH$_2$, the following protected amino acids are coupled in the indicated order on the MBHA resin: Boc-Apa-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg (Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr (2BrZ)—OH, Boc-Ser(Bzl)-OH, Boc-Asn-OH, Boc-Thr (Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 22335 the chemical structure of which [N-Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 22336 the chemical structure of which [N-Me-Tyr$^1$, Ala$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 22337 the chemical structure of which [N-Me-Tyr$^1$, D-Ala$^2$, Cpa$^6$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)—OH, Boc-Arg(Tos)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)—OH, Boc-Arg (Tos)-OH, Boc-Tyr(2BrZ)—OH, Boc-Ser(Bzl)-OH, Boc-Ala-OH, Boc-Thr(Bzl)-OH, Boc-Cpa-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 23250, the chemical structure of which [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)—OH, Boc-Arg(Tos)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)—OH, Boc-Arg (Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23251, the chemical structure of which [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23252, the chemical structure of which [Dat$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23253, the chemical structure of which [Dat$^1$, Orn$^{12}$, Abu$^{15}$, Orn$^{21}$, Nle$^{27}$, Asp$^{28}$, Har$^{30}$]

hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23254, the chemical structure of which [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23255, the chemical structure of which [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23256, the chemical structure of which [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23257, the chemical structure of which [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23258, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 23259, the chemical structure of which [N-Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 23260, the chemical structure of which [N-Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 23261, the chemical structure of which [N-Me-Tyr$^1$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 23262, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 23263, the chemical structure of which [N-Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 23264, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 23265, the chemical structure of which [N-Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 24340 the chemical structure of which [N-Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)—OH.

For the synthesis of Peptide 24341 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 24342 the chemical structure of which [Da$^1$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 24344 the chemical structure of which [Da$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 24345 the chemical structure of which [N-Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 24346 the chemical structure of which [N-Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$, the following protected amino acids are coupled in the indicated order on the MBHA resin: Boc-Aha-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 24347 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 24348 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 25501 the chemical structure of which [N-Me-Tyr$^1$, D-Ala$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 25502 the chemical structure of which [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 25503 the chemical structure of which [N-Me-Tyr$^1$, Abu$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Abu-OH, Boc-N-Me-Tyr(2BrZ)—OH.

For the synthesis of Peptide 25504 the chemical structure of which [Dat$^1$, D-Abu$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Abu-OH, Dat-OH.

For the synthesis of Peptide 25506 the chemical structure of which [N-Me-Tyr$^1$, D-Abu$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Abu-OH, Boc-N-Me-Tyr(2BrZ)—OH.

For the synthesis of Peptide 25508 the chemical structure of which [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 25516 the chemical structure of which [N-Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$, the following protected amino acids are coupled in the indicated order on the MBHA resin: Boc-Gab-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 26802 the chemical structure of which [Dat$^1$, D-Ala$^2$, Thr$^8$, His$^{11}$, Orn$^{12}$, Abu$^{15}$, HiS$^{20}$, Orn$^{21}$, Nle$^{27}$, Ada$^{30}$]hGHRH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-His(Bom)-OH, Boc-Tyr(2BrZ)—OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 26803 the chemical structure of which [N-Me-Tyr$^1$, D-Ala$^2$, Gln$^8$, His$^{11}$, Orn$^{12}$, Abu$^{15}$, HiS$^{20}$, Orn$^{21}$, Nle$^{27}$, Ada$^{30}$]hGHRH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-His(Bom)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 26804 the chemical structure of which [N-Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)—OH.

HF cleavage and deprotection, and subsequent purification by semipreparative HPLC of Peptide 21301, Peptide 21303, Peptide 21304, Peptide 21305, Peptide 21306, Peptide 21307, Peptide 21308, Peptide 21309, Peptide 21310, Peptide 21311, Peptide 22325, Peptide 22326, Peptide 22327, Peptide 22328, Peptide 22329, Peptide 22330, Peptide 22331, Peptide 22332, Peptide 22334, Peptide 22335, Peptide 22336, Peptide 22337, Peptide 23250, Peptide 23251, Peptide 23252, Peptide 23253, Peptide 23254, Peptide 23255, Peptide 23256, Peptide 23257, Peptide 23258, Peptide 23259, Peptide 23260, Peptide 23261, Peptide 23262, Peptide 23263, Peptide 23264, Peptide 23265, Peptide 24340, Peptide 24341, Peptide 24342, Peptide 24344, Peptide 24345, Peptide 24346, Peptide 24347, Peptide 24348, Peptide 25501, Peptide 25502, Peptide 25503, Peptide 25504, Peptide 25506, Peptide 25508, Peptide 25516, Peptide 26802, Peptide 26803, Peptide 2680 are done as described in the case of Peptide 21300. The purified compounds are judged to be substantially (>95%) pure by analytical HPLC. Their molecular masses are checked by electrospray mass spectrometry, and the expected amino acid compositions are confirmed by amino acid analysis.

Example 3

Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Arg$^{29}$-NH—CH$_3$ (Peptide 27400). [Dat$^1$, D-Ala$^2$, Orn$^{12}$, Abu$^{15}$, Orn$^{21}$, Nle$^{27}$, Asp$^{28}$]hGHRH(1-29)NH—CH$_3$ The synthesis is conducted in a stepwise manner using manual solid phase peptide synthesis equipment. Briefly, [3-[(Methyl-Fmoc-amino)methyl]-indol-1-yl]-acetyl AM resin (Nova Biochem, La Jolla, Calif.) (750 mg, 0.50 mmol) is deprotected with 20% piperidine in DMF for 5 and 15 minutes and washed according to the protocol described in Table 3. The solution of Fmoc-Arg(Pbf)-OH (975 mg, 1.5 mmol) in DMF is shaken with the washed resin and DIC (235 µL, 1.5 mmol) in a manual solid phase peptide synthesis apparatus for 1 hour. After washing the resin three times with DMF, the coupling reaction was repeated as described above. After the repeated coupling and after the completion of the reaction is proved by negative ninhydrin test, the deprotection and neutralization protocols described in Table 3 are performed in order to remove the Fmoc protecting group and prepare the peptide-resin for coupling of the next amino acid. The synthesis is continued and the peptide chain is built stepwise by coupling the following protected amino acids in the indicated order on the resin to obtain the desired peptide sequence: Fmoc-Asp(OBu$^t$)-OH, Fmoc-Nle-OH, Fmoc-Ile-OH, Fmoc-Asp(OBuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(^Bu$^t$)-OH, Fmoc-D-Ala-OH, Dat-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µL, 1.5 mmol) with the exceptions of Fmoc-Asn(Trt)-OH and Fmoc-Gln(Trt)-OH which are coupled with HBTU reagent.

In order to cleave the peptide from the resin and deprotect it, a portion of 250 mg of the dried peptide resin is stirred with 2.5 mL cleavage cocktail (94% TFA, 3% H$_2$O, 1.5% m-cresol, and 1.5% phenol) at room temperature for 3 hours. To induce peptide precipitation, the cleavage mixture is added dropwise to cold (preferably −20° C.) ether. The precipitated material is collected by filtration or centrifugation and is washed three times with cold ether. The cleaved and deprotected peptide is dissolved in 50% acetic acid and separated from the resin by filtration. After dilution with water and lyophilization, 118 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 118 mg of crude peptide is dissolved in AcOH/H$_2$O, stirred, filtered and applied on an XBridge Prep OBD™ reversed phase column (4.6×250 mm, packed with C$_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 19 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 27401, Peptide 27403, Peptide 27404, Peptide 27405, Peptide 27406, Peptide 27407, Peptide 27408, Peptide 27409, Peptide 27410, Peptide 27411, Peptide 412, Peptide 27413, Peptide 27414, Peptide 27415, Peptide 27416, Peptide 27417, Peptide 27418, Peptide 27419, Peptide 27422, Peptide 27423, Peptide 27424, Peptide 27425, Peptide 27440, Peptide 27441, Peptide 27442, Peptide 27443, Peptide 27444, Peptide 27445, Peptide 27446, Peptide 27447, Peptide 27448, Peptide 27449, Peptide 27450, Peptide 27451 are synthesized in the same manner as Peptide 27400, except that these peptides also contain other amino acid substitutions in the peptide sequence. The details for these syntheses are set forth below.

For the synthesis of Peptide 27401, the chemical structure of which [$Dat^1$, $D-Ala^2$, $Gln^8$, $Orn^{12}$, $Abu^{15}$, $Orn^{21}$, $Nle^{27}$, $Asp^{28}$, $D-Arg^{29}$]hGHRH(1-29)NH—$CH_3$, the following protected amino acids are coupled in the indicated order on the deprotected [3-[(Methyl-Fmoc-amino)methyl]-indol-1-yl]-acetyl Am resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Dat-OH.

For the synthesis of Peptide 27403, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27404, the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-AspCOBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27405, the chemical structure of which [N-Me-Tyr$^1$, Orn$^{12}$, Abu$^{15}$, Orn$^{21}$, Nle$^{27}$]hGHRH(1-29)NHCH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27406, the chemical structure of which [N-Me-Tyr$^1$, Gln$^8$, Orn$^{12}$, Abu$^{15}$, Orn$^{21}$, Nle$^{27}$, Asp$^{28}$]hGHRH(1-29)NH—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27407, the chemical structure of which [Dat$^1$, Gln$^8$, Orn$^{12}$, Abu$^{15}$, Orn$^{21}$, Nle$^{27}$, Asp$^{28}$]hGHRH(1-29)NH—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-AsptOBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Dat-OH.

For the synthesis of Peptide 27408, the chemical structure of which [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspODBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 27409, the chemical structure of which [N-Me-Tyr$^1$, D-Ala$^2$, Orn$^{12}$, Abu$^{15}$, Orn$^{21}$, Nle$^{27}$, Asp$^{28}$]hGHRH(1-29)NH—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser (Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27410, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27411 the chemical structure of which [N-Me-Tyr$^1$, D-Ala$^2$, Thr$^8$, Orn$^{12}$, Abu$^{15}$, Orn$^{21}$, Nle$^{27}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27412 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Ala-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27413 the chemical structure of which [Dat$^1$, Gln$^8$, His$^{11}$, Orn$^{12}$, Abu$^{15}$, HiS$^{20}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-AsptOBu$^1$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 27414 the chemical structure of which [N-Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Gab-OH, Fmoc-Arg(Pbf)-OH, Fmoc-Asp(OBu$^r$)-OH, Fmoc-Nle-OH, Fmoc-Ile-OH, Fmoc-AspfOBuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27415 the chemical structure of which [N-Me-Tyr$^1$, Orn$^{12}$, Abu$^{15}$, Orn$^{21}$, Nle$^{27}$, Gab$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Gab-OH, Fmoc-Arg(Pbf)-OH, Fmoc-Asp(OBu$^r$)-OH, Fmoc-Nle-OH, Fmoc-Ile-OH, Fmoc-AspfOBifyOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-Ala-OH, Fmoc-N-Me-Tyr(tBu)-OH.

For the synthesis of Peptide 27416 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27417 the chemical structure of which [Ac-Tyr$^1$, D-Ala$^2$, Gln$^8$, Orn$^{12}$, Abu$^{15}$, Orn$^{21}$, Nle$^{27}$, Asp$^{28}$]liGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Ac-Tyr(tBu)-OH.

For the synthesis of Peptide 27418 the chemical structure of which [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc- Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Ac-Tyr(tBu)-OH.

For the synthesis of Peptide 27419 the chemical structure of which [Ac-Tyr$^1$, Thr$^8$, Orn$^{12}$, Abu$^{15}$, Orn$^{21}$, Nle$^{27}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Ac-Tyr(tBu)-OH.

For the synthesis of Peptide 27422 the chemical structure of which [N-Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27423 the chemical structure of which [N-Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27424 the chemical structure of which [Dat$^1$, Thr$^8$, Orn$^{12}$, Abu$^{15}$, Orn$^{21}$, Nle$^{27}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Dat-OH.

For the synthesis of Peptide 27425 the chemical structure of which [N-Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27440 the chemical structure of which [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBiO-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Dat-OH.

For the synthesis of Peptide 27441 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp^Bu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln (Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27442 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp^Bu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln (Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr (tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27443 the chemical structure of which [N-Me-Tyr$^1$, Orn$^{12}$, Abu$^{15}$, Orn$^{21}$, Nle$^{27}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27444 the chemical structure of which [N-Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp-COBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27445 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27446 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Ala-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27447 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30NH—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^r$)-OH, Fmoc-Nle-OH, Fmoc-Ile-OH, Fmoc-AspfOBifyOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 27448 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Aha-OH, Fmoc-Arg(Pbf)-OH, Fmoc-Asp(OBu$^r$)-OH, Fmoc-Nle-OH, Fmoc-Ile-OH, Fmoc-AspfOBuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)—OH, Fmoc-D-Ala-OH, Fmoc-N-Me-Tyr(tBu)-OH.

For the synthesis of Peptide 27449 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Amc-OH, Fmoc-Arg(Pbf)-OH, Fmoc-Asp(OBu$^r$)-OH, Fmoc-Nle-OH, Fmoc-Ile-OH, Fmoc-AspfOBifyOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)—OH, Fmoc-D-Ala-OH, Fmoc-N-Me-Tyr(tBu)-OH.

For the synthesis of Peptide 27450 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Har(Pbf)-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-AspBu$^1$)-OH, Fmoc-D-Ala-OH, Fmoc-N-Me-Tyr(tBu)-OH.

For the synthesis of Peptide 27451 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Aha$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH Fmoc-His (Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^BuVOH, Fmoc-D-Ala-OH, Fmoc-N-Me-Tyr(tBu)-OH.

TFA cleavage and deprotection with the cleavage cocktail, and subsequent purification by semipreparative HPLC of Peptide 27401, Peptide 27403, Peptide 27404, Peptide 27405, Peptide 27406, Peptide 27407, Peptide 27408, Peptide 27409, Peptide 27410, Peptide 27411, Peptide 27412, Peptide 27413, Peptide 27414, Peptide 27415, Peptide 27416, Peptide 27417, Peptide 27418,Peptide 27419, Peptide 27422, Peptide 27423, Peptide 27424, Peptide 27425, Peptide 27440, Peptide 27441, Peptide 27442, Peptide 27443, Peptide 27444, Peptide 27445, Peptide 27446, Peptide 27447, Peptide 27448, Peptide 27449, Peptide 27450, Peptide 27451 are done as described in the case of Peptide 27400. The purified compounds are judged to be substantially (>95%) pure by analytical HPLC. Their molecular masses are checked by electrospray mass spectrometry, and the expected amino acid compositions are confirmed by amino acid analysis.

Example 4

N-Me-Tyr$^1$-D-Ala$^2$-Asp$^3$-Ala$^4$-Ile$^5$-Phe$^6$-Thr$^7$-Gln$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Arg$^{29}$-NH—CH$_2$—CH$_3$ (Peptide 28420) N-Me-Tyr$^1$, D-Ala$^2$, Gln$^8$, Orn$^{12}$, Abu$^{15}$, Orn$^{21}$, Nle$^{27}$, Asp$^{28}$]hGHRH (1-29)NH—CH$_2$—CH$_3$. The synthesis is conducted in a stepwise manner using manual solid phase peptide synthesis equipment. Briefly, 3-[(Ethyl-Fmoc-amino)methyl]-indol-1-yl]-acetyl AM resin (Nova Biochem, La Jolla, Calif.) (610 mg, 0.50 mmol) is deprotected with 20% piperidine in DMF for 5 and 15 minutes and washed according to the protocol described in Table 3. The solution of Fmoc-Arg(Pbf)-OH (975 mg, 1.5 mmol) in DMF is shaken with the washed resin and DIC (235 µL, 1.5 mmol) in a manual solid phase peptide synthesis apparatus for 1 hour. After washing the resin three times with DMF, the coupling reaction was repeated as described above. After the repeated coupling and after the completion of the reaction is proved by negative ninhydrin test, the deprotection and neutralization protocols described in Table 3 are performed in order to remove the Fmoc protecting group and prepare the peptide-resin for coupling of the next amino acid. The synthesis is continued and the peptide chain is built stepwise by coupling the following protected amino acids in the indicated order on the resin to obtain the desired peptide sequence: Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-AspfOBuVOH, Fmoc-D-Ala-OH, Fmoc-N-Me-Tyr(tBu)-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxy-terminus of each residue is free.

The protected amino acids (1.5 mmol each) are coupled with DIC (235 µL, 1.5 mmol) with the exceptions of Fmoc-Asn(Trt)-OH and Fmoc-Gln(Trt)-OH which are coupled with HBTU reagent.

In order to cleave the peptide from the resin and deprotect it, a portion of 250 mg of the dried peptide resin is stirred with 2.5 mL of cleavage cocktail (94% TFA, 3% H$_2$O, 1.5% m-cresol, and 1.5% phenol) at room temperature for 3 hours. To induce peptide precipitation, the cleavage mixture is added dropwise to cold (preferably −20° C.) ether. The precipitated material is collected by filtration or centrifugation and is washed three times with cold ether. The cleaved and deprotected peptide is dissolved in 50% acetic acid and separated from the resin by filtration. After dilution with water and lyophilization, 110 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 110 mg of crude peptide is dissolved in AcOH/H$_2$O, stirred, filtered and applied on an XBridge Prep OBD™ reversed phase column (4.6×250 mm, packed with C$_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 16 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 28421, Peptide 28430, Peptide 28431, Peptide 28460,Peptide 28461, Peptide 28462, Peptide 28463, Peptide 28464, Peptide 28465, Peptide 28466, Peptide 28467, Peptide 28468, Peptide 28469, Peptide 28470, Peptide 28471, Peptide 28472, Peptide 28473, Peptide 28474, Peptide 28475, Peptide 28476, Peptide 28477, Peptide 28478, Peptide 28479 are synthesized in the same manner as Peptide 28460, except that these peptides also contain other amino acid substitutions in the peptide sequence. The details for these syntheses are set forth below.

For the synthesis of Peptide 28421 the chemical structure of which [N-Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspODBu-VOH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc- Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28430 the chemical structure of which [N-Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(tBu)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 28431 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28460 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp-COBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28462 the chemical structure of which [N-Me-Tyr$^1$, D-Ala$^2$, Fpa5$^6$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28463 the chemical structure of which [N-Me-Tyr$^1$, D-Ala$^2$, Orn$^{12}$, Abu$^{15}$, Orn$^{21}$, Nle$^{27}$] hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-AspBu'J-OH, Fmoc-D-Ala-OH, Fmoc-N-Me-Tyr(tBu)-OH.

For the synthesis of Peptide 28464 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28465 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 28466 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28467 the chemical structure of which [N-Me-Tyr$^1$, D-Ala$^2$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28468 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-30)NH—CH2-CH3, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp-COBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28469 the chemical structure of which [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28470 the chemical structure of which [Dat$^1$, D-Ala$^2$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28471 the chemical structure of which [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-AspODBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28472 the chemical structure of which [Dat$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$-CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp-COBu$^1$)-OH, Fmoc-Gln-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Dat-OH.

For the synthesis of Peptide 28473 the chemical structure of which [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-AsptOBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Dat-OH.

For the synthesis of Peptide 28474 the chemical structure of which [Dat$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-AspODBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28475 the chemical structure of which [N—Me-Tyr$^1$,D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28476 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH2-CH3, the following protected amino acids are coupled in the indicated order on the deprotected [3-[(Methyl-Fmoc-amino)methyl]-indol-1-yl]-acetyl AM resin: Fmoc-Aha-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)—OH, Fmoc-D-Ala-OH, Fmoc-N-Me-Tyr(tBu)-OH.

For the synthesis of Peptide 28477 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Amc-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28478 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Har(Pbf)-OH, Fmoc-Arg(Pbf)-OH, Fmoc-Asp(OBu$^t$)-OH, Fmoc-Nle-OH, Fmoc-Ile-OH, Fmoc-AspBuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28479 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apan$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

TFA cleavage and deprotection with the cleavage cocktail, and subsequent purification by semipreparative HPLC of Peptide 28421, Peptide 28430, Peptide 28431, Peptide 28460, Peptide 28461, Peptide 28462, Peptide 28463, Peptide 28464, Peptide 28465, Peptide 28466, Peptide 28467, Peptide 28468, Peptide 28469, Peptide 28470, Peptide 28471, Peptide 28472, Peptide 28473, Peptide 28474, Peptide 28475, Peptide 28476, Peptide 28477, Peptide 28478, Peptide 28479 are done as described in the case of Peptide 28420. The purified compounds are judged to be substantially (>95%) pure by analytical HPLC. Their molecular masses are checked by electrospray mass spectrometry, and the expected amino acid compositions are confirmed by amino acid analysis.

Example 5

Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Var$^3$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Ser$^{28}$-Arg$^{29}$-Gln-Gab$^{30}$-NH$_2$ (Peptide 29702) Da$^1$, D-Ala$^2$, Orn$^{12}$, Abu$^{15}$, Orn$^{21}$, Nle$^{27}$, Gln-Gab$^{30}$]hGHRH(1-30)-NH$_2$. The synthesis is conducted in a stepwise manner using manual solid phase peptide synthesis equipment. Briefly, para-methylbenzhydrylamine (MBHA) resin (Bachem, King of Prussia, Pa.) (720 mg, 0.50 mmol) is pre-swollen in DCM and neutralized with 5% DIEA in DCM and washed according to the protocol described in Table I. The solution of Boc-Gab-OH (265 mg, 1.5 mmol) in DMF-DCM (1:1) is shaken with the neutralized resin and DIC (235 µL, 1.5 mmol) in a manual solid phase peptide synthesis apparatus for 1 hour. After the completion of the coupling reaction is proved by negative ninhydrin test, the deprotection and neutralization protocols described in Table 2 are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µL, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 109 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C$_{18}$ silica gel, 300 Å pore size, 3 µm particle size) (Supelco, Bellefonte, Pa.).

Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 109 mg of crude peptide is dissolved in AcOH/H$_2$O, stirred, filtered and applied on an XBridge Prep OBD™ reversed phase column (4.6×250 mm, packed with C$_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 27 mg pure product. The analytical HPLC is carried out on a Supeico Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 29701, Peptide 29703, Peptide 29704, Peptide 29706, Peptide 29708, Peptide 29710, Peptide 29720, Peptide 29721, Peptide 29722, Peptide 29723, Peptide 29724 are synthesized in the same manner as Peptide 29702, except that these peptides also contain other amino acid substitutions in the peptide sequence, and acyl moieties at their N-termini. The details for these syntheses are set forth below.

For the synthesis of Peptide 29701 the chemical structure of which is [N-Me-Tyr$^1$,D-Ala$^2$,Gln$^8$, Orn$^{12}$,Abu$^{15}$,Orn$^{21}$, Nle$^{27}$,Asp$^{28}$,Gln-Gab$^{30}$]hGHRH(1-30)NH$_2$; the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(Bzl)-OH.

For the synthesis of peptide 29703 the chemical structure of which is N-Me-Tyr$^1$, Gln$^8$, Orn$^{12}$,Abu$^{15}$,Orn$^{21}$,Nle$^{27}$, Asp$^{28}$,Gln-Gab$^{30}$] hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Ile-OH, Boc-Asp(OcHx), Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2ClZ)—OH, Boc-Ser(Bzl)-OH, Boc-Gln-OH, Boc-Thr(Bzl)-OH,Boc-Phe-OH, Boc-Ile-OH, Boc-Ala-OH, Boc-Asp(OcHx)-OH, Boc-Ala-OH, Boc-N-Me-Tyr(Bzl)-OH.

For the synthesis of peptide 29704 the chemical structure of which is [Dat$^1$, D-Ala$^2$, Gln$^8$, Orn$^{12}$, Abu$^{15}$, Orn$^{21,22}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Ile-OH, Boc-Asp(OcHx), Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2ClZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(Bzl)-OH.

For the synthesis of Peptide 29706 the chemical structure of which [Tfa-Tyr$^1$, D-Abu$^2$, Gln$^8$, Orn$^{12}$, Abu$^{15}$, Orn$^{21}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Abu-OH, Tfa-Tyr-OH.

For the synthesis of Peptide 29708 the chemical structure of which [N-Me-Tyr$^1$-D-Ala$^2$, Fpa5$^6$, Orn$^{12}$, Abu$^{15}$, Orn$^{21}$, Nle$^{27}$, Gln-Gab$^{30}$]liGHRH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp (OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 29710 the chemical structure of which [N-Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg (Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn (2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 29720 the chemical structure of which [Dat$^1$, D-Ala$^2$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp (OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 29721 the chemical structure of which [Dat$^1$, D-Ala$^2$, Gln$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 29722 the chemical structure of which [Tfa-Tyr$^1$, D-Abu$^2$, Gln$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Abu-OH, Tfa-Tyr-OH.

For the synthesis of Peptide 29723 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

For the synthesis of Peptide 29724 the chemical structure of which [N-Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)—OH, Boc-Arg(Tos)-OH, Boc-Tyr(2BrZ)—OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)—OH.

HF cleavage and deprotection, and subsequent purification by semipreparative HPLC of Peptide 29701, Peptide 29703, Peptide 29704, Peptide 29706, Peptide 29708, Peptide 29710, Peptide 29720, Peptide 29721, Peptide 29722, Peptide 29723, Peptide 29724 are doneas described in the case of Peptide 21300. The purified compounds are judged to be substantially (>95%) pure by analytical HPLC. Their molecular masses are checked by electrospray mass spectrometry, and the expected amino acid compositions are confirmed by amino acid analysis.

Example 6

Aqueous Solution for Intramuscular Injection
[N-Me-Tyr$^1$, Gln$^8$, Orn$^{12}$, Abu$^{15}$, Orn$^{21}$, Nle$^{27}$, Asp$^{28}$, Agm$^{29}$]hGHRH(1-29)

| | |
|---|---|
| (Peptide 20356) | 500.0 mg |
| Gelatin, nonantigenic | 5.0 mg |
| Water for injection q.s | 100.0 mL |

The gelatin and GHRH agonist Peptide 20356 are dissolved in water for injection, and then the solution is sterile filtered.

Example 7

Long Acting Intramuscular Injectable Formulation (Sesame Oil Gel)
[N-Me-Tyr$^1$, Gln$^8$, Orn$^{12}$, Abu$^{15}$, Orn$^{21}$, Nle$^{27}$, Asp$^{28}$, Agm$^{29}$]hGHRH(1-29)

| | |
|---|---|
| (Peptide 20356) | 10.0 mg |
| Aluminum monostearate, USP | 20.0 mg |
| Sesame oil | 1.0 mL |

The aluminum monostearate is combined with the sesame oil and heated to 125° C. with stirring until a clear yellow solution forms. This mixture is then autoclaved for sterility and allowed to cool. The GHRH agonist Peptide 20356 is then added aseptically with trituration. Particularly preferred agonists are salts of low solubility, e.g., pamoate salts and the like. These exhibit long duration of activity.

Example 7

Long Acting Intramuscular (IM) Injectable-Biodeqradable Polymer Microcapsules
Microcapsules are made from the following:

| | |
|---|---|
| 25/75 glycolide/lactide copolymer (0.5 intrinsic viscosity) | 99% |
| [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29) | |
| (Peptide 20356) | 1% |

25 mg of the above microcapsules are suspended in 1.0 mL of the following vehicle:

| | |
|---|---|
| Dextrose | 5.0% |
| CMC, sodium | 0.5% |
| Benzyl alcohol | 0.9% |
| Tween 80 | 0.1% |
| Water, purified q.s. | 100% |

Example 9

Growth hormone releasing activity. Growth hormone releasing was assayed by using a superfused rat pituitary cell system as described in S. Vigh and A. V. Schally, Peptides 5, Suppl: 241-347, 1984. The new synthetic peptide analog of hGHRH P20356 and JI-38 (as control) were administered for 3 minutes (1 mL perfusate) at 1 nM concentration as shown below. Fractions of 1 ml are collected and the GH content in each was determined by ELISA. Peptide P20356 was about 3 times more potent in vitro than JI-38. Table 4 shows GH-releasing effects of GHRH agonist P20356 (MR-356) and JI-38 in superfused rat pituitary cells.

TABLE 4

GH Response P-20356 vs JI-38
Basal GH (ng/ml) 42.51

| GH Response (ng/ml) | 1 | 2 | 3 | Average |
|---|---|---|---|---|
| P-20356 (1 nM) | | | | |
| 1 | 49.98 | 54.99 | 52.37 | 52.45 |
| 2 | 310.58 | 325.76 | 376.11 | 337.48 |
| 3 | 491.01 | 602.1 | 576.26 | 556.46 |
| 4 | 399.95 | 270.02 | — | 334.99 |
| 5 | 200.64 | 195.18 | — | 197.91 |
| JI-38 (1 nM) | | | | |
| 21 | 42.46 | 56.07 | — | 49.27 |
| 22 | 143.58 | 119.83 | — | 131.71 |
| 23 | 222.13 | 167.23 | — | 194.68 |
| 24 | 142.96 | 131.93 | — | 137.45 |
| 25 | 96.34 | 97.05 | — | 96.70 |

Conclusion: P-20356 is 2-3 times more potent than JI-38

Pituitary cells from 2 male rats were used for each channel of the superfusion system. The cells were exposed to 3-min pulses of the new GHRH agonists or to JI-38 as standard every 30 min. Outflowing samples of each channel (1 ml) were collected every 3 min, and GH levels were determined by ELISA.

Example 10

Receptor binding assay. Ligand competition assay with $^{125}$I-labeled [His$^1$, Nle$^{27}$]hGHRH(1-32)-NH$_2$ was used to determine the binding affinities of the novel hGHRH agonists to membrane receptors of rat anterior pituitary cells. The methods used have been described in detail (Halmos G, et al. Receptor 3: 87-97, 1993). Briefly, radioiodonated [His$^1$, Nle$^{27}$]hGHRH(1-32)-NH$_2$ is prepared by the chloramine-T method. In competitive binding analyses, $^{125}$I-labeled [His$^1$, Nle$^{27}$]hGHRH(1-32)-NH$_2$ (0.2 nM) was displaced by the GHRH analogs at $10^{-6}$-$10^{-12}$ M. The final binding affinities were calculated using the LIGAND-PC computerized curve-fitting program. Relative affinities were compared to hGHRH(1-29) and/or analog JI-38 (Izdebski J, et al. Proc. Natl. Acad. Sci. 92: 4872-4876, 1995) and calculated as the ratio of IC$_{50}$ of the tested peptide to the IC$_{50}$ of the standard. IC$_{50}$ is the dose of the tested peptides causing 50% inhibition of specific binding to receptors.

GHRH Receptor Binding Studies
Binding Affinities
Materials and Methods

Preparation of human pituitary membrane fraction and receptor binding of GHRH agonists were performed by using a sensitive in vitro ligand competition assay based on binding of $^{125}$I-labeled JV-1-42 to human pituitary membrane homogenates. Normal human pituitaries were purchased from the National Hormone and Peptide Program (A.F. Parlow, Los Angeles, County Harbor-UCLA Medical Center, Torrance, Calif.). Briefly, in competitive binding analysis, $^{125}$I-labeled JV-1-42 (–0.2 nM) was displaced by GHRH agonists at $10^{-6}$ to $10^{-12}$ M.

The final binding affinities were expressed as IC$_{50}$ values and were calculated by using the LIGAND PC computerized curve-fitting program of Munson and Rodbard as modified by McPherson.

Results

The results of these experiments are given in the Table 5. IC$_{50}$ values of the best agonists were in the 0.01-0.09 nM range. Based on the receptor binding results, all the new GHRH agonists exceeded the binding affinity of the reference peptide JI-38. Some of these new GHRH agonists tested showed the highest GHRH receptor binding affinity, their IC$_{50}$ values being 45-406 times lower than that of GHRH(1-29). Based on its IC$_{50}$ value, GHRH agonist P20356 showed 171 times higher binding affinity than the refrence compound JI-38.

TABLE 5

| | | Relative affinitiy (Binding potency) | |
|---|---|---|---|
| GHRH agonists | IC$_{50}$ (nM) | vs GHRH | vs JI-38 |
| GHRH (1-29) | 4.06 | 1 | |
| JI-38 | 1.71 | 2.4 | 1 |
| P20303 | 0.09 | 45.1 | 19.0 |
| P20350 | 0.04 | 101.5 | 42.7 |
| P20356 | 0.01 | 406.0 | 171.0 |
| P25502 | 0.07 | 58.0 | 24.4 |
| P29702 | 0.05 | 81.2 | 34.2 |

*Expressed relative to GHRH(1-29) = 1 or JI-38 (GHRH agonist) = 1, Values were calculated from duplicate tubes.

GHRH Receptor Binding Studies
Binding Affinities
Materials and Methods

Preparation of human pituitary membrane fraction and receptor binding of GHRH agonists were performed by using a sensitive in vitro ligand competition assay based on binding of $^{125}$I-labeled [His$^1$, Nle$^{27}$]hGHRH(1-32)NH$_2$ to human pituitary membrane homogenates. Normal human pituitaries were purchased from the National Hormone and Peptide Program (A.F. Parlow, Los Angeles, County Harbor-UCLA Medical Center, Torrance, Calif.).

Briefly, in competitive binding analysis, [His$^1$,$^{125}$I-Tyr$^{10}$, Nle$^{27}$] hGHRH(1-32)NH$_2$ (0.2 nM) was displaced by GHRH agonists at $10^{-6}$ to $10^{-12}$ M. The final binding affinities were expressed as IC$_{50}$ values and were calculated by using the LIGAND PC computerized curve-fitting program of Munson and Rodbard as modified by McPherson.

Results

The results of these experiments are given in the Table 6. IC$_{50}$ values of the best agonists were in the 0.04-0.09 nM range. Based on the receptor binding results all new GHRH agonists exceeded the binding affinity of reference peptides JI-34, JI-36 and JI-38. Some of these new GHRH agonists showed the highest GHRH receptor binding affinity, their IC$_{50}$ values being 21-48 times lower than that of the GHRH agonist JI-38.

TABLE 6

IC$_{50}$ VALUES AND BINDING ACTIVITIES OF NEW GHRH AGONISTIC ANALOGS

| | | Relative affinitiy (Binding potency) | |
|---|---|---|---|
| GHRH agonists | IC$_{50}$ (nM) | vs GHRH | vs JI-38 |
| GHRH(1-29) | 5.92 | 1 | |
| JI-34 | 1.37 | 4.32 | |
| JI-36 | 1.82 | 3.25 | |
| JI-38 | 1.95 | 3.03 | 1 |
| P-23252 | 0.14 | 42.3 | 13.9 |
| P-23254 | 0.07 | 84.5 | 27.8 |

TABLE 6-continued

IC$_{50}$ VALUES AND BINDING ACTIVITIES
OF NEW GHRH AGONISTIC ANALOGS

| GHRH agonists | IC$_{50}$ (nM) | Relative affinitiy (Binding potency) vs GHRH | vs JI-38 |
|---|---|---|---|
| P-23256 | 0.04 | 148.0 | 48.7 |
| P-21304 | 0.08 | 74.0 | 24.4 |
| P-20352 | 0.07 | 84.5 | 27.8 |

*Expressed relative to GHRH(1-29) = 1 or JI-38 (GHRH agonist) = 1 Values were calculated from duplicate or triplicate tubes.

GHRH Receptor Binding Studies
Binding Affinities
Materials and Methods

Preparation of human pituitary membrane fraction and receptor binding of GHRH agonists were performed by using a sensitive in vitro ligand competition assay based on binding of $^{125}$I-labeled JV-1-42 to human pituitary membrane homogenates. Normal human pituitaries were purchased from the National Hormone and Peptide Program (A.F. Parlow, Los Angeles, County Harbor-UCLA Medical Center, Torrance, Calif.).

Briefly, in competitive binding analysis, $^{125}$I-labeled JV-1-42 (~0.2 nM) was displaced by GHRH agonists at $10^{-6}$ to $10^{-12}$ M. The final binding affinities were expressed as IC$_{50}$ values and were calculated by using the LIGAND PC computerized curve-fitting program of Munson and Rodbard as modified by McPherson.

Results

The results of these experiments are given in the Table 7. IC$_{50}$ values of the best agonists were in the 0.16-0.87 nM range. Based on the receptor binding results most of the new GHRH agonists exceeded the binding affinity of reference peptides JI-38. Some of these new GHRH agonists showed 5-27 times higher binding potency than GHRH agonist JI-38. See Table 7.

TABLE 7

IC$_{50}$ VALUES AND BINDING ACTIVITIES
OF NEW GHRH AGONISTIC ANALOGS

| GHRH agonists | IC$_{50}$ (nM) | Relative affinitiy (Binding potency) vs JI-38 |
|---|---|---|
| JI-38 | 4.35 | 1 |
| P-21300 | 3.61 | 1.20 |
| P-21301 | 2.99 | 1.45 |
| P-21303 | 1.87 | 2.32 |
| P-22325 | 3.80 | 1.14 |
| P-22326 | 0.71 | 6.12 |
| P-22327 | 1.99 | 2.18 |
| P-20357 | 0.86 | 5.06 |
| P-20350 | 0.52 | 8.37 |
| P-20351 | 3.44 | 1.26 |
| P-20356 | 0.27 | 16.11 |
| P-20359 | 3.05 | 1.43 |
| P-20361 | 0.82 | 5.30 |
| P-20367 | 1.70 | 2.56 |
| P-25501 | 1.07 | 4.07 |
| P-25502 | 0.33 | 13.18 |
| P-25503 | 1.18 | 3.67 |
| P-25504 | 1.44 | 3.02 |
| P-27413 | 2.45 | 1.78 |
| P-27414 | 1.56 | 2.79 |
| P-27415 | 3.02 | 1.44 |
| P-29702 | 0.86 | 5.06 |
| P-29703 | 1.22 | 3.57 |
| P-27400 | 3.35 | 1.30 |

TABLE 7-continued

IC$_{50}$ VALUES AND BINDING ACTIVITIES
OF NEW GHRH AGONISTIC ANALOGS

| GHRH agonists | IC$_{50}$ (nM) | Relative affinitiy (Binding potency) vs JI-38 |
|---|---|---|
| P-27401 | 2.74 | 1.59 |
| P-27403 | 0.16 | 27.19 |
| P-27404 | 0.87 | 5.00 |
| P-27405 | 1.08 | 4.03 |
| P-27406 | 0.30 | 14.5 |
| P-27407 | 3.00 | 1.45 |
| P-27408 | 0.55 | 7.91 |
| P-27409 | 1.06 | 4.10 |
| P-27410 | 0.83 | 5.24 |
| P-28420 | 0.52 | 8.37 |
| P-28421 | 1.47 | 2.96 |

*Expressed relative to JI-38 (GHRH agonist) = 1 Values were calculated from duplicate tubes, "reference compound.

Example 11

In vivo tests on endocrine activity of new GHRH agonists (Intravenous administration). For in vivo tests based on intravenous administration, adult male Sprague-Dawley rats were anesthetized with pentobarbital (6 mg/100/g, b.w.), and GHRH agonists were injected 20 minutes after the injection of pentobarbital. Blood samples were taken from the jugular vein (pretreated level), immediately after hGHRH(1-29)NH$_2$ injection (as a control) or after hGHRH analogs injection. Blood samples were taken from the jugular vein 5, 15 and 30 minutes after the injection. The blood samples were centrifuged, plasma was removed and the GH level was measured by ELISA. The results were expressed as potency relative to hGHRH(1-29)NH$_2$ (Table 8).

TABLE 8

GH releasing potencies of hGHRH analogs in vivo
relative to JI-38 (=1) in the rat after i.v. injection

| hGHRH Analog | After (min) | Potency |
|---|---|---|
| P-20356 | 5 | 1.07 |
|  | 15 | 0.91 |
|  | 30 | 1.22 |
| P-21300 | 5 | 0.39 |
|  | 15 | 0.51 |
|  | 30 | 0.81 |
| P-21301 | 5 | 0.79 |
|  | 15 | 0.92 |
|  | 30 | 1.00 |
| P-21303 | 5 | 0.79 |
|  | 15 | 1.14 |
|  | 30 | 0.81 |
| P-22326 | 15 | 0.28 |
|  | 30 | 0.94 |
| P-25502 | 5 | 6.76 |
|  | 15 | 5.40 |
|  | 30 | 5.83 |
| P-25504 | 5 | 1.66 |
|  | 15 | 1.65 |
|  | 30 | 1.37 |
| P-27403 | 15 | 5.01 |
|  | 30 | 4.01 |
| P-27450 | 5 | 0.07 |
|  | 15 | 0.11 |
|  | 30 | 0.49 |
| P-28475 | 5 | 0.19 |
|  | 15 | 0.36 |
|  | 30 | 0.92 |
| P-29702 | 5 | 0.98 |
|  | 15 | 0.99 |
|  | 30 | 1.22 |

Subcutaneous Administration. Adult male rats were used and anesthetized with pentobarbital (6 mg/100 g, b.w.), by i.p. injection. 20 minutes after the injection of pentobarbital, blood samples were taken from the jugular vein (pretreated level), immediately after hGHRH(1-29)NH$_2$ (as a control) or hGHRH analogs were injected subcutaneously (s.c). Blood samples were taken from the jugular vein 5, 15 and/or 30 minutes after the injection. The blood samples were centrifuged, plasma was removed and the GH level was measured byELISA. The results are summarized in terms of potency in Table 9.

TABLE 9

GH releasing potencies of hGHRH analogs after subcutaneous (s.c.) injection relative to JI-38 (=1)

| hGHRH analog | After (min) | Potency |
|---|---|---|
| P-20350 | 15 | 1.53 |
|  | 30 | 1.17 |
| P-20351 | 15 | 0.38 |
|  | 30 | 0.44 |
| P-20353 | 15 | 0.26 |
|  | 30 | 0.31 |
| P-20356 | 15 | 1.72 |
|  | 30 | 1.09 |
| P-20357 | 5 | 0.63 |
|  | 15 | 1.07 |
|  | 30 | 1.41 |
| P-20360 | 15 | 0.24 |
|  | 30 | 0.39 |
| P-20361 | 15 | 1.18 |
|  | 30 | 1.50 |
| P-20367 | 15 | 1.12 |
|  | 30 | 2.01 |
| P-20373 | 15 | 0.23 |
|  | 30 | 0.88 |
| P-21301 | 15 | 0.41 |
|  | 30 | 0.74 |
| P-221303 | 15 | 0.95 |
|  | 30 | 1.45 |
| P-22325 | 5 | 0.33 |
|  | 15 | 0.68 |
|  | 30 | 1.03 |
| P-22326 | 15 | 1.76 |
|  | 30 | 2.31 |
| P-22327 | 15 | 1.15 |
|  | 30 | 1.30 |
| P-25501 | 5 | 1.40 |
|  | 15 | 1.36 |
|  | 30 | 1.63 |
| P-25502 | 15 | 1.10 |
|  | 30 | 0.94 |
| P-25503 | 5 | 0.55 |
|  | 15 | 0.64 |
|  | 30 | 0.63 |
| P-25504 | 15 | 0.78 |
|  | 30 | 0.98 |
| P-27400 | 15 | 0.47 |
|  | 30 | 0.38 |
| P-27401 | 15 | 0.61 |
|  | 30 | 0.73 |
| P-27403 | 15 | 3.60 |
|  | 30 | 2.57 |
| P-27404 | 15 | 2.07 |
|  | 30 | 1.47 |
| P-27405 | 15 | 1.60 |
|  | 30 | 1.13 |
| P-27406 | 15 | 0.47 |
|  | 30 | 0.50 |
| P-27409 | 15 | 1.47 |
|  | 30 | 1.31 |
| P-27412 | 15 | 1.10 |
|  | 30 | 1.29 |
| P-27413 | 15 | 0.36 |
|  | 30 | 0.57 |
| P-27414 | 15 | 1.30 |
|  | 30 | 1.23 |
| P-27415 | 15 | 0.45 |
|  | 30 | 0.41 |
| P-27425 | 15 | 0.49 |
|  | 30 | 0.31 |
| P-29701 | 5 | 0.92 |
|  | 15 | 1.30 |
|  | 30 | 1.55 |
| P-29702 | 15 | 0.53 |
|  | 30 | 0.73 |
| P-29703 | 5 | 1.18 |
|  | 15 | 0.96 |
|  | 30 | 1.04 |

Analysis of endocrine tests: Following intravenous administration, the new analogs stimulated growth hormone levels to a greater extent than hGHRH(1-29)NH$_2$ or JI-38. The effect was long lasting which indicated that the analogs have higher receptor affinity and also increased peptidase resistance. The most potent analogs when administered i.v. were P-27403 and P-25502. Following subcutaneous administration, the analogs that stimulated greater growth hormone levels than hGHRH or JI-38 were P-22326, P-20350, P-20356, P-27403, P-27404, P-27409, P-25501, and P-25502.

Results of i.v. and s.c. administration showed different biological activity patterns. Analogs given by i.v. administration may be subjected to degradation in the blood stream. Analogs given s.c. could be potentially degraded by peptidase at the site of injection. Thus, it is believed that activity of the peptide may depnde on favorable transport properties, suitable binding to plasma proteins, and peptide stability. The above findings therefore indicate that the analogs showing better activity when given subcutaneously are resistant to local degradation at the injection site and they may also be less susceptible to enzyme degradation in the blood stream. In conclusion, the most potent analogs when administered i.v. were P-27403 and P-25502. Following subcutaneous administration, the analogs that stimulated greater growth hormone levels than hGHRH or JI-38 were P-22326, P-20350, P-20356, P-27403, P-27404, P-27409, P-25501, and P-25502.

Example 11

Rescue of impaired tube formation of nitrosoglutathione reductase$^{-/-}$ (GSNOR$^{-/-}$) mesenchymal stem cells (MSCs) by GHRH agonists.

Bone marrow-derived MSCs isolated from wildtype and GSNOR$^{-/-}$ mice were grown in endothelial growth media (EGM-2, Lonza Biotech) for a period of 1 week. Cells were harvested by brief trypsinization and plated in 24-well culture dishes (5×10$^4$ cells/well) pre-coated with 300 µl of Matrigel (BD Biosciences). Cells were incubated in endothelial basal media (Lonza Biotech) supplemented with 0.1% bovine serum albumin, in the presence or absence of GHRH agonist peptides P-20356 and P-27409. After 6 to 24 hours, tube formation potential was quantified in each sample by measuring the number and length of tubes formed using Image J Software (NIH). The GSNOR$^{-/-}$ MSCs treated with GHRH agonists formed tube-like structures similar to wildtype MSCs (FIG. 1). In contrast, untreated GSNOR$^{-/-}$ MSCs exhibited significantly fewer tube-like structures under similar conditions.

Example 13

GHRH agonists improve cardiac repair after myocardial injury in rat models.

Animal Model

All experiments involving rats were carried out in accordance with protocols reviewed and approved by the University of Miami Animal Care and Use Committee in compliance with the *Guide for the Care and Use of Laboratory Animals* (NIH publication no. 85-23, revised 1996). Myocardial infarction (MI) was induced by permanent ligation of the left coronary artery in female 6-month-old Fisher-344 rats. Animals were randomly assigned to receive placebo (DMSO+propylene glycol) or one of the GHRH-agonists (JI-38, MR-356/P-20356, MR-409/P-27409, all 50 µg/kg), starting 4 weeks post-MI. All treatment was given subcutaneously twice daily for 4 weeks.

Drugs

GHRH-agonists were synthesized in the laboratories of one of the inventors.

Echocardiographic Measurements

Echocardiographic measurements were obtained at baseline, 2 days, 1, 2 and 4 weeks. Echocardiographic assessments were performed in anesthetized rats (2% isoflurane inhalation) using a Vevo-770 echocardiogram (Visual Sonics Inc., Toronto, Ontario, Canada) equipped with a 17.5-MHz transducer. Cardiac dimensions: LV end diastolic (LVEDD), end systolic (LVESD) diameters and fractional shortening (FS) were recorded from M-mode images using averaged measurements from 3 to 5 consecutive cardiac cycles according to the American Society of Echocardiography. Ejection fraction (EF) was calculated from bi-dimensional long-axis parasternal views taken through the infarcted area. All images were analyzed using Vevo 770 3.0.0 software (Visual Sonics Inc., Toronto, Ontario, Canada).

Hemodynamic Measurements

Rats were anesthetized by intramuscular injection of a mixture of ketamine (100 mg/kg), xylazine (20 mg/kg) and acepromazine (10 mg/kg). A 2-F micromanometer tipped catheter (SPR-838, Millar Instruments, Houston, Tex.) was inserted into the right carotid artery and advanced retrograde into the left ventricle. Measurements were calibrated by injecting a hypertonic saline (15%) bolus to determine extra-ventricular conductance; relative volume units were converted to actual volume using the cuvette calibration method. All analyses were performed using PVAN 3.0 software (Millar Instruments, Houston, Tex.). Left ventricular pressure-volume relations were assessed by transiently compressing the inferior vena cava.

Blood Collection

Blood was drawn at baseline, 1 and 4 weeks. Plasma and serum were stored at −80° C. for GH/IGF-I measurements and cytokines levels.

Morphometric Analysis

Rat hearts were processed using routine histological procedures. Samples were fixed in formalin.

Immunostaining

Paraffin sections were deparaffinized and rehydrated by immersion in xylene followed by a graded series of ethanol. Antigen retrieval was performed by a heat-induced method with citrate buffer (Dako, Carpinteria, Calif.). After blocking with 10% normal donkey serum, sections were incubated with a primary antibody at 37° C. for 1 hour, followed by application of secondary antibody. Omission of the primary antibodies on parallel sections was used as negative control. Nuclei were counterstained with DAPI (Invitrogen, Carlsbad, Calif.). The total numbers of positively-stained cells (c-kit, CD45, phospho-histone H3 [pH$_3$]) were quantified per slide to calculate the number of cells per section on each sample. Morphometric analysis was performed using Adobe Photoshop CS3 (San Jose, Calif.).

All images were obtained with fluorescent (Olympus IX81, Olympus America Inc., Center Valley, Pa.) or a LSM710 Zeiss confocal laser scanning module (Carl Zeiss MicroImaging).

Statistical Analysis

All values are shown as mean±SEM. Echocardiographic parameters during a 4-week follow-up were compared within and between groups using one-way ANOVA for repeated measurements and two-way ANOVA followed by post-hoc tests, respectively. For a given parameter, $p<0.05$ was considered significant. All tests were carried out using Sigma Stat 3.5 (Jandel, San Rafael, Calif.).

Results

Figure 2:
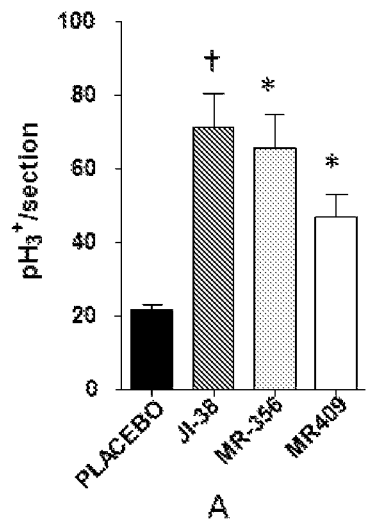
FIG. 2 illustrates immunostaining of heart tissue. Panel A: Bar graphs correspond to expression of pH3 positive cells in the heart; Panel B: Bar graphs that correspond to expression of c-kit positive cells in the heart. c-kit expression was markedly increased in the agonist treated groups. All values represent mean±SEM (n=4-6).
Figure 2:
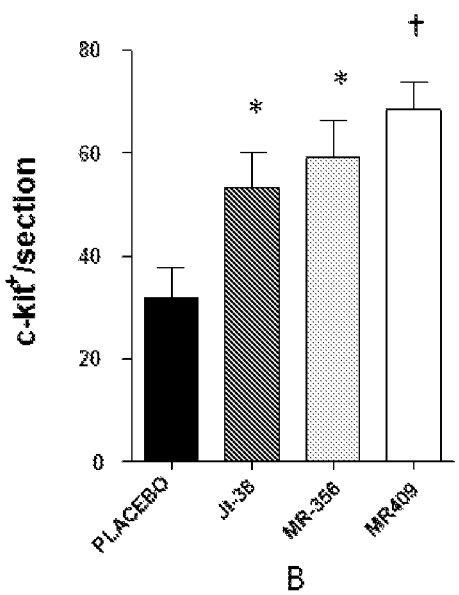
Figure 3:
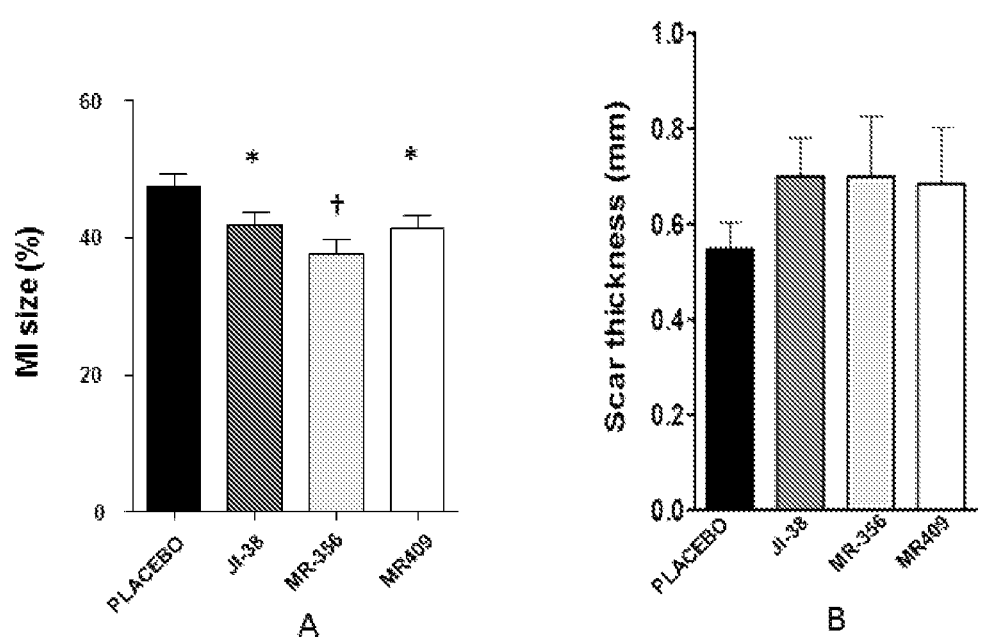
FIG. 3 illustrates morphometric measurements. Panel A depicts bar graphs that correspond to infarct size; Panel B depicts bar graphs that correspond to scar thickness; (*p<0.05 and † p<0.01 versus placebo); All values represent mean±SEM (n=4-6).
Figure 4:
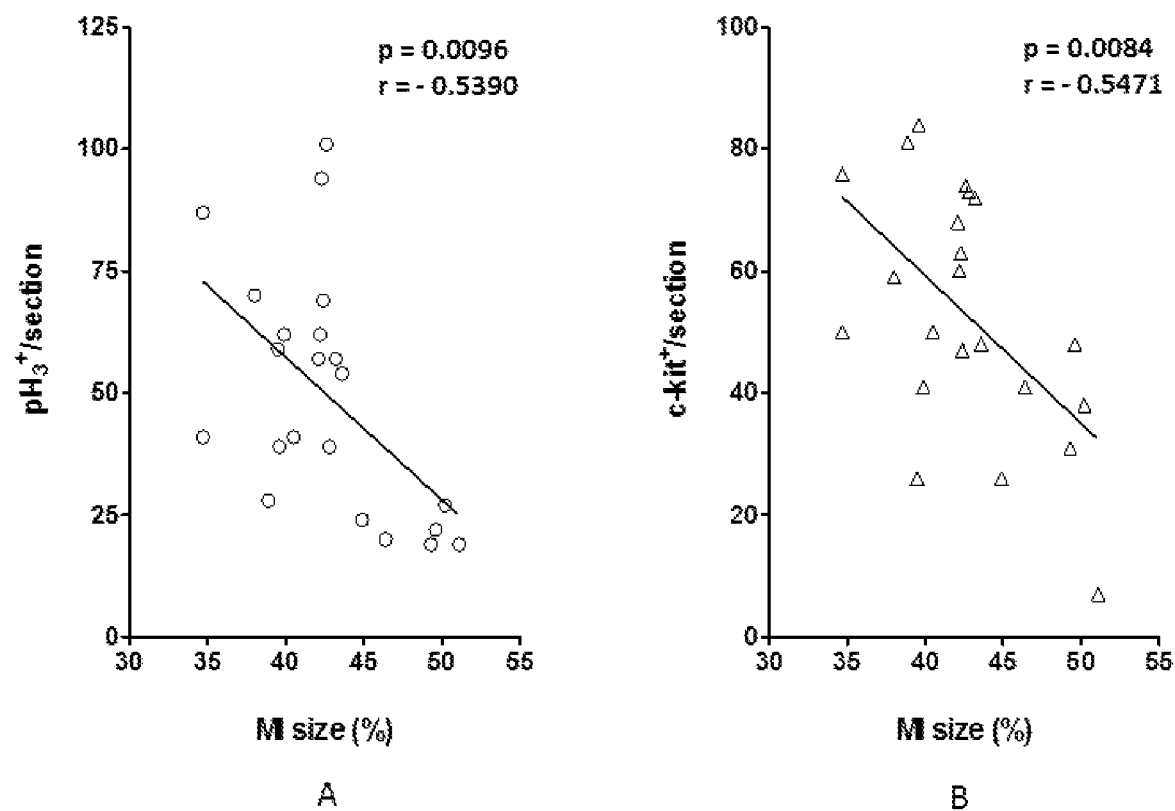
FIG. 4 illustrates Pearson correlation. Panel A shows correlation between expression of pH3+ cells and infarct size. Panel B shows correlation between c-kit+ cells and infarct size.

At baseline and after MI, echocardiographic parameters of ejection fraction (EF) were similar in all groups (Table 10). Over a 4-week period, a reduction in EF from to 88±1 to 38±2% ($p<0.05$) due to MI was ameliorated in animals treated with GHRH-agonists (48±1%, $p<0.05$ for each vs. placebo). MI size was substantially reduced by GHRH-agonists (Table 10 and FIG. 3) (41±1 vs. 49±2%, $p<0.05$,) and importantly, all of these effects were accompanied by an increased number of c-kit$^+$ cells and cellular mitotic division (phospho-histone H3 levels) in the myocardium (see FIG. 2, and Table 10). An inverse correlation between infarct size, and c-kit expression and cardiomyocyte mitotic index (phospho-histone H3) was observed (FIG. 4).

Figure 5:
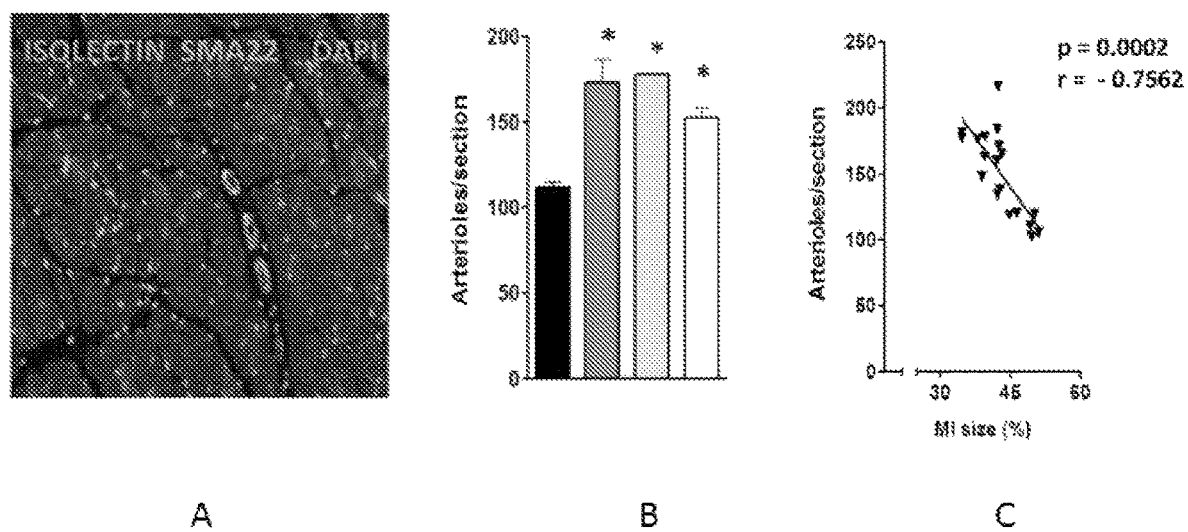
FIG. 5 shows immunohistochemistry of heart tissue; Panels A and B show staining of heart tissue with antibodies against isolectin and vascular smooth muscle (SMA22a); Panel C shows correlation between number of arterioles and infarct size.

Heart sections were co-stained with isolectin (endothelial cell marker) and vascular smooth muscle (SMA22a) to identify arterioles which play a crucial role in cardiac repair. GHRH-agonists (JI-38, MR-356 and MR-409) significantly increased the number of arterioles (FIGS. 5A, B). An inverse correlation between number of arterioles and infarct size was observed (FIG. 5C).

Activation of GHRH receptor in the heart led to significant recovery of the damaged myocardium and improvement in cardiac function. MI size was reduced and the number of mitotic cardiomyocytes substantially increased, providing evidence that administration of GHRH agonists can increase myocyte renewal and mediate cardiac growth after MI and may be an effective therapeutic strategy to rescue/repair the infarcted heart

TABLE 10

|  | Placebo | JI-38 | MR-356 | MR-409 |
| --- | --- | --- | --- | --- |
| EF (Baseline) | 88 ± 1.4 | 88 ± 1.2 | 88 ± 0.6 | 90 ± 0.8 |
| EF (4 Weeks) | 38 ± 1.8* | 47 ± 2.4*† | 51 ± 2.7*† | 48 ± 2.8*† |
| MI size (%) | 49 ± 2.4 | 42 ± 1.3‡ | 37 ± 2.5# | 42 ± 1.9‡ |
| phospho H3 | 22 ± 1.3 | 71 ± 9.2# | 65 ± 9.3‡ | 47 ± 5.8‡ |
| c-kit | 32 ± 5.9 | 53 ± 6.7‡ | 59 ± 7.1‡ | 68 ± 5.5# |

*$p < 0.05$ vs. Baseline same group
†$p < 0.05$ vs. Placebo, same time point
‡$p < 0.05$ vs. Placebo
$p < 0.01$ vs. Placebo

Example 14

Effect of GHRH agonists on cardiac tissue.
Synthesis and Purification of Peptides Three types of GHRH(1-29) analogs modified at the C-terminal were synthesized:

(I) Five C-terminal Agm GHRH(1-29) analogs (Table 11, Group I) were synthesized on Boc-Agm-SPAMBHA resin with Boc-chemistry. Boc-amino acid derivatives were used in the synthesis. The side chains of the amino acids were protected by the following groups: Asp, cyclohexyl; Arg, tosyl; Orn, 2-chlorobenzyloxycarbonyl; Ser, Thr and N-Me-Tyr, benzyl; Tyr, 2,6-dichlobenzyloxycarbonyl; Orn, 2-chlorobenzyloxycarbonyl. The side chains of Asn, Gln and Dat were unprotected. The coupling reactions were achieved with a 3-fold excess of Boc-amino acid and 1-hydroxybenzotriazole. N,N'-diisopropylcarbodiimide was used as a coupling agent. Boc-Gln was coupled with preformed 1-hydroxybenzotriazole ester. In cases where incomplete coupling was found, the coupling procedure was repeated. Acetylation was performed with 30% (v/v) acetic anhydride in dichloromethane for 20 min. Intermediate deblocking was performed with 50% (v/v) trifluoroacetic acid in dichloromethane followed by neutralization with 5% (v/v) diisopropylethylamine in dichloromethane. After completion of the synthesis, the peptide resin was treated by HF in the presence of 3% cresol at 0° C. for 2 hrs. After removal of HF, the free peptides were precipitated and washed with diethyl ether. The crude C-terminal Agm peptide was then analyzed by HPLC and mass spectrometry (Table 11, Group I).

Figure 6:
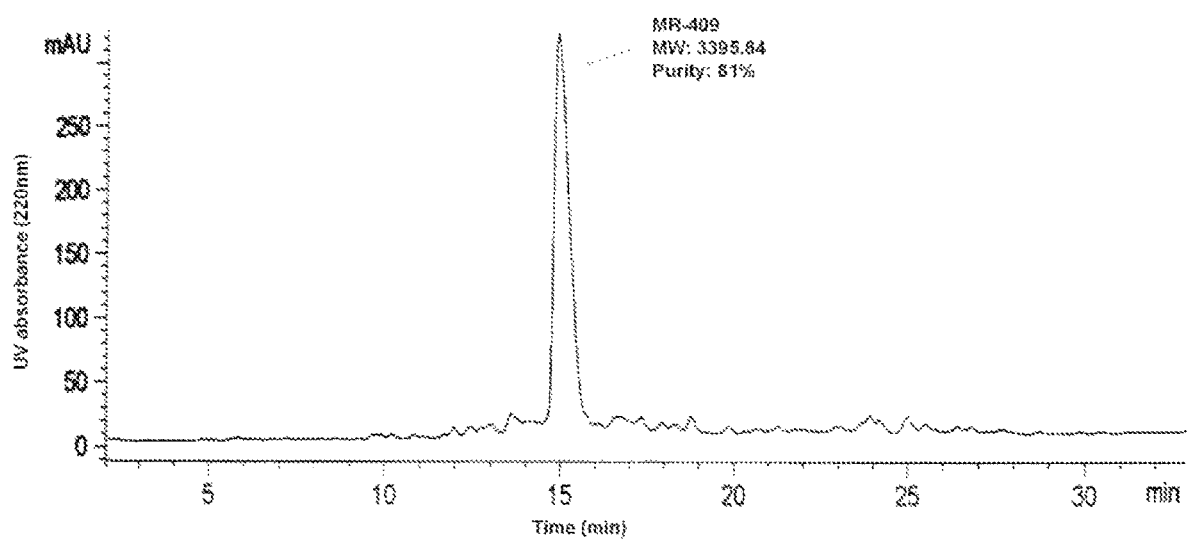
FIG. 6 shows the HPLC analysis of crude sample MR-409 on Agilent Zorbax 300SB C18 column (2.1 mm×50 mm, particle size 5 μm). UV detector 220 nm; Sample Injection 20 μg/25 μl; Eluent A: 0.1% Trifluoroacetic acid in water; Eluent B: 0.1% Trifluoroacetic acid, 70% Acetonitrile in water; linear gradient from 20% B to 60% B in 40 min; MR-409 peak purity: 81%.

(II) Nine C-terminal methylamide and two ethylamide hGHRH(1-29)NH2 analogs (Table 11, Group II) were synthesized using the Fmoc peptide synthesis on {3-[(methyl-Fmoc-amino)-methyl]-indol-1-yl} acetyl AM resin. Two C-terminal ethylamide hGHRH(1-29)NH$_2$ analogs were synthesized on {3-[(ethyl-Fmoc-amino)methyl]indol-1-yl}-acetyl AM resin. Before starting the synthesis, the Fmoc group was removed from the resin with 20% piperidine in dimethylformamide for 20 min. The side chains of Fmoc$^\alpha$-amino acids were protected with acid unstable groups such as β-tert-butyl ester for Asp; tert-butyl (But) for Ser, Thr, N-Me-Tyr and Tyr; Nco-pentamethyldihydrobenzofuran-5-sulfonyl (Pbf) for Arg and D-Arg; N$_\delta$-tert-butoxycarbonyl (Boc) for Orn; N$_\gamma$-trityl for Asn and N$_\delta$-trityl for Gln. Dat was unprotected. The coupling of Fmoc amino acid was achieved using HBTU [2-(1Hbenzotriazole-1-Yl)-1,1,3,3-tetramethyluronium hexafluorophosphate] activation performed with 3 equivalents of Fmoc amino acid and HBTU mixed in DMF, followed by addition of 6 equivalents of N,N-Diisopropylethylamine (DIPEA) and stirred for 2 minutes to become a complete solution. The mixture was then immediately added to Fmoc-deblocked resin and incubated for 1-2 hrs. As an example of synthesis of C-terminal methyamide analog, MR-409: The protected amino acids were coupled to 3.2 g of {3-[(methyl-Fmoc-amino)-methyl)]-indol-1-yl} acetyl AM resin in the following order: Fmoc-Arg(Pbf), Fmoc-Asp(OBu$_t$), Fmoc-Nle, Fmoc-Ile, Fmoc-Asp(OBu$_t$), Fmoc-Gln(Trt), Fmoc-Leu, Fmoc-Leu, Fmoc-Orn(Boc), Fmoc-Arg(Pbf), Fmoc-Ala, Fmoc-Ser(Bu$_t$), Fmoc-Leu, Fmoc-Gln(Trt), Fmoc-Abu, Fmoc-Leu, Fmoc-Val, Fmoc-Orn(Boc), Fmoc-Thr(Bu$_t$), Fmoc-Phe, Fmoc-Ser(Bu$_t$),Fmoc-Asn(Trt),Fmoc-Thr(Bu$_t$), Fmoc-Phe, Fmoc-Ile, Fmoc-Ala, Fmoc-Asp(OBu$_t$), Fmoc-DAla, Fmoc-N-Me-Tyr(Bu$_t$). After the final coupling, the yield of protected N-Me-Tyr(Bu$_t$)-DAla-Asp(OBu$_t$)-Ala-Ile-Phe-Thr-Asn(Trt)-Ser(tBu)-Tyr(Bu$_t$)-Arg(Pbf)-Orn(Boc)-Val-Leu-Abu-Gln(Trt)-Leu-Ser(Bu$_t$)-Ala-Arg(Pbf)-Orn(Boc)-Leu-Leu-Gln(Trt)-Asp(OBu$_t$)-Ile-Nle-Asp(OBu$_t$)-Arg(Pbf)-{3-[methyl-amino)-methyl]-indol-1 yl}acetyl AM peptide-resin was 11.92 g. The product was then treated with 120 ml of mixed reagent and scavengers containing TFA/Phenol/p-Cresol/H$_2$O (95:1:1:3 by volume) at room temperature for 3 hrs. The crude peptide MR-409 was precipitated with tert-butyl methyl ether, washed and dried and yielded 8.74 g product. The crude MR-409 was then analyzed by HPLC and mass spectrometry (FIG. 6, Group II).

(III) Five analogs with C-terminal additional Apa30, Gab30 or Gab31 hGHRH(1-29)NH2 listed in Table 11 (Group III) were synthesized by using a Boc method on MBHA resin as described in (I), or using Fmoc synthesis on {3-[methyl-amino)-methyl]-indol-1-yl}acetyl AM resin as described in (II). The MR peptides listed Table 11 correspond to the following peptides: MR-351(P-20351); MR-356(P-20356); MR-361(P-20361); MR-367(P-20367); MR-401(P-27401); MR-403(P-27403); MR-404(P-27404); MR-405(P-27405); MR-406(P-27406); MR-407(P-27407); MR-408(P-27408); MR-409(P-27409); MR-410(P-27410); MR-420(P-28421); MR-421(28421); MR-326(P-22326): MR-327(P-22327); MR-502(P-25502); MR-504(P-25504); MR-702(P-29702).

TABLE 11

Chemical structures of new hGHRH(1-29) agonists and their calculated molecular weight by mass spectrometry Group I: C-terminal Agm analogs of hGHRH(1-29)NH$_2$

| Peptide | Position of residue[a] | | | | | | | | | | LC-MS | |
|---|---|---|---|---|---|---|---|---|---|---|---|---|
| | 1 | 2 | 6 | 8 | 12 | 15 | 21 | 27 | 28 | 29 | MW cal[b] | [M + H][c] |
| JI-38 | Dat | Ala | Phe | Gln | Orn | Abu | Orn | Nle | Asp | Agm | 3321.85 | 3322.81 |
| MR-351 | Ac—Me-Tyr | D-Ala | — | — | — | — | — | — | — | — | 3393.90 | 3393.94 |
| MR-356 | N—Me-Tyr | — | — | — | — | — | — | — | — | — | 3351.89 | 3352.08 |
| MR-361 | N—Me-Tyr | D-Ala | — | — | — | — | — | — | — | — | 3351.89 | 3352.81 |
| MR-367 | N—Me-Tyr | D-Ala | — | Asm | — | — | — | — | — | — | 3337.87 | 3338.82 |

[a]Non-coded amino acids and acyl groups used in the analog peptides are abbreviated as follows: Abu, alpha-aminobutanoyl; Agm, agmatine; N—Me-Tyr, N-methyl-tyrosine;
[b]MW cal indicates calculated molecular weight of GHRH agonists.
[c][M + H] indicates detected molecular weight by Agilent 6210 time-of-flight LC/MS TABLE 11-continued Chemical structures of new hGHRH(1-29) agonists and their calculated molecular weight by mass spectrometry Group II: C-terminal methylamide and ethylamide analogs of hGHRH(1-29)NH$_2$

| Peptide | 1 | 2 | 6 | 8 | 12 | 15 | 21 | 27 | 28 | 29 | | MW cal[b] | [M+H][c] |
|---|---|---|---|---|---|---|---|---|---|---|---|---|---|
| JI-38 | Dat | Ala | Phe | Gln | Orn | Abu | Orn | Nle | Asp | Agm | | 3322.85 | 3322 |
| MR-401 | — | D-Ala | — | — | — | — | — | — | — | D-Arg | —NH—CH$_3$ | 3378.87 | 3379 |
| MR-403 | N—Me-Tyr | D-Ala | — | — | — | — | — | — | — | Arg | —NH—CH$_3$ | 3407.9 | 3408 |
| MR-404 | N—Me-Tyr | D-Ala | Fpa5 | — | — | — | — | — | — | Arg | —NH—CH$_3$ | 3497.85 | 3498 |
| MR-405 | N—Me-Tyr | — | — | — | — | — | — | — | Ser | Arg | —NH—CH$_3$ | 3380.91 | 3381 |
| MR-406 | N—Me-Tyr | — | — | — | — | — | — | — | — | Arg | —NH—CH$_3$ | 3408.91 | 3409 |
| MR-407 | — | — | — | — | — | — | — | — | — | Arg | —NH—CH$_3$ | 3378.88 | 3379 |
| MR408 | — | D-Ala | — | — | — | — | — | — | — | Arg | —NH—CH$_3$ | 3378.88 | 3379 |
| MR-409 | N—Me-Tyr | D-Ala | — | Asn | — | — | — | — | — | Arg | —NH—CH$_3$ | 3394.89 | 3395 |
| MR-410 | N—Me-Tyr | D-Ala | — | Thr | — | — | — | — | — | Arg | —NH—CH$_3$ | 3381.90 | 3382 |
| MR-420 | N—Me-Tyr | D-Ala | — | — | — | — | — | — | — | Arg | —NH—CH$_2$CH3 | 3422.93 | 3423 |
| MR-421 | N—Me-Tyr | D-Ala | — | Asn | — | — | — | — | — | Arg | —NH—CH$_2$CH3 | 3408.91 | 3409 |

[a]Non-coded amino acids and acyl groups used in the analog peptides are abbreviated as follows: Abu, alpha-aminobutanoyl; Agm, agmatine; Dat, des-amino-tyrosine; Fpa5, pentafluoro-Phe; N—Me-Tyr, N-methyl-tyrosine;
[b]MW cal indicates calculated molecular weight of GHRH agonists.
[c][M + H] indicates detected molecular weight by Agilent 6210 time-of-flight LC/MS Group III: C-terminal elongated analogs of hGHRH(1-29)NH$_2$

| Peptide | 1 | 2 | 6 | 8 | 12 | 15 | 21 | 27 | 28 | 29 | 30 | 31 | MW cal[b] | [M + H][c] |
|---|---|---|---|---|---|---|---|---|---|---|---|---|---|---|
| JI-38 | Dat | Ala | Phe | Gln | Orn | Abu | Orn | Nle | Asp | Agm | | | 3321.85 | 3321.81 |
| MR-326 | N—Me-Tyr | D-Ala | — | — | — | — | — | — | — | Arg | Apa-NH$_2$ | | 3493.96 | 3493.98 |
| MR-327 | — | — | — | — | — | — | — | — | — | Arg | Apa-NH$_2$ | | 3463.93 | 3464.96 |
| MR-502 | — | D-Ala | Fpa5 | Asn | — | — | — | — | Ser | Arg | Gab-NH$_2$ | | 3497.86 | 3499.93 |
| MR-504 | — | D-Ala | — | Asn | — | — | — | — | Ser | Arg | Gab-NH$_2$ | | 3420.91 | 3422.99 |
| MR-702 | — | D-Ala | — | Asn | — | — | — | — | Ser | Arg | Gln | Gab-NH$_2$ | 3538.04 | 3539.03 |

[a]Non-coded amino acids and acyl groups used in the analog peptides are abbreviated as follows: Abu, alpha-aminobutanoyl; Agm, agmatine; Apa, 5-aminopentanoyl; Dat, des-amino-tyrosine; Fpa5, pentafluoro-Phe; Gab, gamma-amino-butanoyl; N—Me-Tyr, N-methyl-tyrosine;
[b]MW cal indicates calculated molecular weight of GHRH agonists.
[c][M + H] indicates detected molecular weight by Agilent 6210 time-of-flight LC/MS The purification of the crude peptides was performed on a Beckman System Gold HPLC system (Beckman Coulter, Inc., Brea, Calif.) equipped with 127P solvent Module, model 166P UV-VIS Detector, using an XBridge™ reversed phase column (10×250 mm, packed with C18 silica gel, 300 Å pore size, 5 µm particle size (Waters Co., Milford, Mass.). The peptides were eluted with a solvent system consisting of solvent A (0.1% aqueous TFA) and solvent B (0.1% TFA in 70% aqueous acetonitrile (MeCN)) in a linear gradient mode of 30-55% of solvent B for 120 min at a flow rate of 5 ml/min. The eluent was monitored at 220 and 280 nm, and the fractions were examined by analytical HPLC using a Hewlett-Packard Model HP-1090 liquid chromatograph and pooled to give maximum purity. Analytical HPLC was carried out on a Supelco Discovery HS C18 reversed-phase column (2.1×50 mm, C18, 300 Å pore size, 3 µm particle size; Supelco Bellefonte, Pa.) using gradient elution from 40-80% B for 40 mins with a solvent system consisting of solvent A and B, defined above, with a flow rate of 0.2 ml/min. The peaks were monitored at 220 and 280 nm. The peptides were judged to be substantially (>95%) pure by analytical HPLC. Molecular masses were determined by Agilent 6210 time-of-flight mass spectrometry in conjugation with 1200 CapLC (Agilent Technologies 6210 Time of Light LC/MS, Santa Clara, Calif.). Peptides were eluted on an Agilent Zorbax C18 column (0.5×150 mm, 300 Å pore size, 5 µm particle size, Agilent, Santa Clara, Calif.) at a flow rate of 15 µl/min with a linear gradient from 35-85% B for 30 min. Solvent A is 0.1% formic acid (FA), Solvent B was 90% aqueous MeCN/0.1% FA. TOF settings are as follow: Capillary voltage: 4000 V, Drying gas flow: 7 L/min, Drying gas temperature: 300° C., Nebulizer gas: 30 psi, Fragmentor voltage: 350 V.

Determination of GH Releasing Potencies In Vivo

Male Sprague-Dawley rats, weighing 200-250 g, were purchased from Charles River Laboratory (Wilmington, Mass.) and used for experiments. All animal procedures were approved by the Veterans Affairs Animal Care and Use Committee and were conducted in accordance with additional institutional guidelines as well. Briefly, groups of 5-6 animals were used in each experiment. The rats were anesthetized with 50 mg/kg of sodium pentobarbital (Nembutal, Lundbeck Inc., Deerfield, Ill.). Twenty min after inducing anesthesia, GHRH(1-29)NH$_2$, JI-38, or new analogs were injected into the animals intravenously (i.v.) or subcutaneously (s.c.). The peptides were dissolved in 0.01 M acetic acid to get 1 µg/µl stock solution, and then diluted with 5% mannitol. Control rats received 5% mannitol only. Blood samples were collected from the jugular vein at selected times and were used for serum preparation. Concentrations of GH in rat sera were determined by ELISA. The relative potencies of tested peptides were calculated using GHRH (1-29)NH$_2$ and JI-38 for comparison, whose potency was defined as 1. The equivalent dosage of GHRH(1-29)NH$_2$ to reach the same level of serum growth hormone release after injection of the specific tested peptide was determined from a GHRH(1-29)NH$_2$ standard curve using Origin 6.0 software. The relative potency of the tested compounds was the ratio of GHRH(1-29)NH$_2$ equivalence over the actual dosage used for injection.

Evaluation of Receptor Binding In Vitro

The binding of GHRH(1-29) analogs to membrane receptors of human anterior pituitary cells was determined using $^{125}$I-labeled [His$^1$,Nle$^{27}$]-hGHRH(1-32)NH$_2$ as a radioligand. Normal human pituitary was purchased from the National Hormone and Peptide Program (UCLA Medical Center, Torrance, Calif.). Preparation of human pituitary membrane fraction and receptor binding of GHRH(1-29) agonists were performed by using a sensitive in vitro ligand competition assay. In competitive binding analysis, $^{125}$I-labeled [His$^1$,Nle$^{27}$]-hGHRH(1-32)NH2 (0.2 nM) was displaced by hGHRH agonists at $10^{-6}$-$10^{-12}$ M. The final binding affinities were expressed as IC$_{50}$ values and were calculated by using the LIGAND PC computerized curve-fitting program. Relative affinities were compared to hGHRH(1-29)NH$_2$ and calculated as the ratio of IC$_{50}$ (dose causing 50% inhibition of specific binding to receptors) of the tested peptides to the IC$_{50}$ of the standard.

Cardiac Assays in Rats

Myocardial infarction (MI) model.

MI was induced in female 6-month-old Fischer 344 rats by permanent ligation of left ventricular (LV) anterior descending coronary artery. Animals were randomly assigned to receive placebo or one of the following GHRH agonists (MR-356, MR-361, MR-367, MR-403, MR-404, MR-409 and MR-502) starting 2 hours post-surgery. All treatment (50 µg/kg) was given subcutaneously twice daily for 4 weeks. The Institutional Animal Care and Use committee of the University of Miami approved all protocols and experimental procedures.

Echocardiographic Measurements.

Longitudinal evaluation of LV remodeling was obtained by echocardiographic measurements between baseline and 4 weeks following MI. Echocardiographic assessments were performed in anesthetized rats (1-2% isoflurane inhalation) using a Vevo-770 echocardiogram (Visual Sonics Inc., Toronto, Ontario, Canada) equipped with 25 MHz transducer. Cardiac dimensions were recorded from M-mode images using averaged measurements from 3 to 5 consecutive cardiac cycles. LV end-diastolic and end-systolic volumes and ejection fraction (EF) were calculated from bidimensional long-axis parasternal views taken through the infarcted area. All images were analyzed using Vevo 770 3.0.0 software (Visual Sonics).

Morphometric Analysis.

Slides were prepared with H&E and Masson's trichrome stain to assess cardiac structure and the presence and extent of myocardial scar, respectively. The percentage of infarcted myocardium was calculated.

Hormone Determination

Serum GH was determined using the rat Growth Hormone ELISA kit (ALPCO Diagnostics, Mill Valley, Calif.) according to the manufacturer's instruction. Absorbance at 405 nm was measured by a Victor 3 Multi-label Counter (Perkin-Elmer, Waltham, Md.).

Statistical Analysis

Determination of GH-releasing activity from in vivo experiments was performed by t-test or one-way ANOVA followed by Tukey's test using the computer software Sigma Stat (Jandel, San Rafel, Calif.). Differences were considered significant when p<0.05. For cardiac assays, all values are shown as mean±SEM. Significance was determined by the unpaired Student's t test. For a given parameter, p<0.05 was considered significant. All tests were carried out using GraphPad Prism software (San Diego, Calif., USA) version 5.0 for Windows.

Results

Design and synthesis of new hGHRH(1-29)NH$_2$ agonists

This series of analogs was designed by modifying JI-38, containing the sequence of [Dat$^1$, Gln$^8$, Orn$^{12,21}$, Abu$^{15}$, Nle$^{27}$, Asp$^{28}$, Agm$^{29}$]hGHRH(1-29)NH$_2$, as a model peptide since this analog exhibited high activity in vivo. In each of the new agonistic analogs, Lys$^{12}$ and Lys$^{21}$ were replaced by Orn, Gly$^{15}$ by Abu, and Met$^{27}$ by Nle. In seven of the new peptides (MR-401, MR-407, MR-408, MR-327, MR-502, MR-504, MR-702), Dat(desamino-Tyr) was conserved at the N-terminus, but most analogs had N-Me-Tyr$^1$. In fourteen analogs, Ala$^2$ was substituted by D-Ala, and in one peptide, Ala$^2$ was replaced by D-Abu. Phe at position 6 was substituted by pentafluoro-Phe (Fpa$^5$) in two compounds. Asn in position 8 and Ser at position 28 were either left unchanged or replaced by Gln and Asp, respectively. We focused on modifications at the C-terminus. As shown in Table 11, the three major groups of the new hGHRH agonists had different C-termini: I) Agm$^{29}$; II) Arg$^{29}$-methylamide or Arg$^{29}$-ethylamide, and III) elongated C-terminus with w-amino fatty acid amide, such as Apa$^{30}$-NH$_2$, Gab$^{30}$-NH$_2$ or Gln$^{30}$-Gab$^{31}$-NH$_2$.

Figure 7:
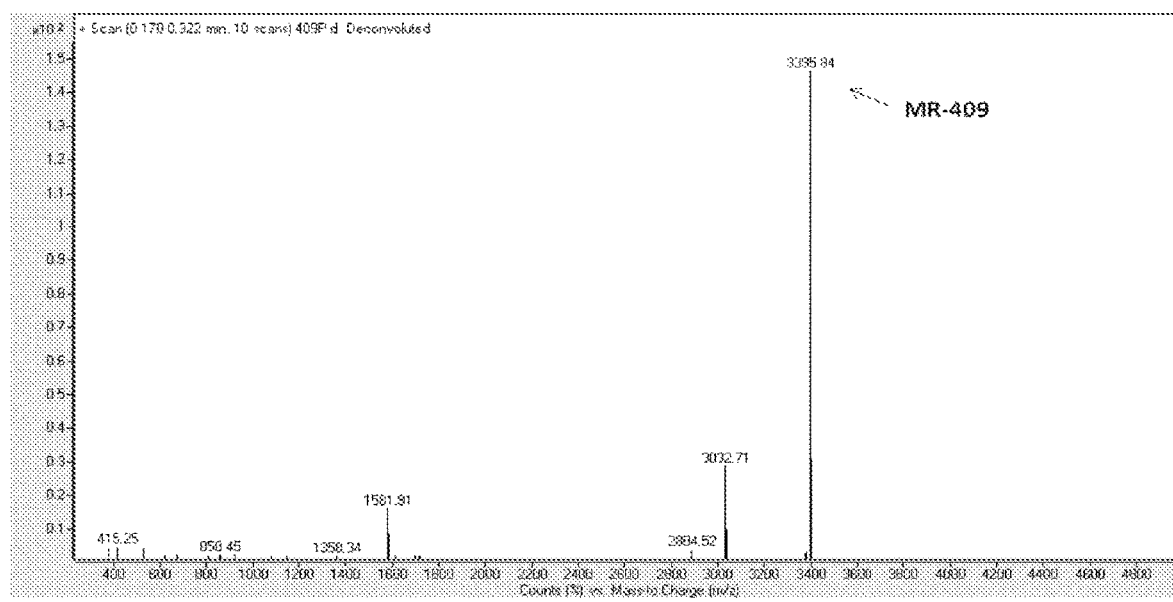
FIG. 7 shows the molecular weight of crude sample MR-409 analyzed by Agilent 6210 time-of-flight LC/MS. Expected molecular weight of MR-409 is 3394.89; detected molecular weight of MR-409 is 3395.84.

The synthesis of C-terminal methylamide peptides on {3-[(methyl-Fmoc-amino)-methyl]-indol-1-yl}acetyl AM resin with Fmoc synthesis was successful. In the case of synthesis of MR-409, the yield of the crude MR-409 methylamide peptide was very high and had good purity (FIG. 6). From 4.4 g of crude MR-409, we obtained 2.1 g peptide with purity over 97%. The total yield calculated from resin was 24%. All synthesized peptides listed in Table 11 were purified by HPLC to receive purity over 95%. Their molecular weights (MW) as determined by mass spectrometry matched very well with their MW calculated from structures (Table 11, FIG. 7).

Effects of New GHRH Analogs on GH Release In Vivo

The GH-releasing effects of the new GHRH agonists in vivo are summarized in Tables 12 and 13. Most novel agonists were found to be more potent than JI-38. After i.v. injections, MR-502 in particular, showed a potency 2.1 and 2.9 fold higher than JI-38 at 5 and 15 minutes, respectively. MR-356, MR-403, MR-504 and MR-702 exhibited slightly improved relative potencies, ranging between 1.1-and 1.6-fold that of JI-38, in the i.v. test (Table 13). After s.c. administration, the relative potency of MR-403 was 2.7- and 4.0-fold higher than that of JI-38 at 15 and 30 minutes, respectively. In s.c. tests, MR-326, MR-327, MR-356, MR-361, MR-367, MR-401, MR-404, MR-405, MR-406, MR-407, MR-409, MR-410, MR-420, MR-421 and MR-502 showed in the range of 1.0- to 4.0-fold higher potencies than JI-38. Some peptides showed increased potency as compared to JI-38 in both i.v. and s.c. tests. These included MR-356, MR-403 and MR-502.

Binding Affinities of New hGHRH Agonists

The binding affinity of analogs to membrane receptors of human anterior pituitary cells was determined by using $^{125}$I-labeled [His$^1$, Nle$^{27}$]hGHRH(1-32)NH$_2$. The relative affinities of analogs were compared to hGHRH(1-29)NH$_2$ as the standard (IC$_{50}$=4.06 nM; accepted as 1.0) and were found to be much higher. Fourteen analogs showed higher binding affinities than JI-38 (Table 14).

Impact of GHRH Agonist on Cardiac Remodeling

Figure 9:
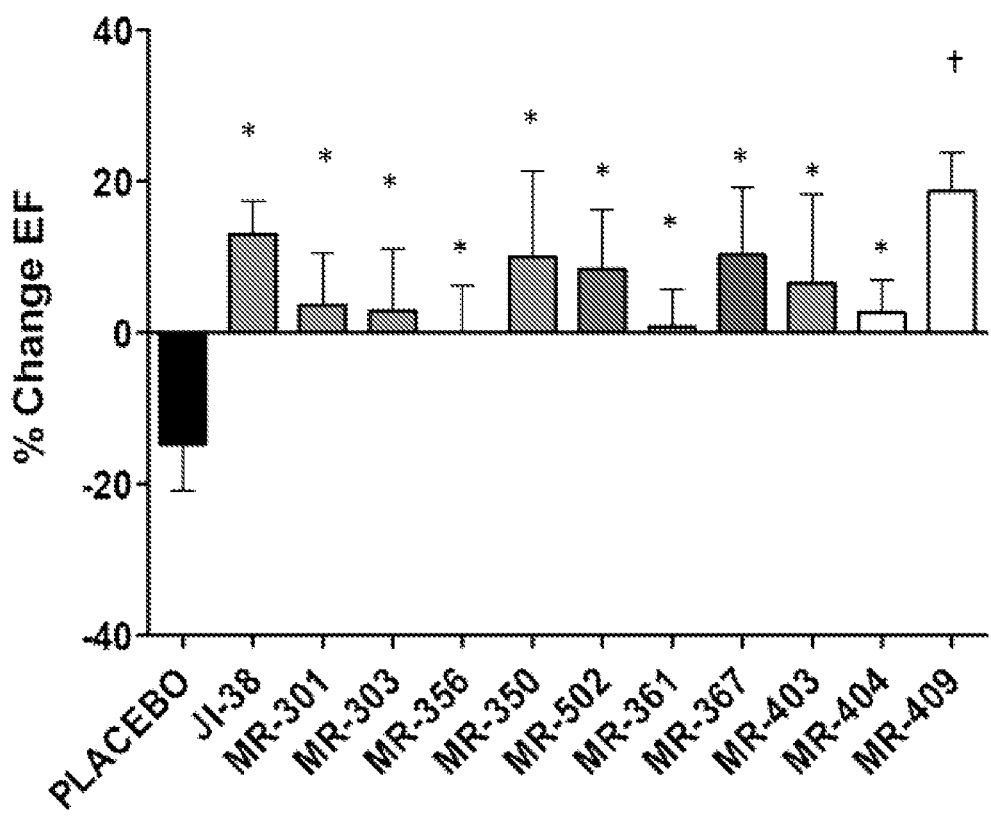
FIG. 9 shows the impact of GHRH agonists on cardiac function. Bar graphs show the percentage of change in ejection fraction (EF %) at 4 weeks relative to day 2 post-MI. All values represent means+SEM. (*p<0.05, †p<0.01 vs.placebo).
Figure 10A:
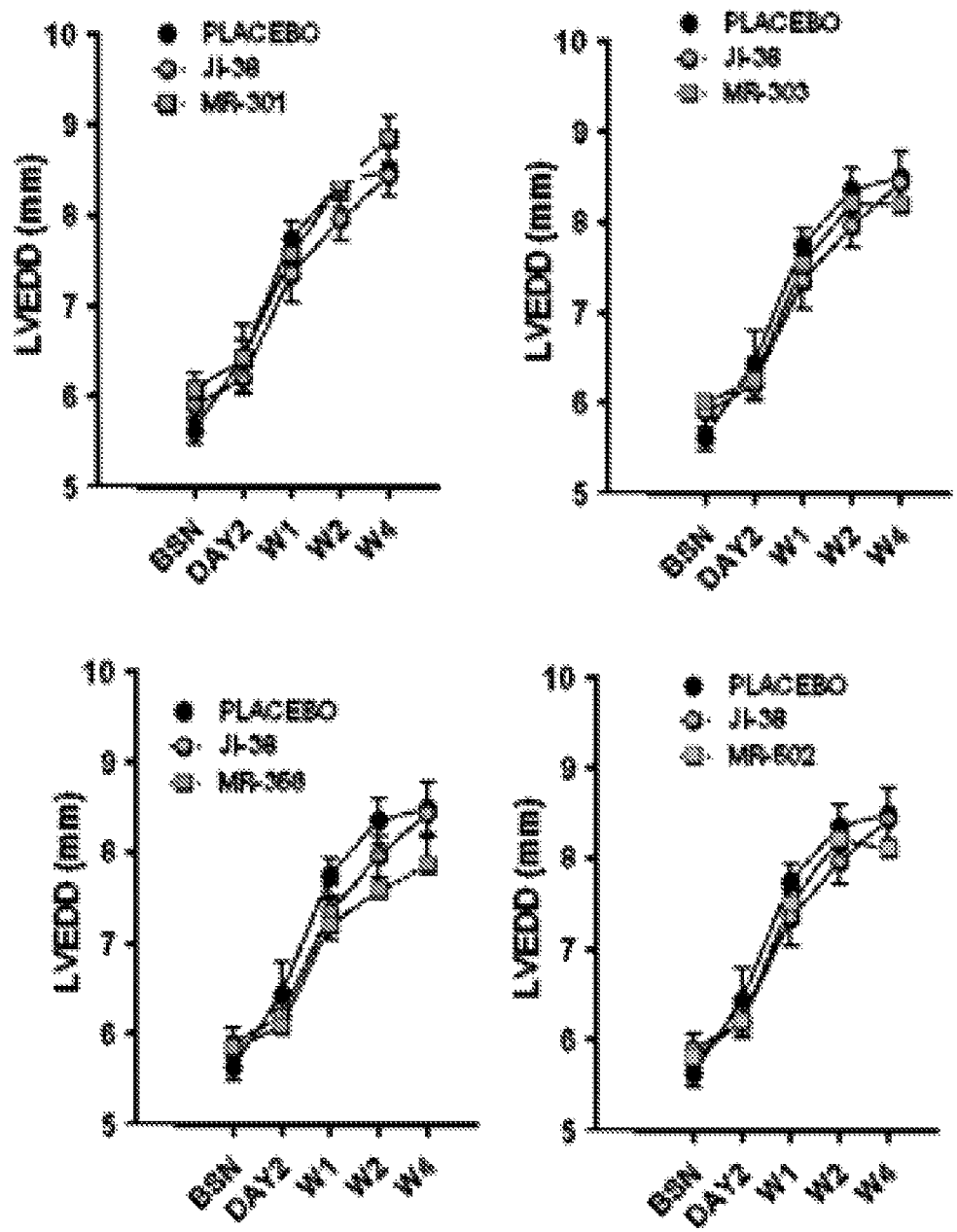
FIG. 10A-D show Left Ventricular End Diastolic Diameter (LVEDD) measurements in rats treated with various GHRH analogs, according to embodiments.
Figure 10B:
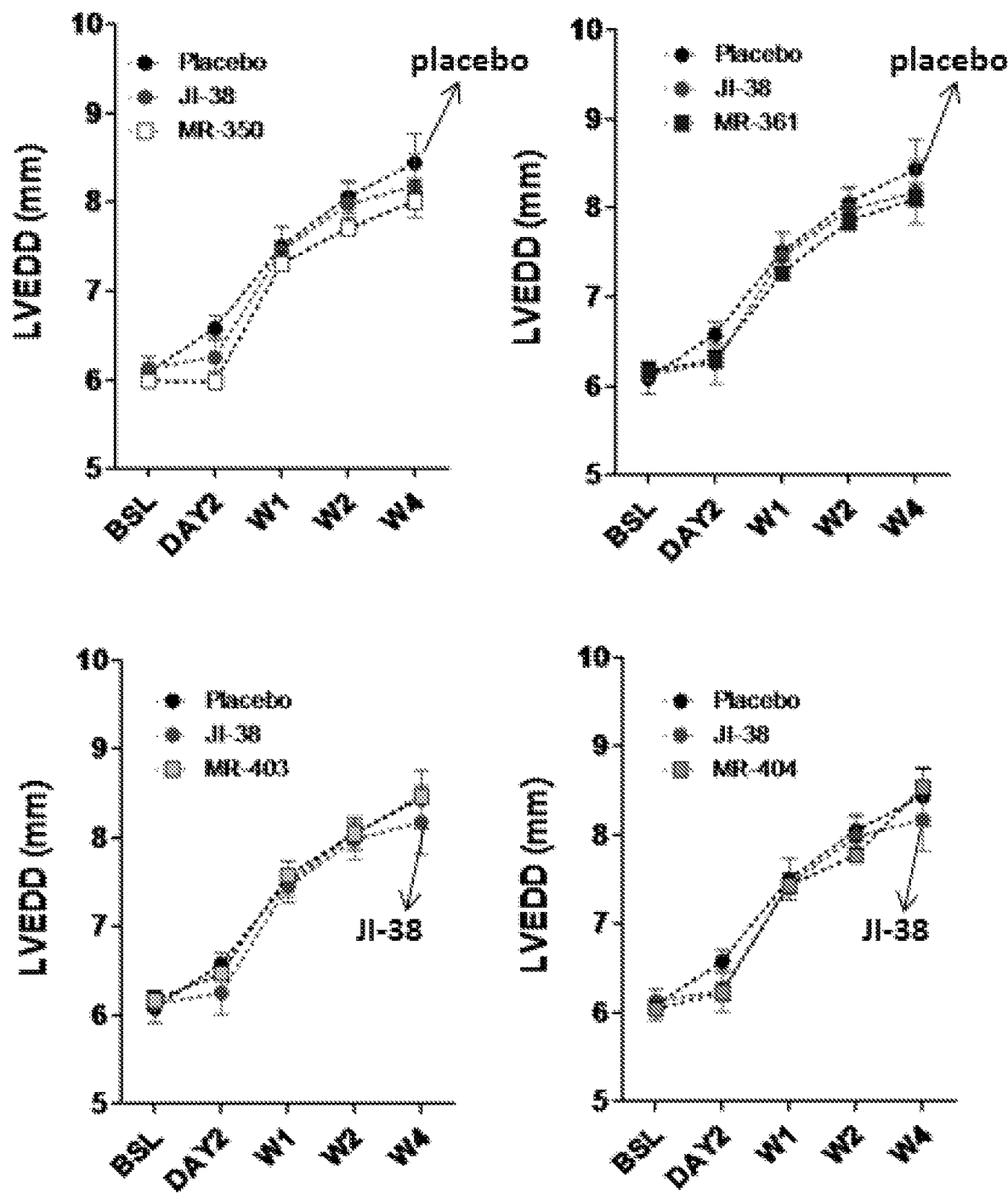
Figure 10C:
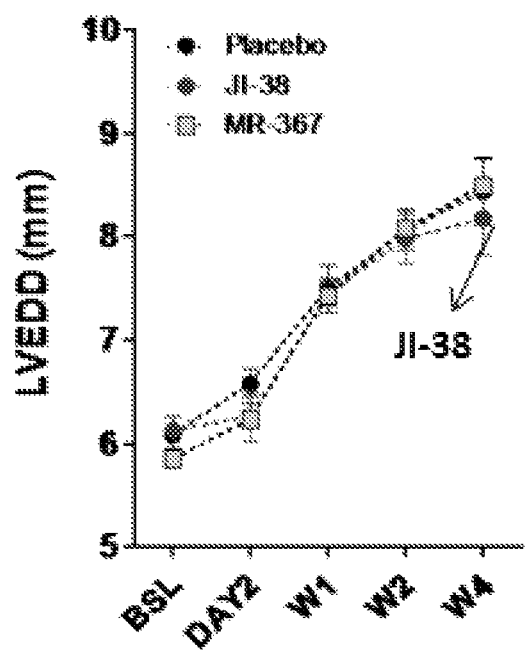
Figure 10C:
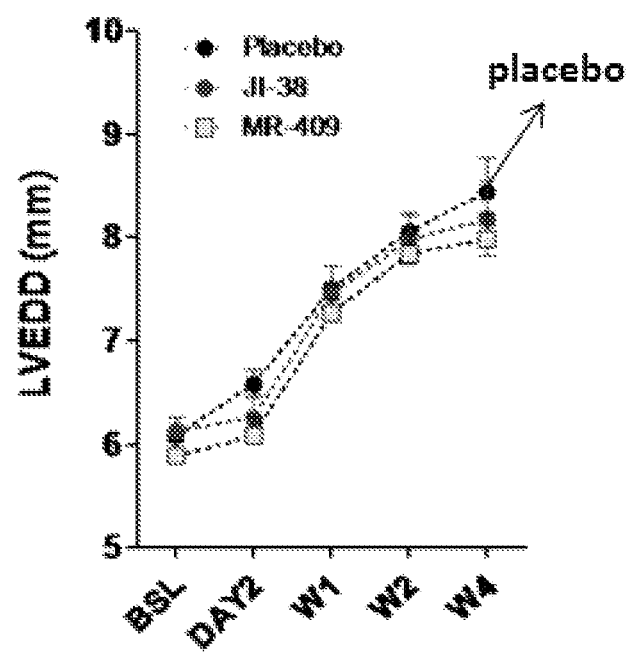
Figure 10D:
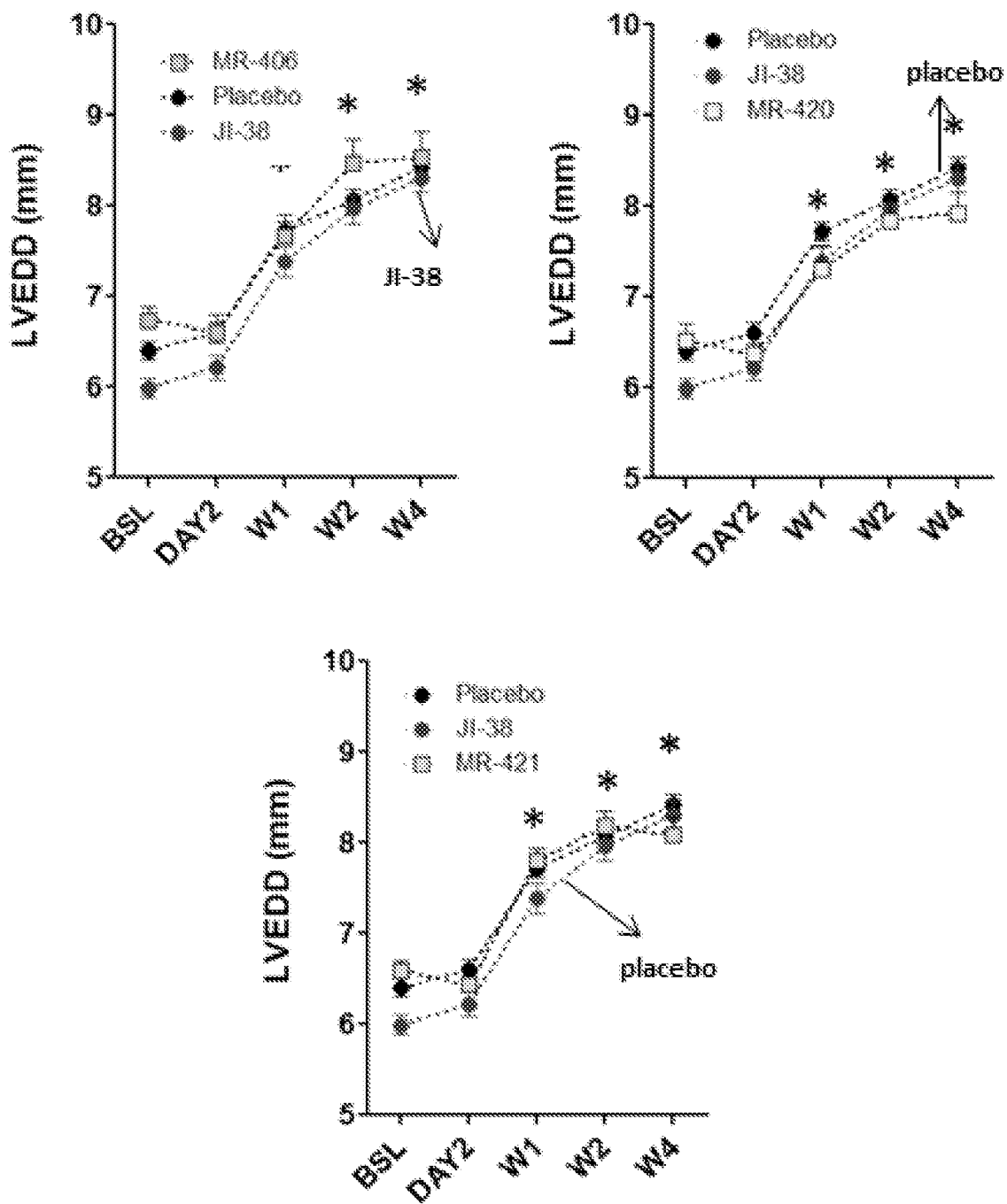
Figure 11A:
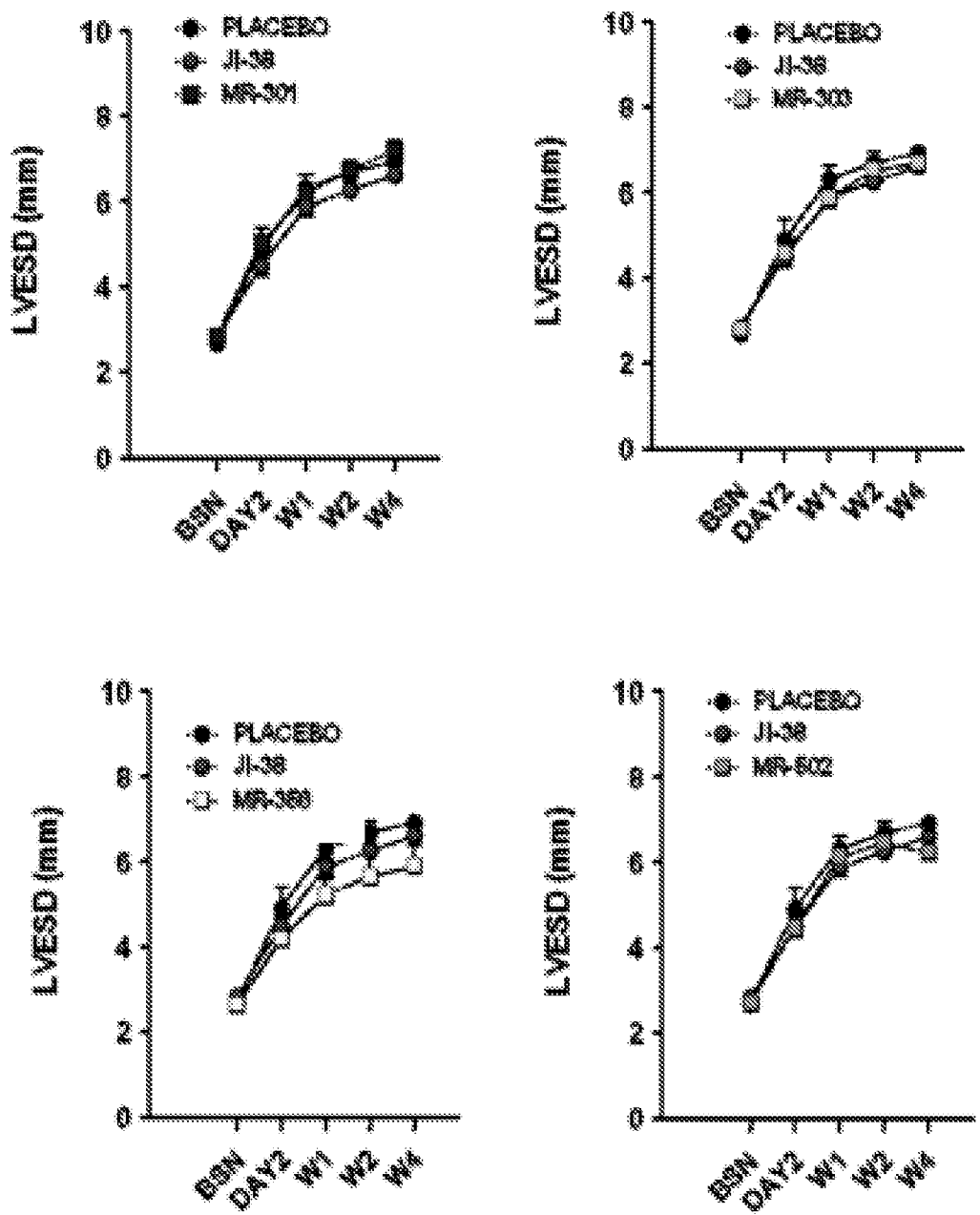
FIG. 11A-D show Left Ventricular End Systolic Diameter (LVESD) measurements in rats treated with various GHRH analogs, according to embodiments.
Figure 11B:
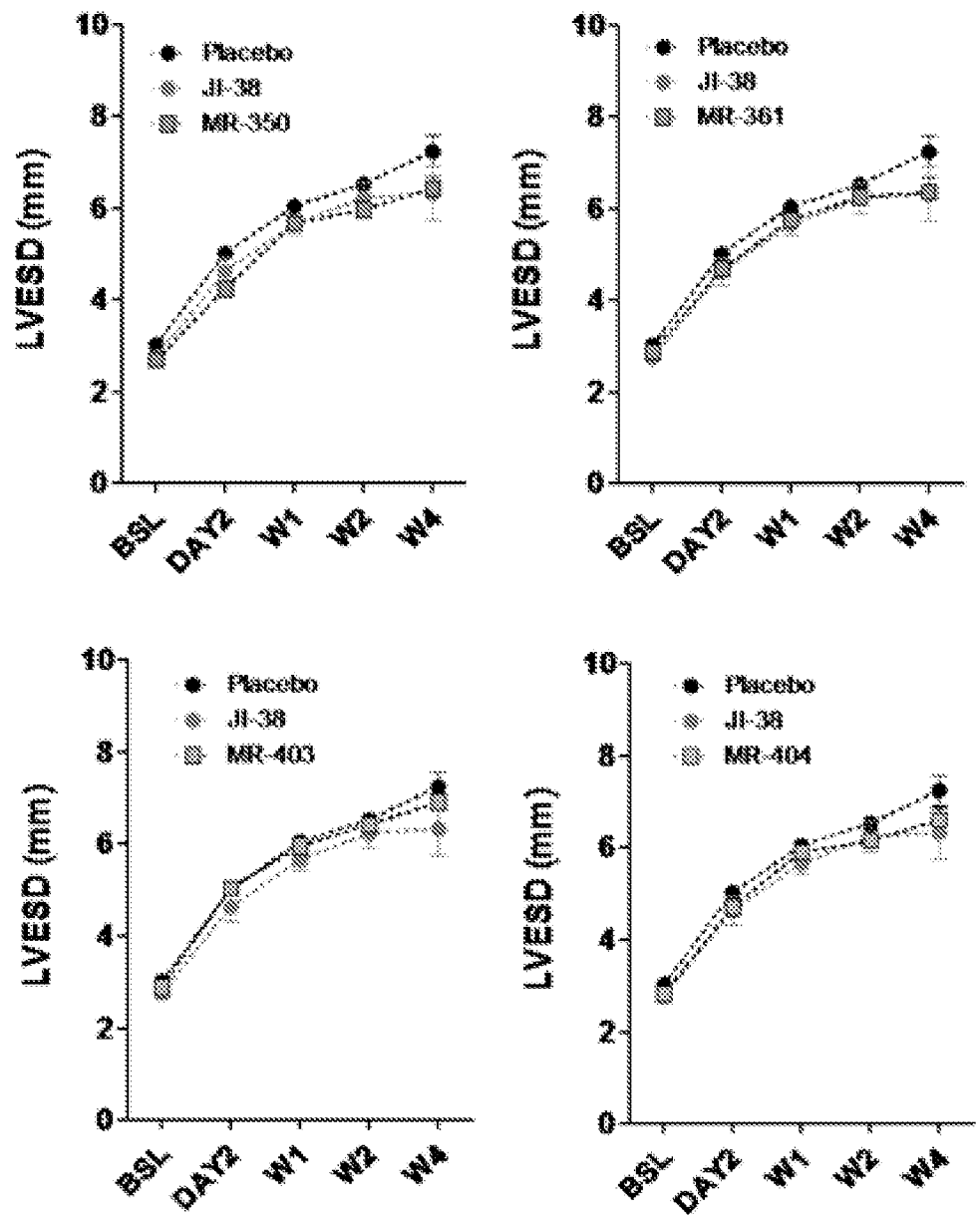
Figure 11C:
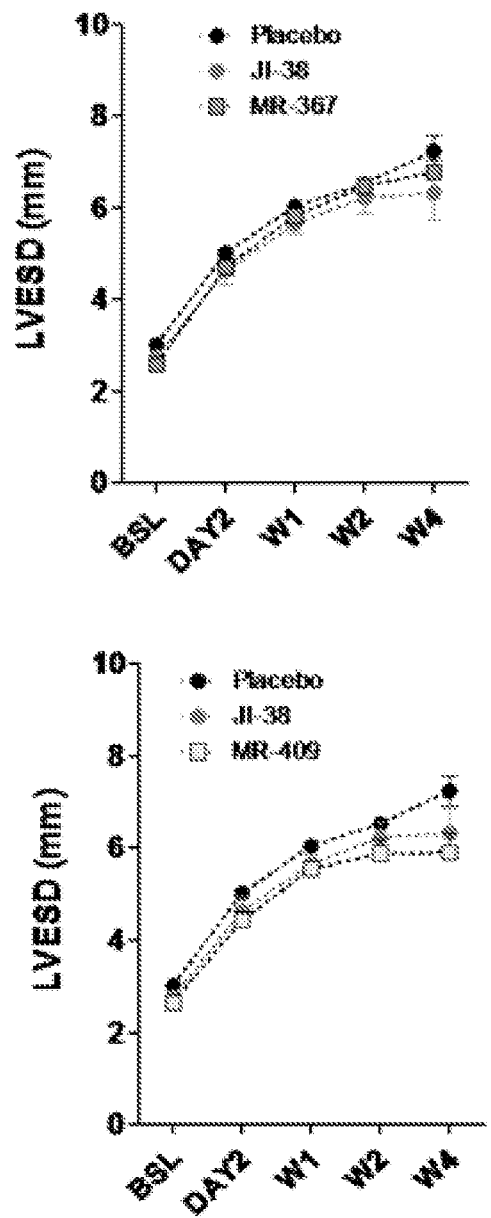
Figure 11D:
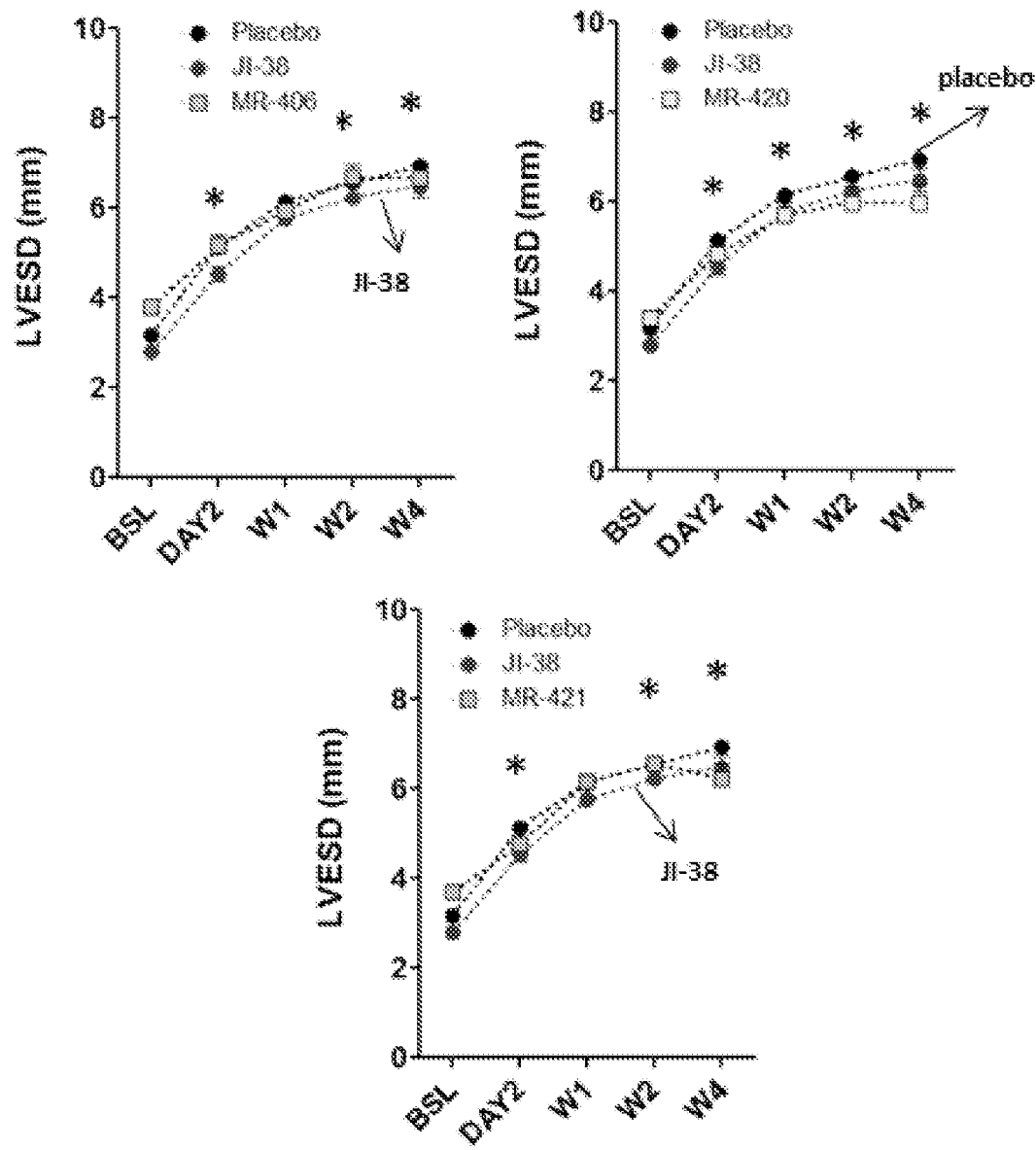
Figure 12A:
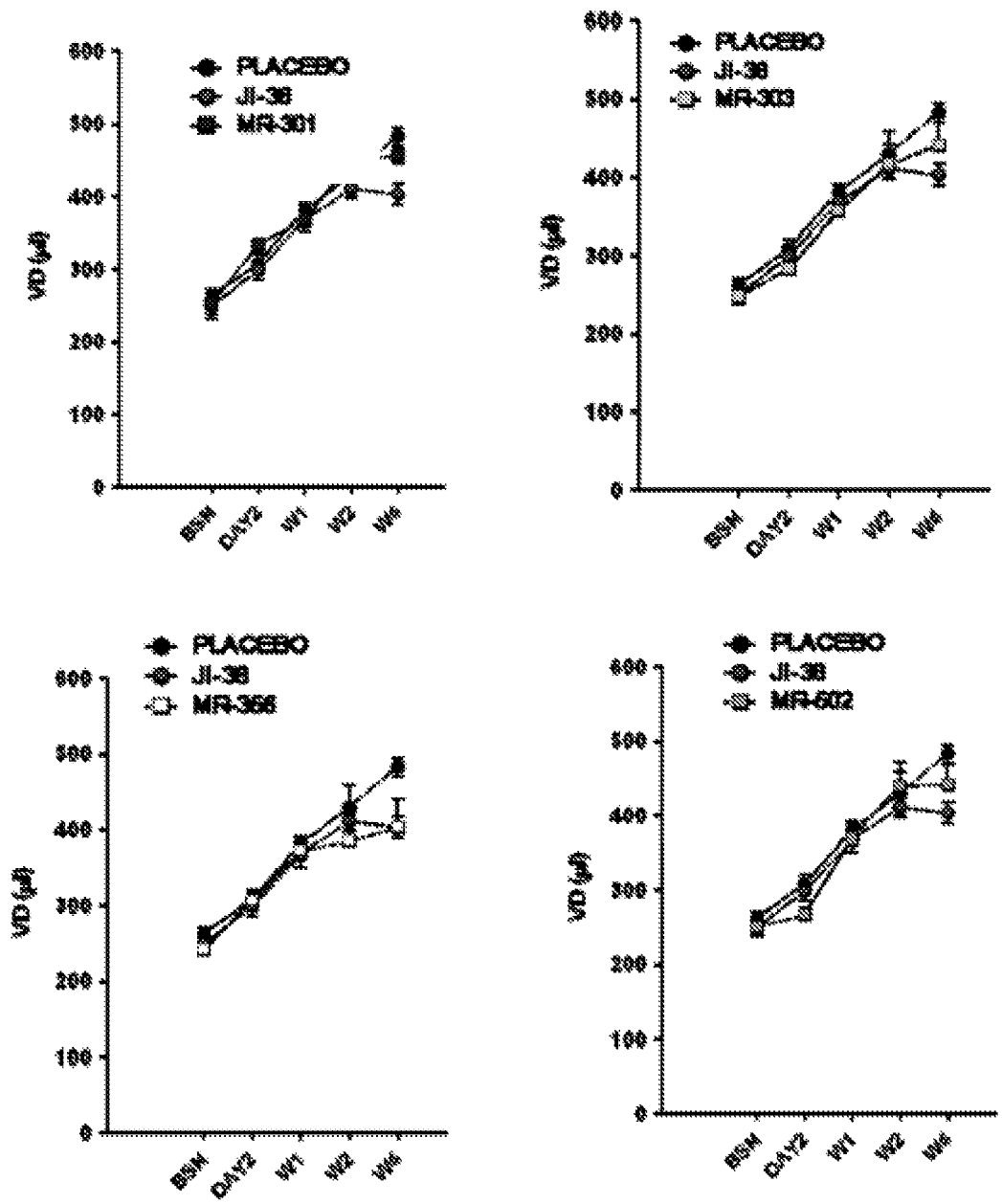
FIG. 12A-D show diastolic volume (VD) measurements in rats treated with various GHRH analogs, according to embodiments.
Figure 12B:
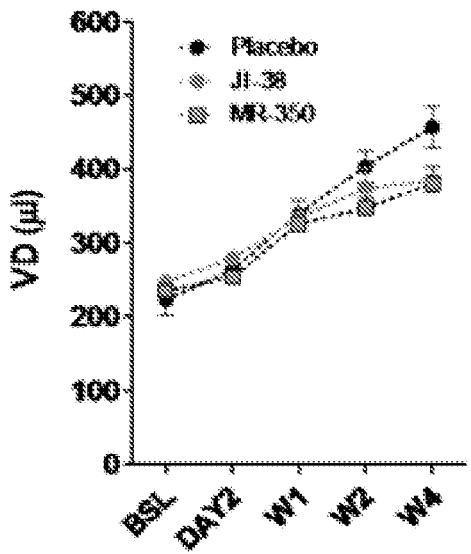
Figure 12B:
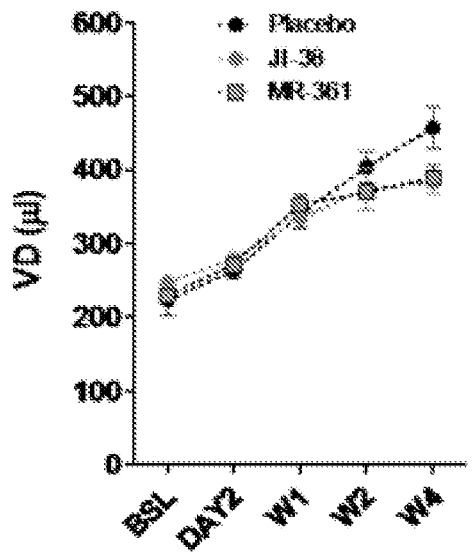
Figure 12B:
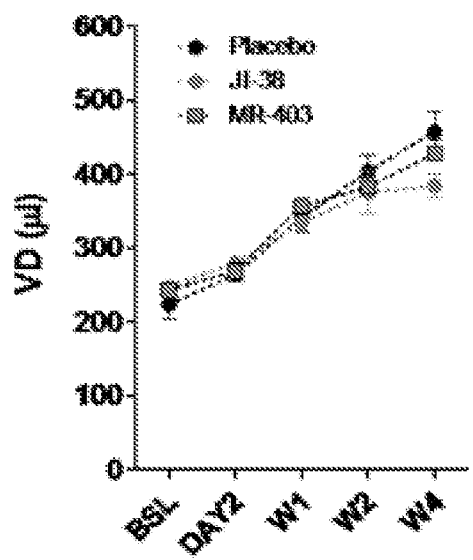
Figure 12B:
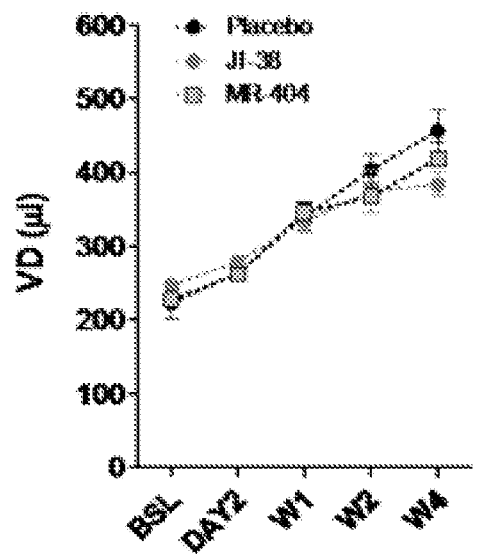
Figure 12C:
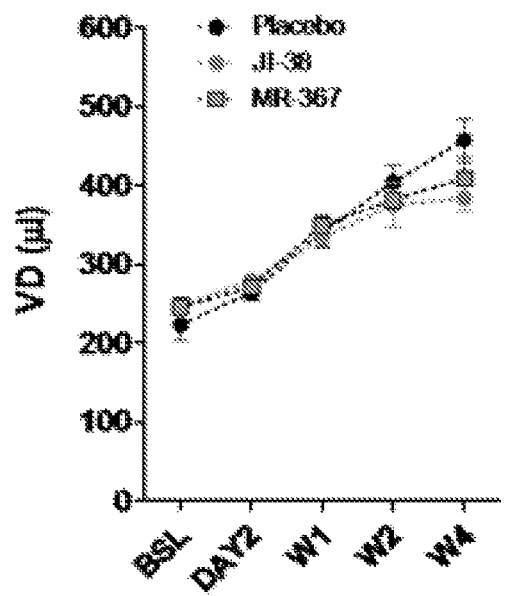
Figure 12C:
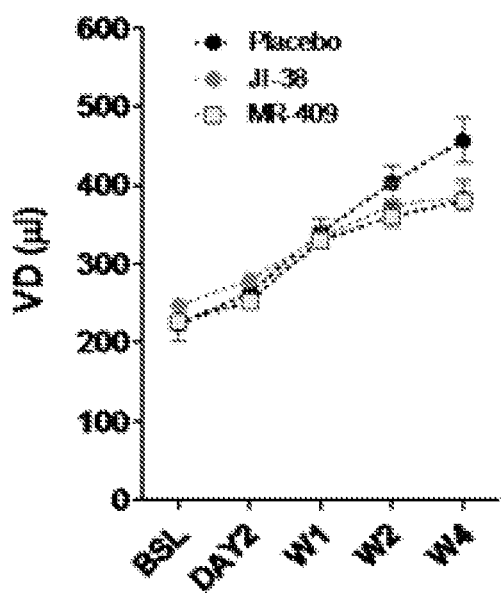
Figure 12D:
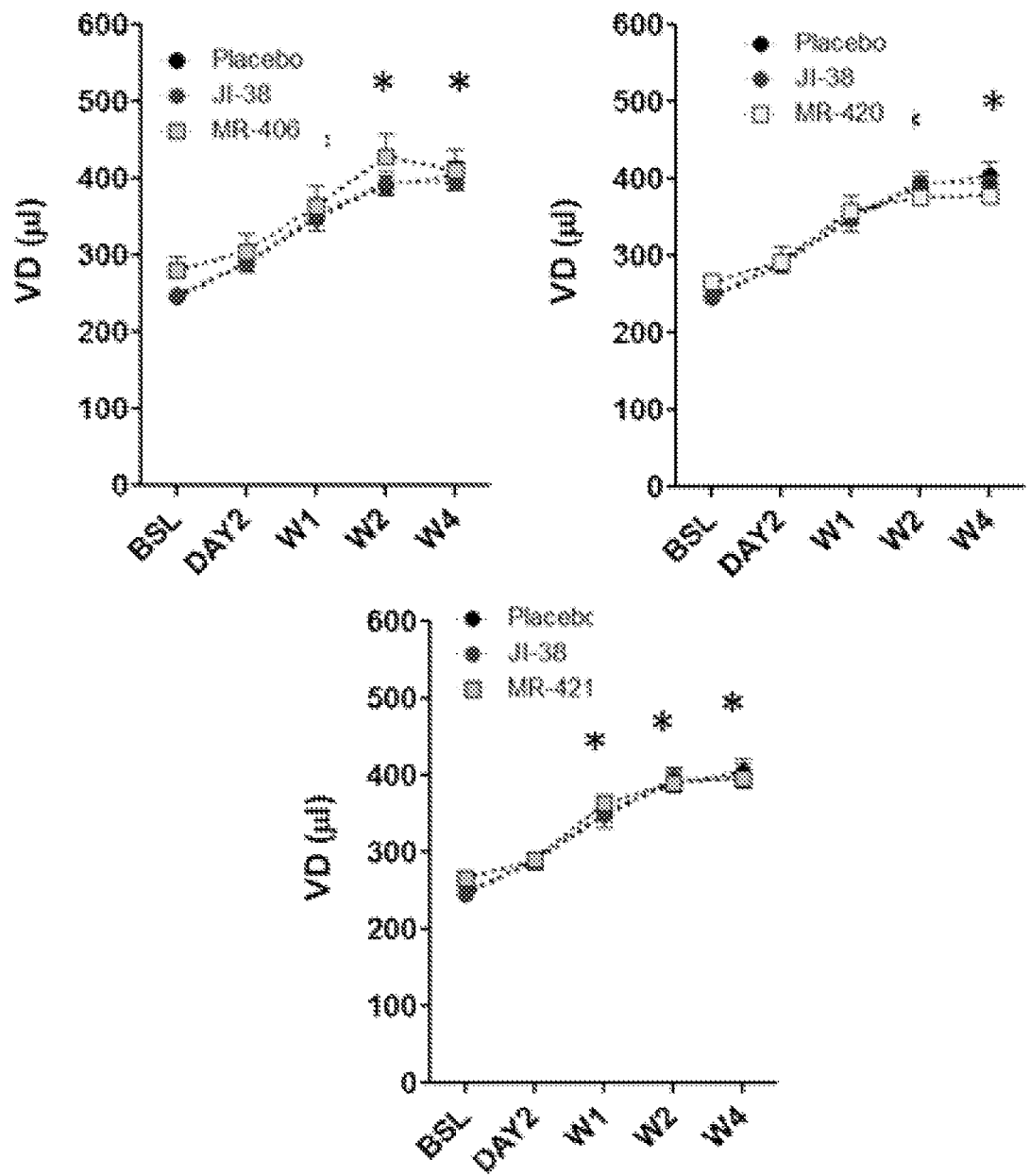
Figure 13A:
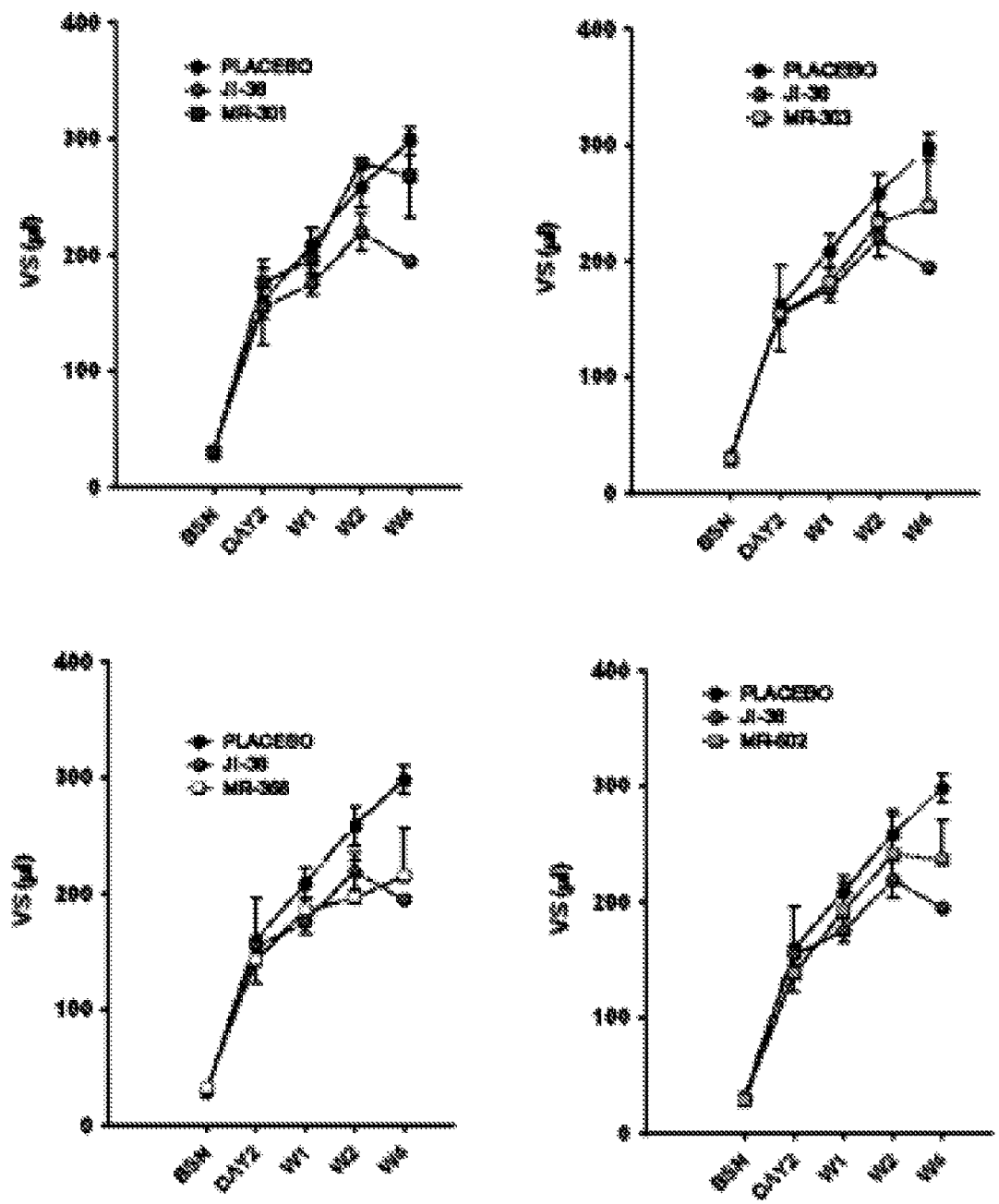
FIG. 13A-D show systolic volume (VS) measurements in rats treated with various GHRH analogs, according to embodiments.
Figure 13B:
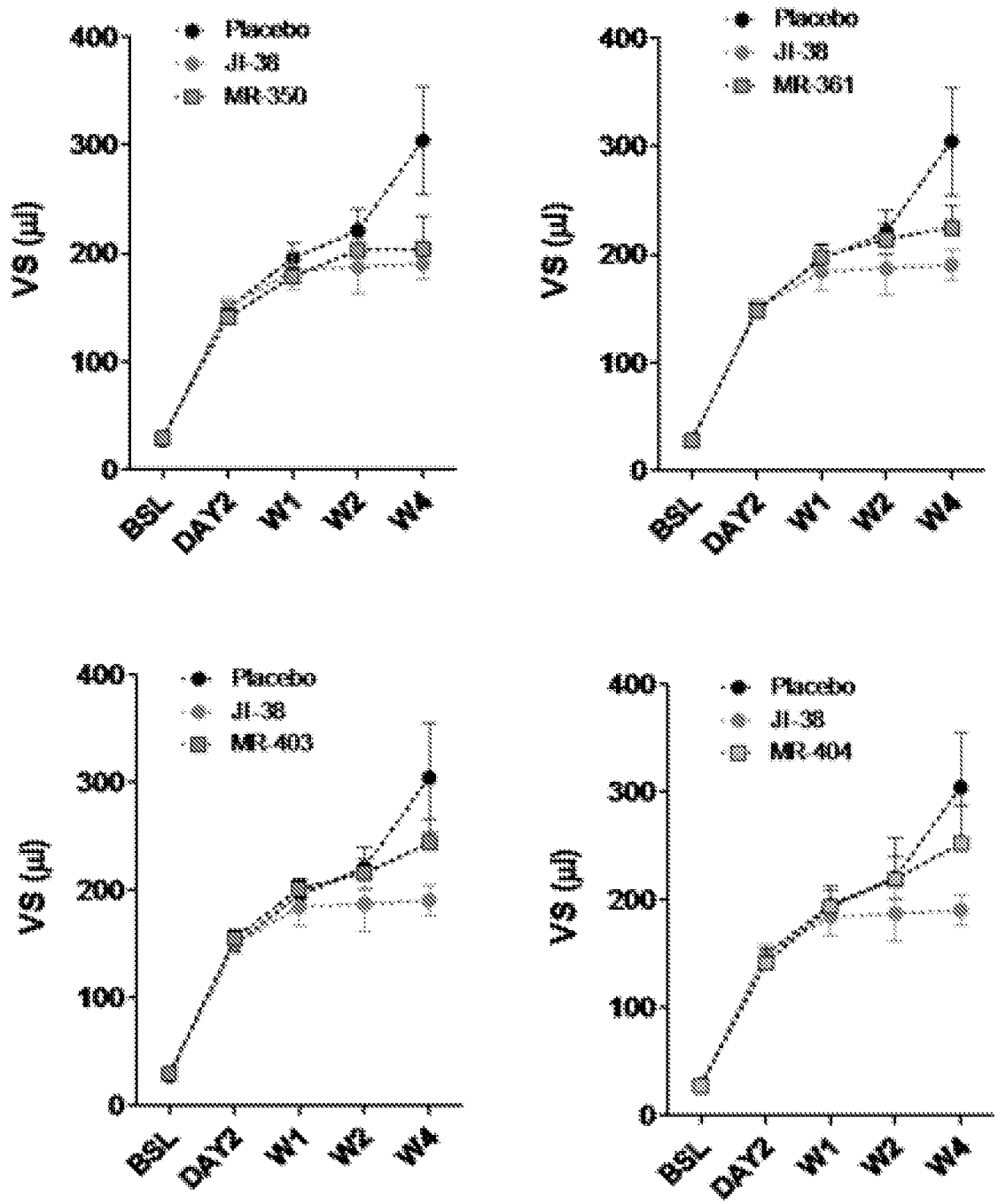
Figure 13C:
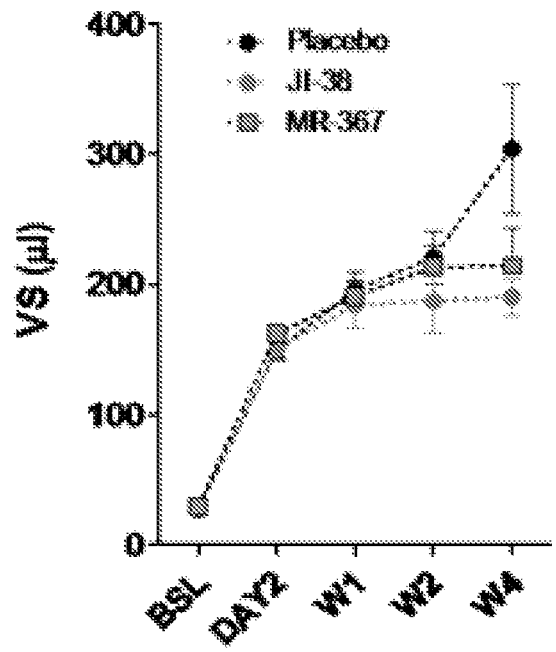
Figure 13C:
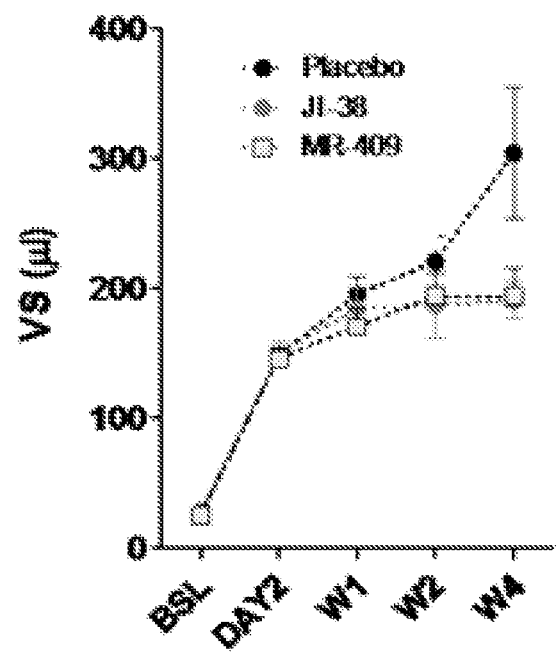
Figure 13D:
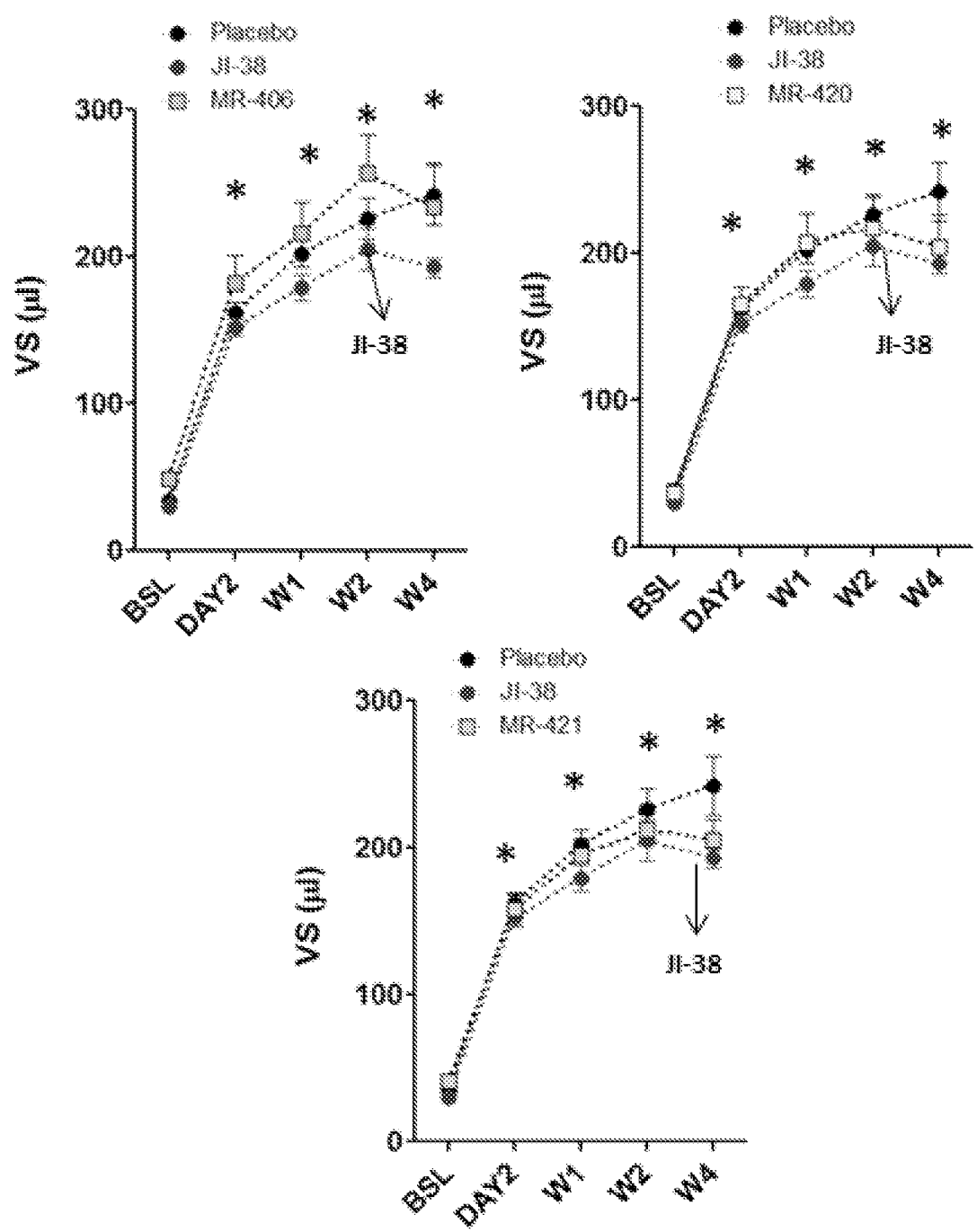
Figure 14A:
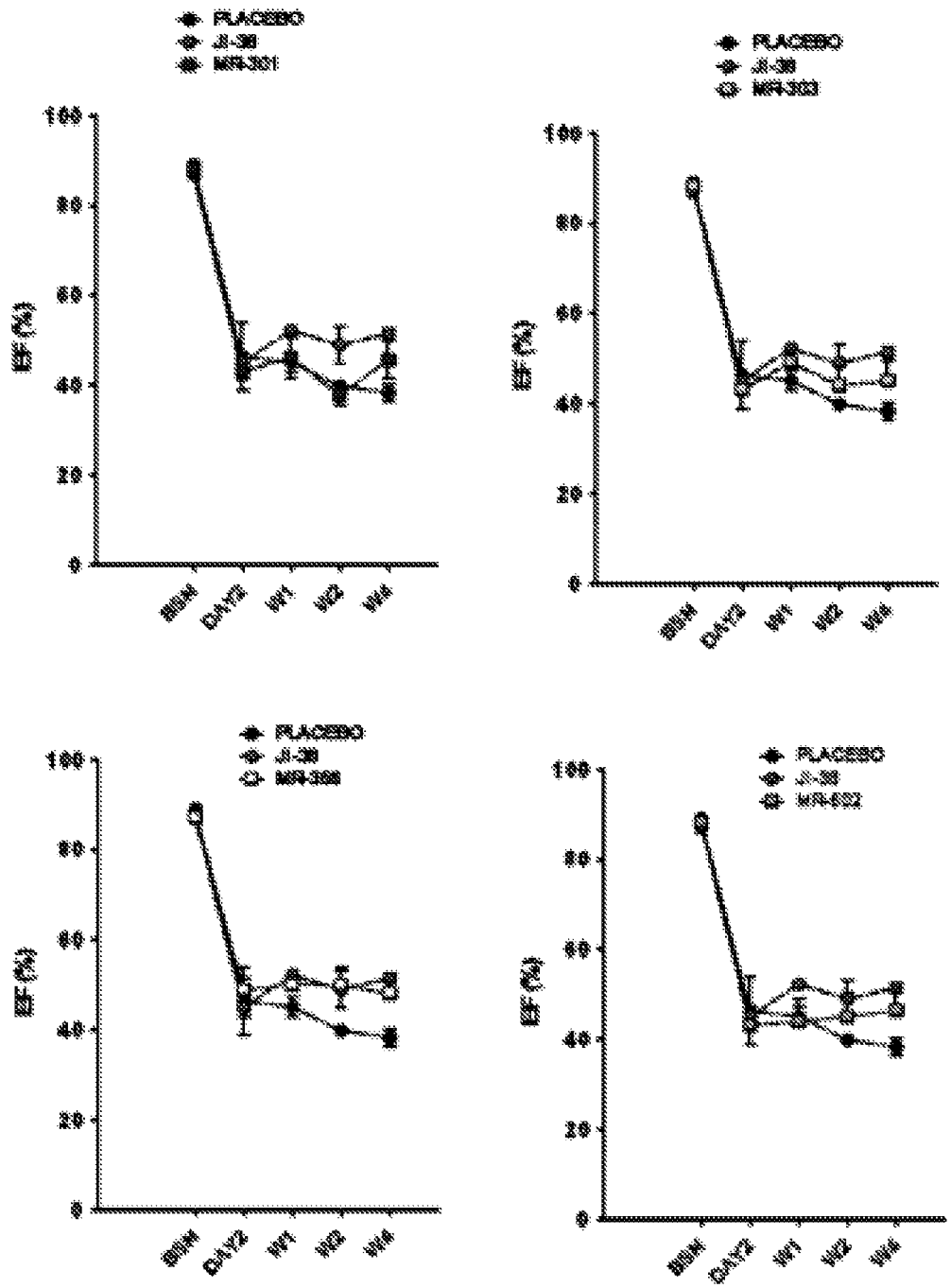
FIG. 14A-D show ejection fraction (EF) measurements in rats treated with various GHRH analogs, according to embodiments.
Figure 14B:
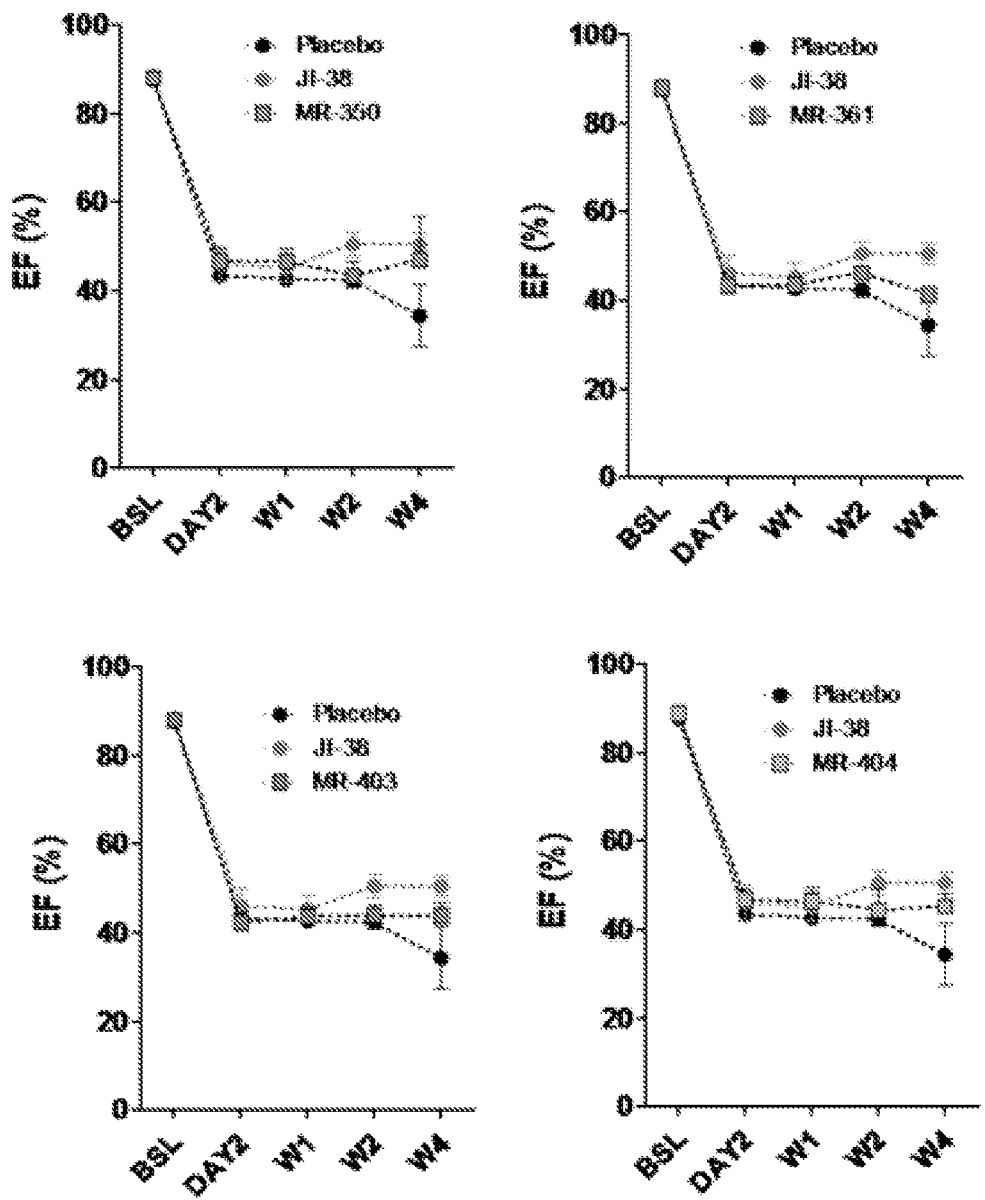
Figure 14C:
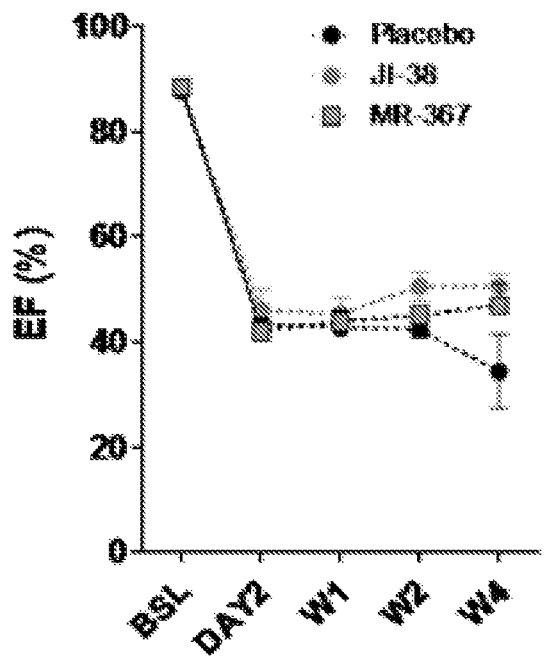
Figure 14C:
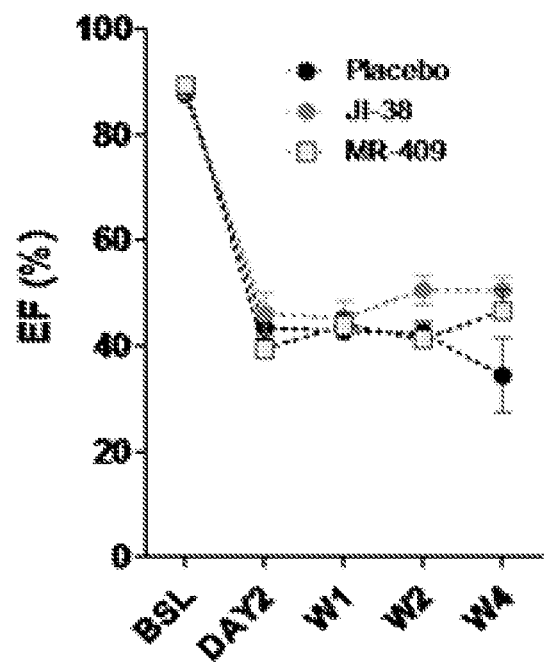
Figure 14D:
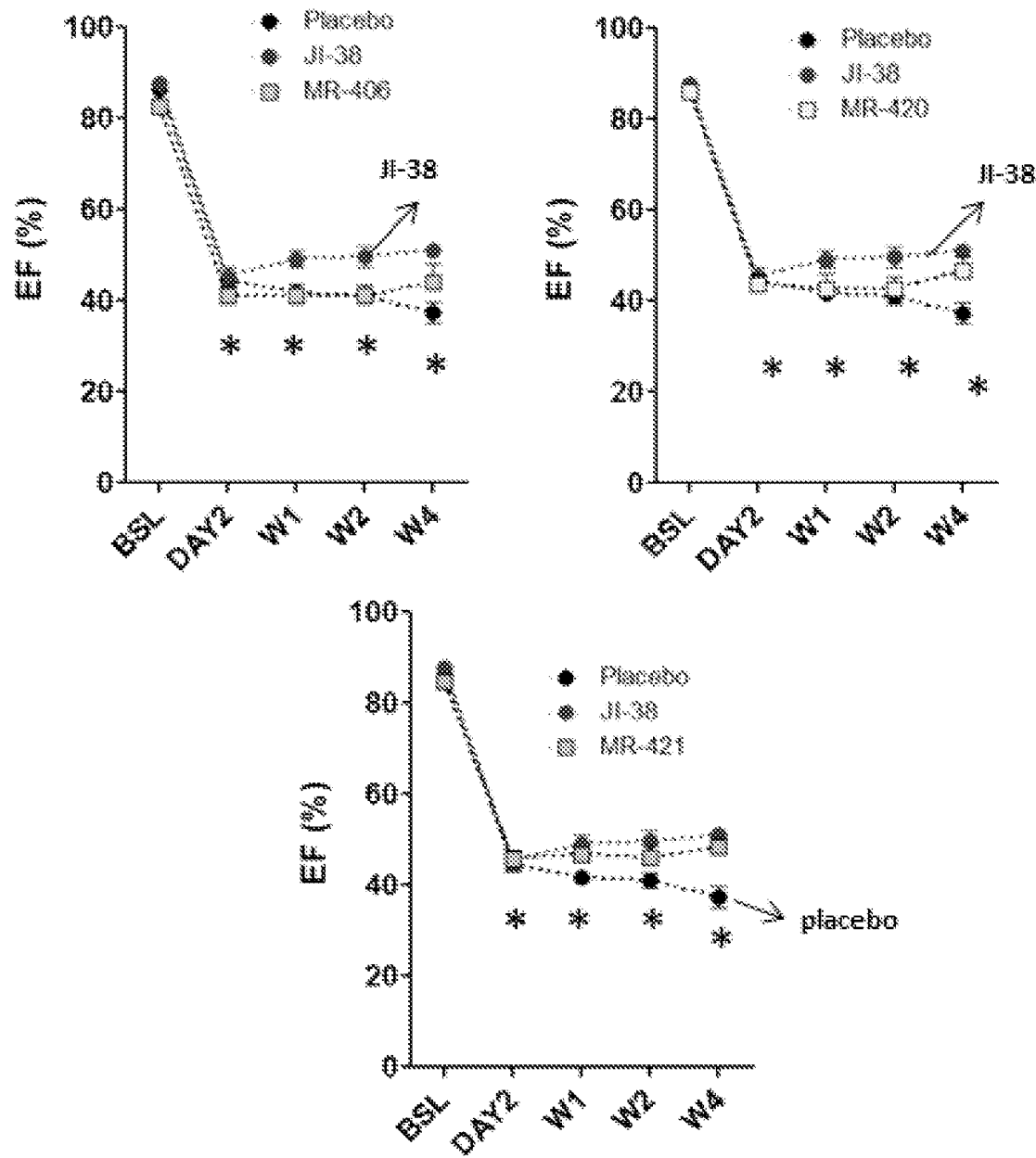
Figure 15A:
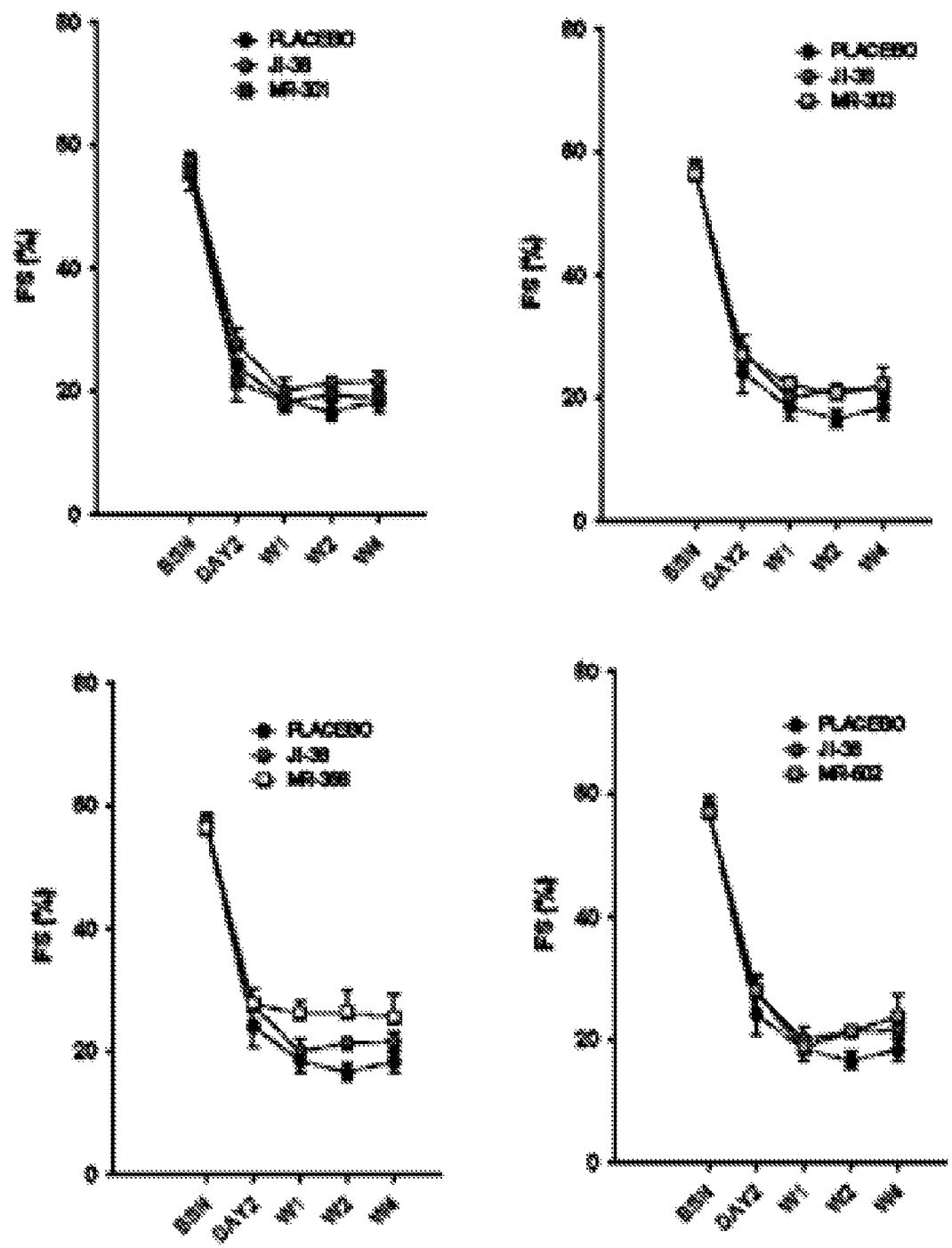
FIG. 15A-D show fraction shortening (FS) measurements in rats treated with various GHRH analogs, according to embodiments.
Figure 15B:
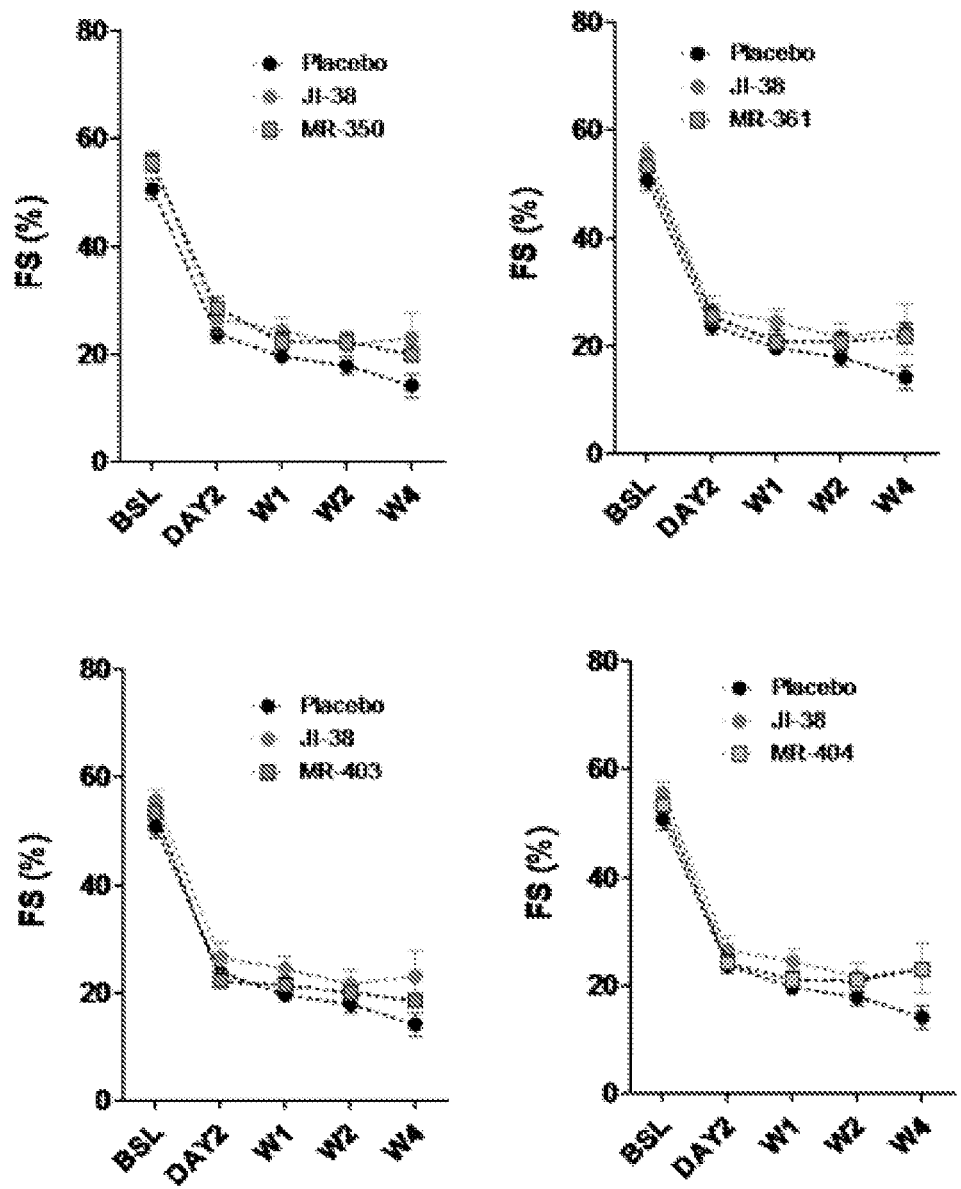
Figure 15C:
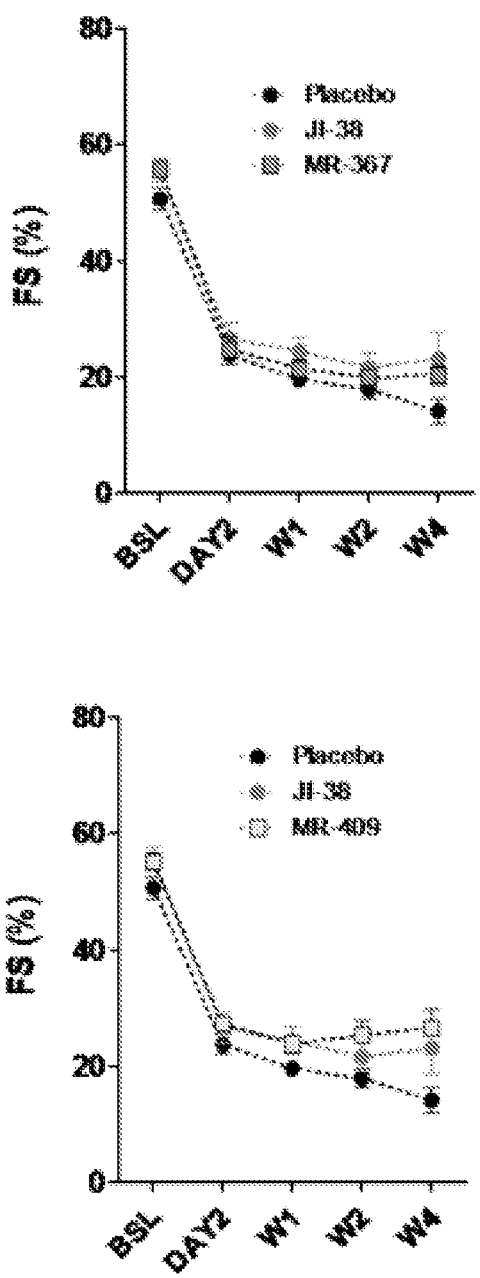
Figure 15D:
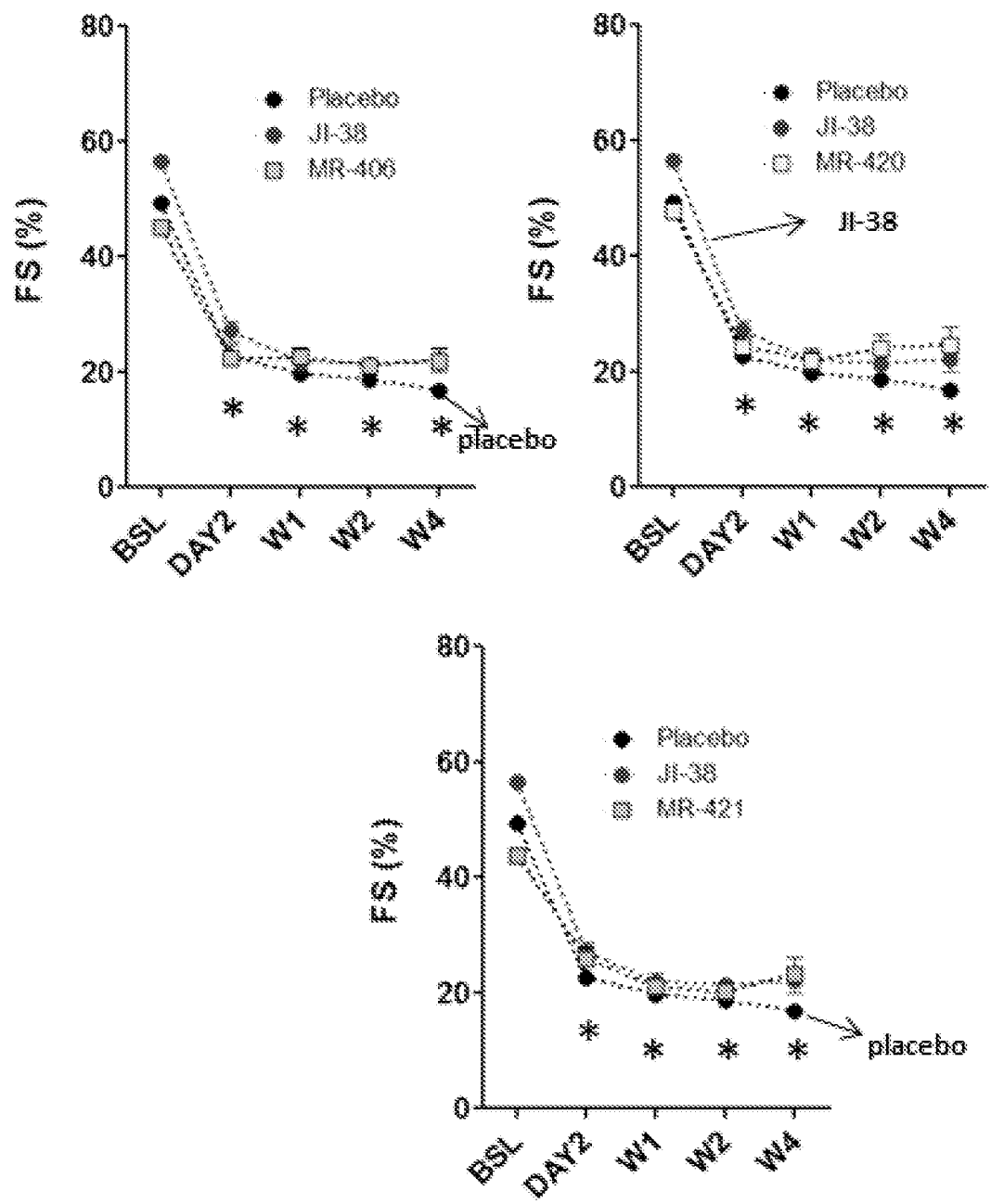
Figure 16:
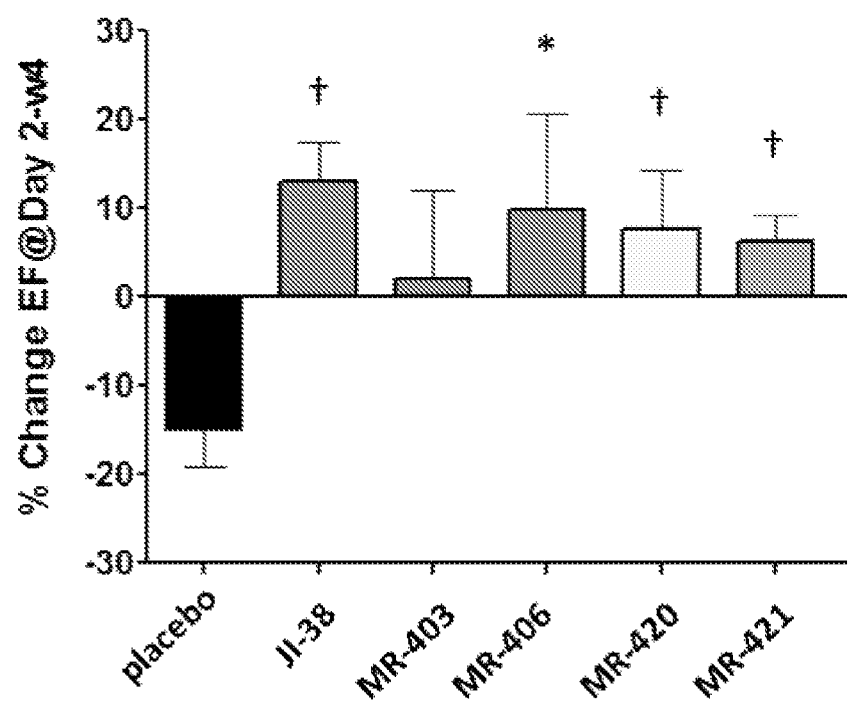
FIG. 16 shows summary of ejection fraction (EF) studies after 4-week treatment with GHRH agonists JI-38, MR-403, MR-406, MR420, and MR-421. Bar graphs show the percentage of change in ejection fraction (EF %) at 4 weeks relative to day 2 post-MI. All values represent mean±SEM (Unpaired t test: *p<0.05, †p<0.01 vs. placebo, n=7-18).
Figure 17A:
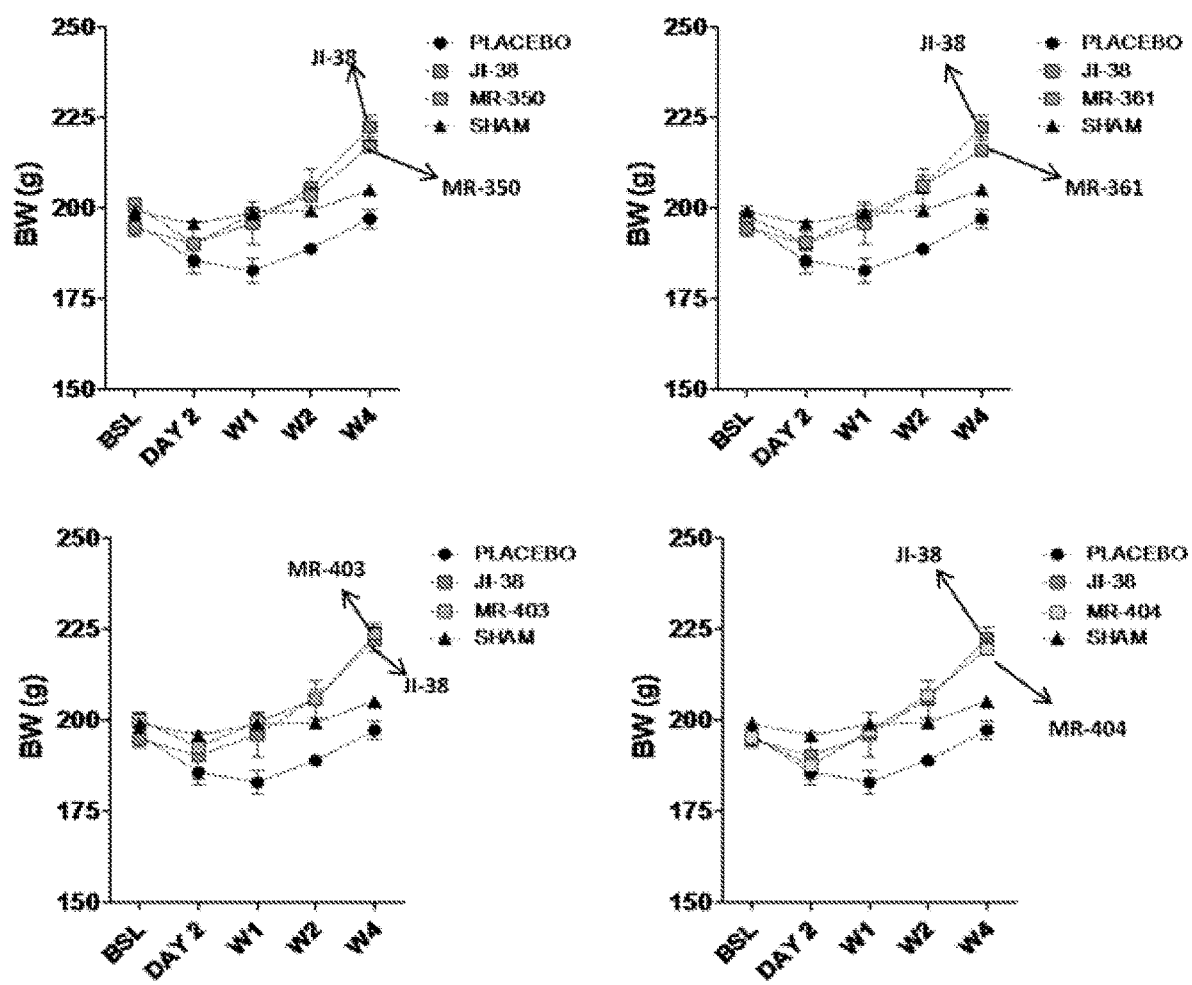
FIG. 17A-B illustrate body weight (BW) measurements of rats treated with various GHRH analogs, according to embodiments. GHRH analogs increased body weight around week 4.
Figure 17B:
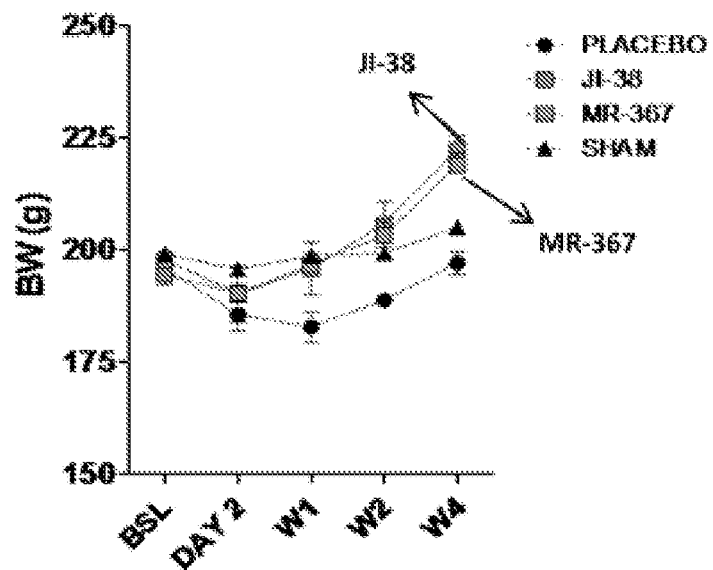
Figure 17B:
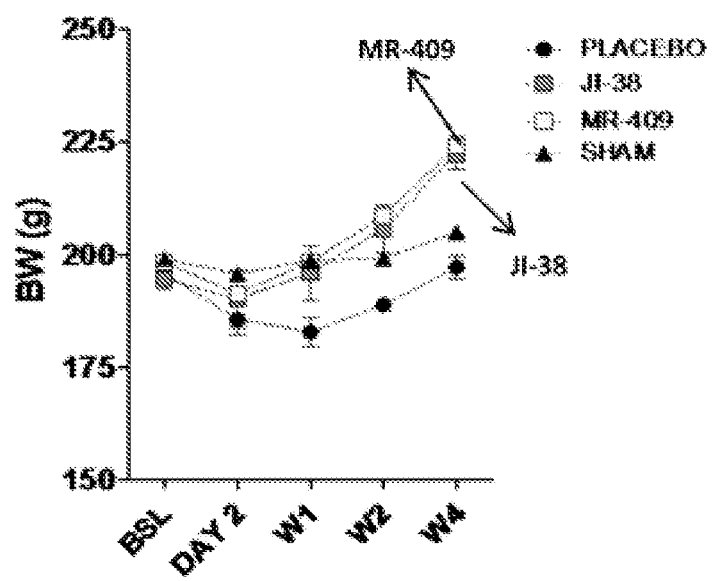
Figure 18:
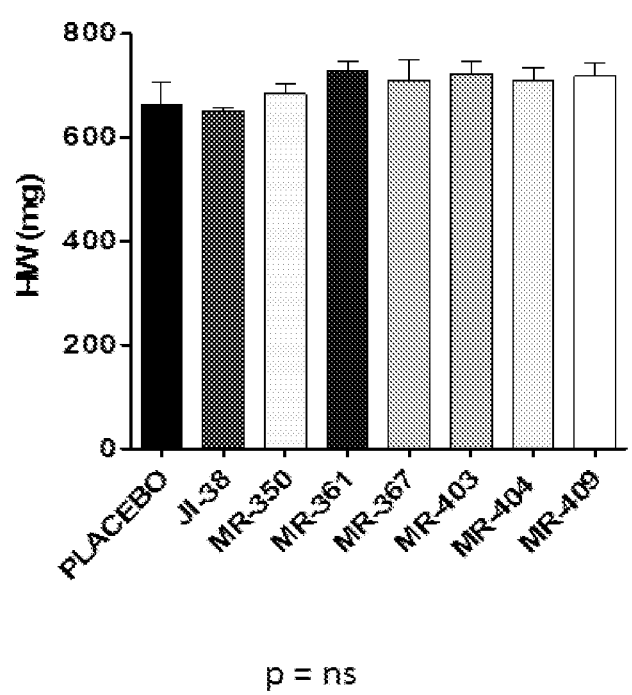
FIG. 18 illustrates heart weight (HW) measurements of rats treated with various GHRH analogs, according to an embodiment.
Figure 19:
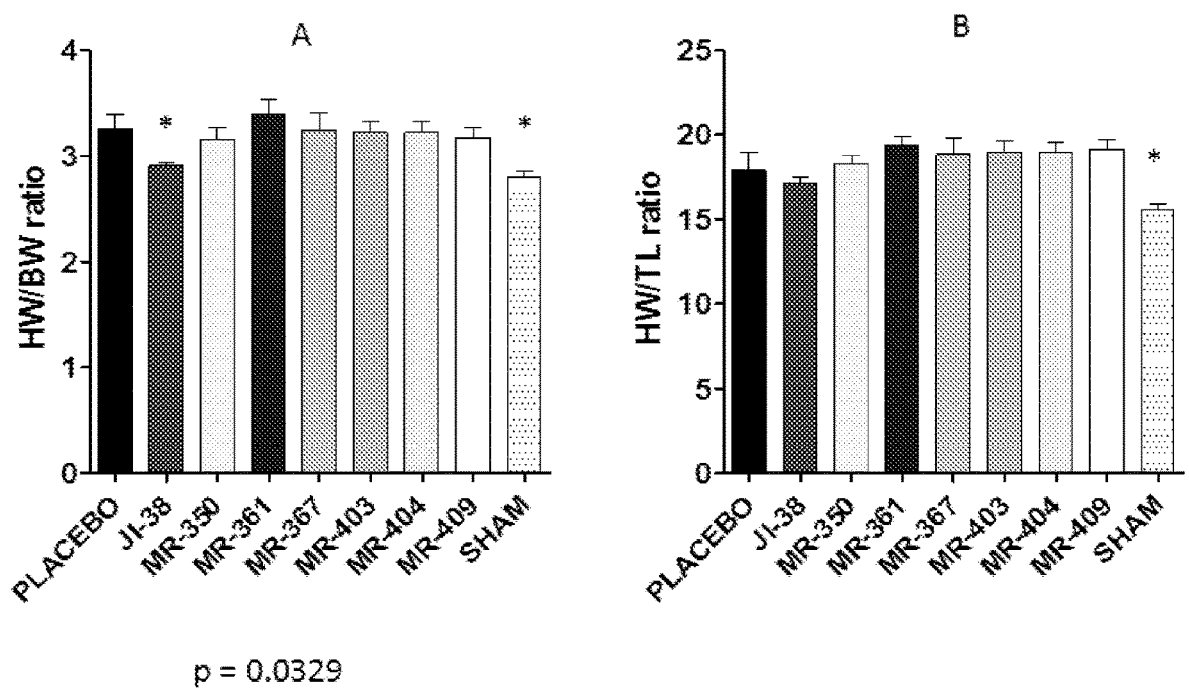
FIG. 19 illustrates ratio of heart weight/body weight (HW/BW) (Panel A) and ratio of heart weight/tibia length (HW/TL) (Panel B) in rats treated with various GHRH analogs, according to an embodiment.
Figure 20:
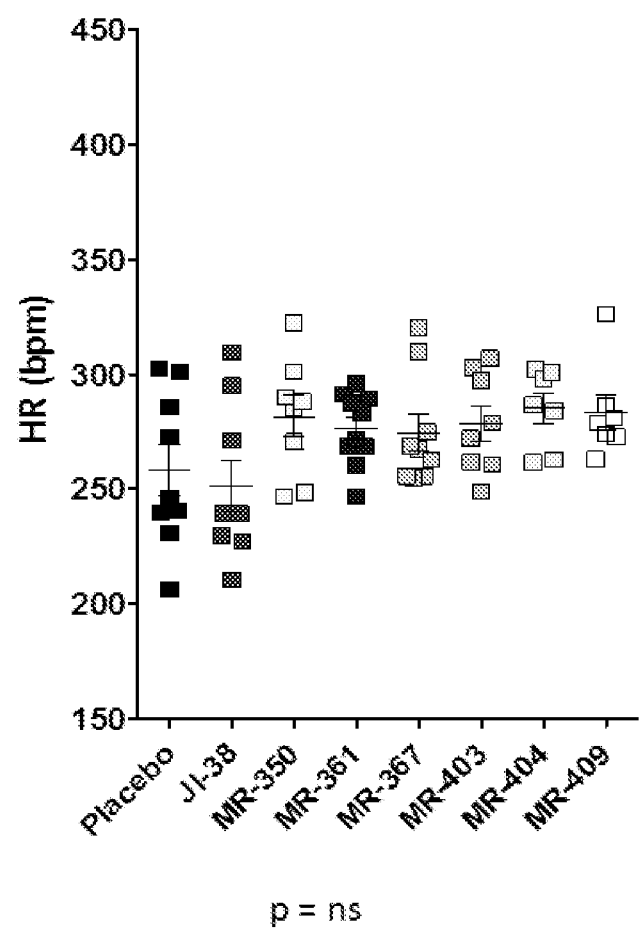
FIG. 20 illustrates heart rate (HR) measurements in rats treated with various GHRH analogs, according to an embodiment.
Figure 21:
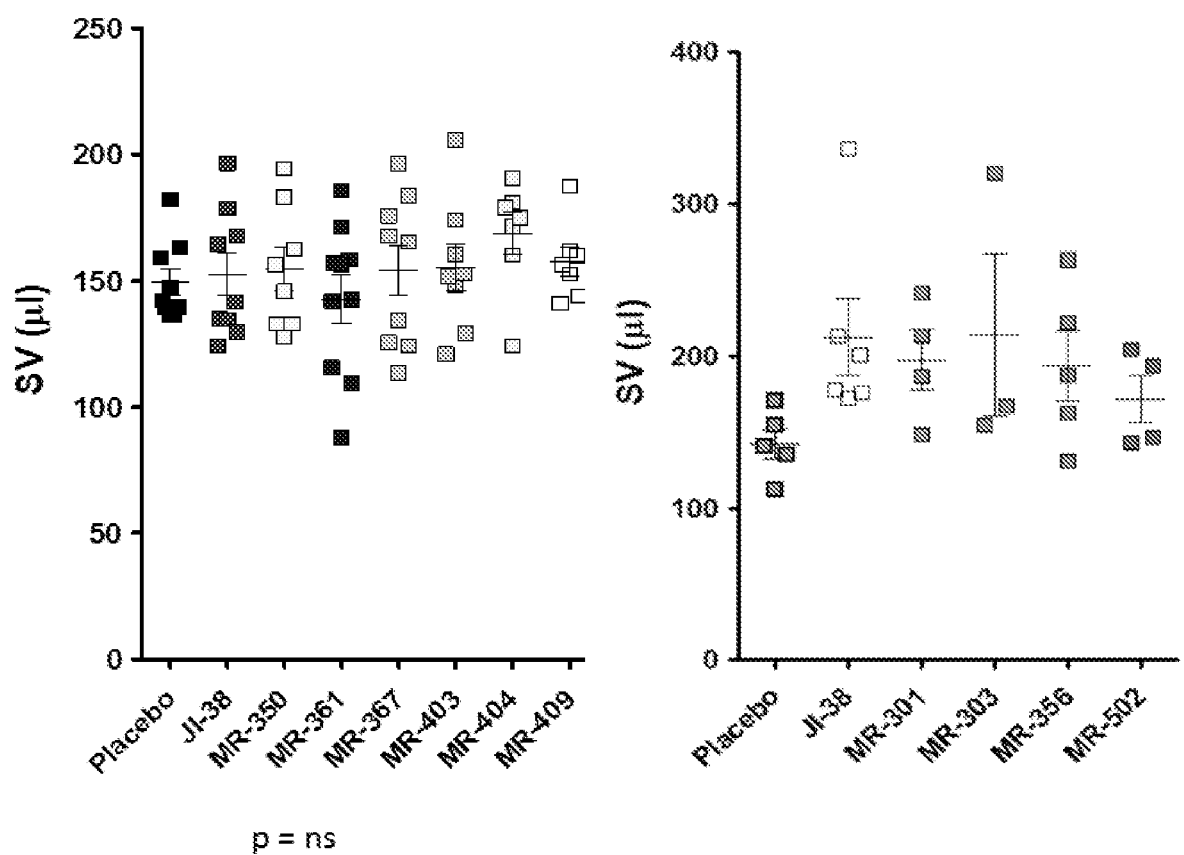
FIG. 21 illustrates stroke volume (SV) measurements in rats treated with various GHRH analogs, according to an embodiment.
Figure 22:
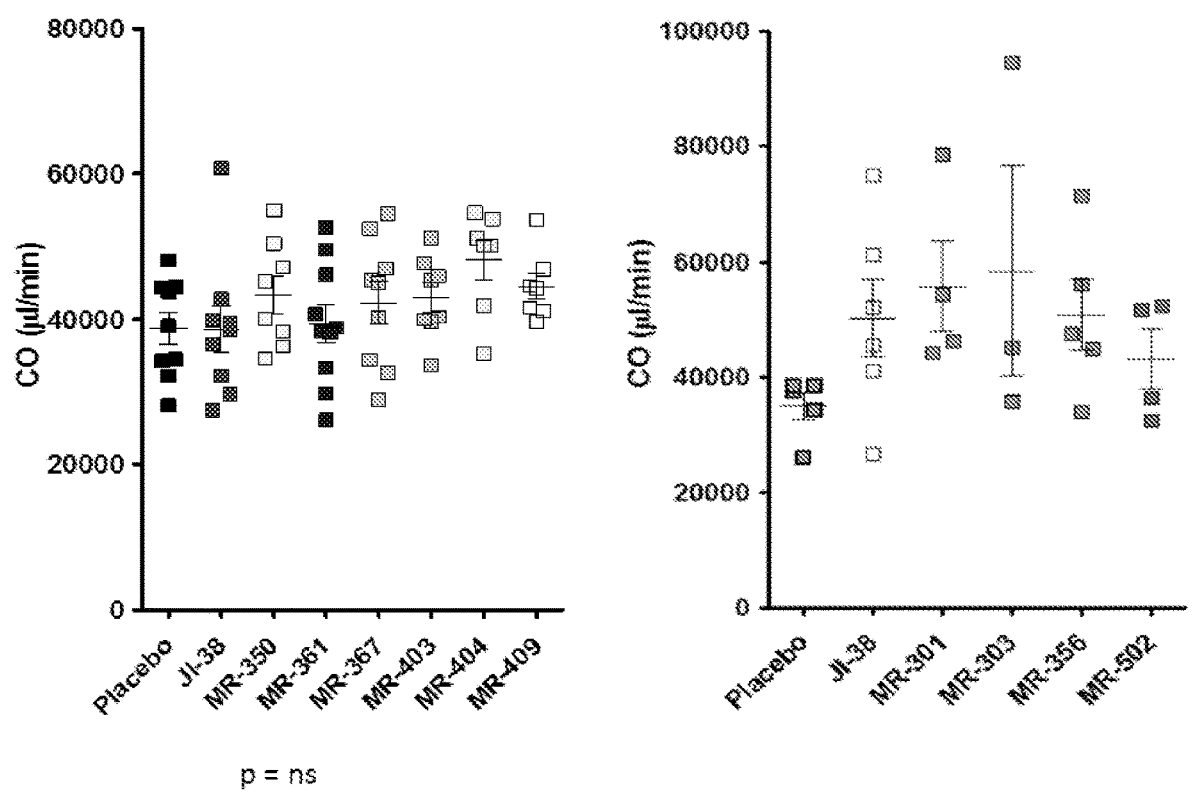
FIG. 22 illustrates cardiac output (CO) measurements in rats treated with various GHRH analogs, according to an embodiment.
Figure 23:
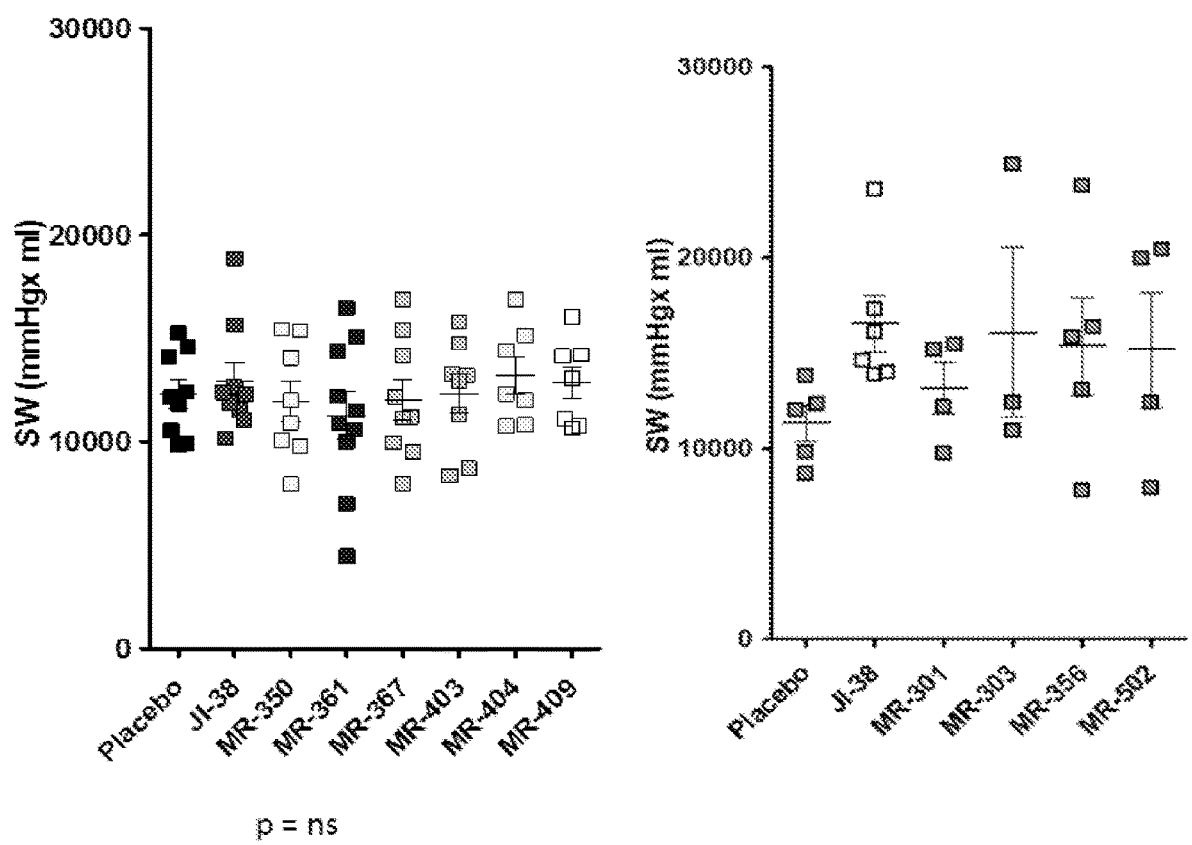
FIG. 23 illustrates stroke work (SW) measurements in rats treated with various GHRH analogs, according to an embodiment.
Figure 24:
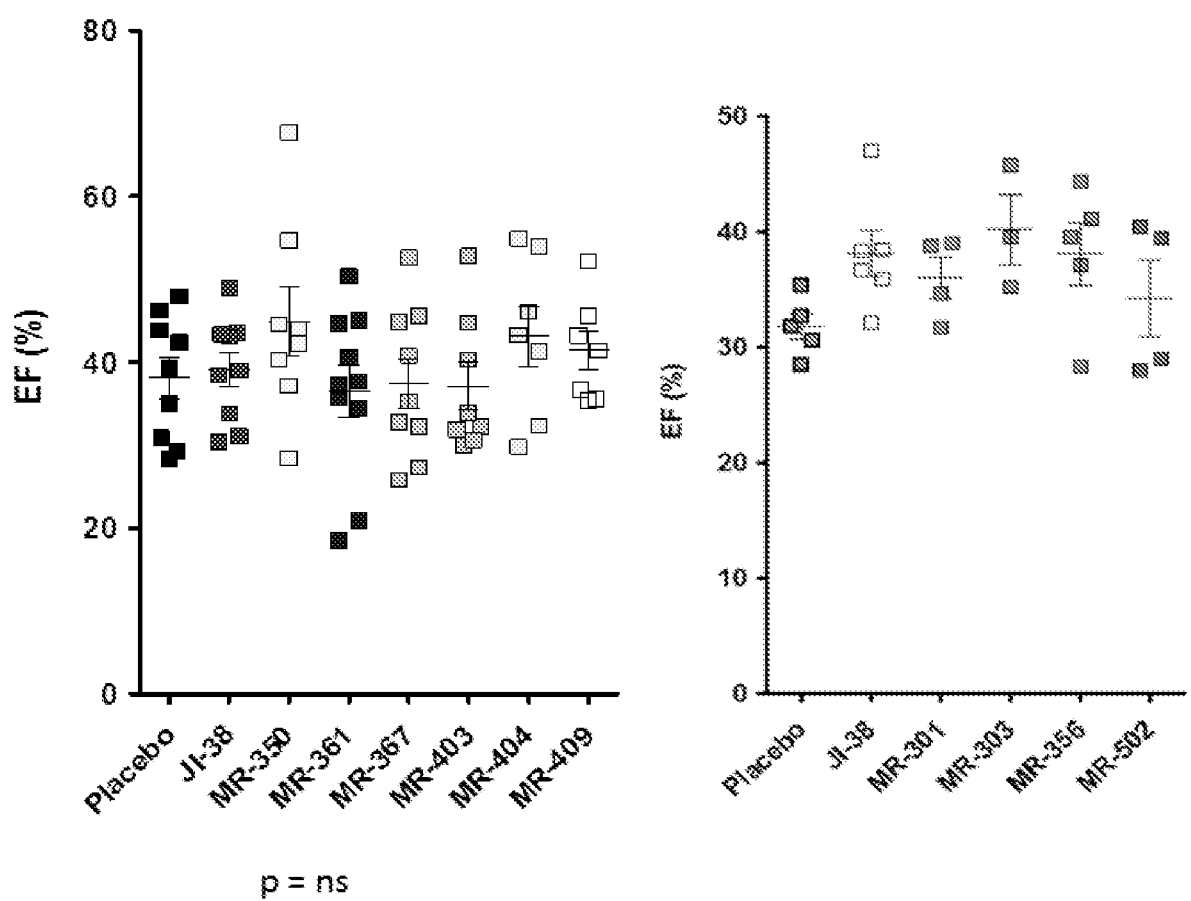
FIG. 24 illustrates ejection fraction (EF) measurements in rats treated with various GHRH analogs, according to an embodiment.
Figure 25:
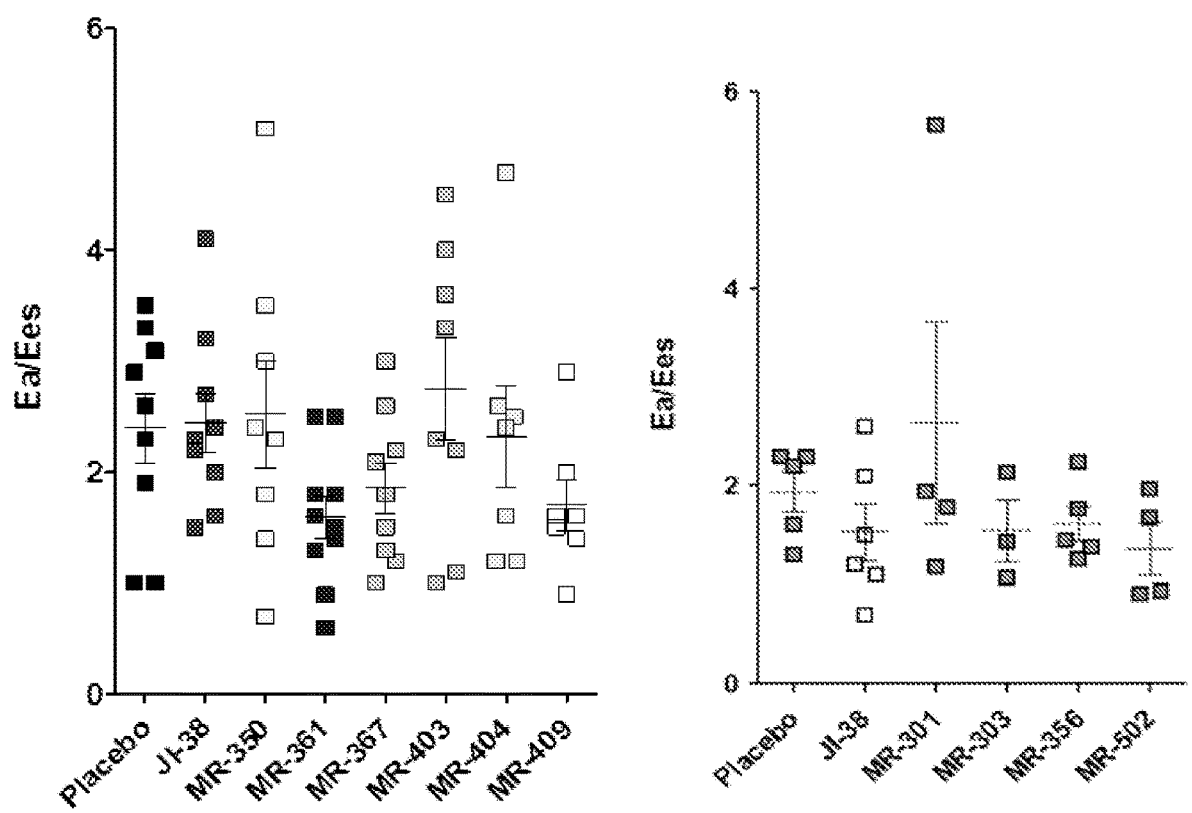
FIG. 25 illustrates ratio of arterial elastance to end-systolic elastance (Ea/Ees) in rats treated with various GHRH analogs, according to an embodiment.
Figure 26:
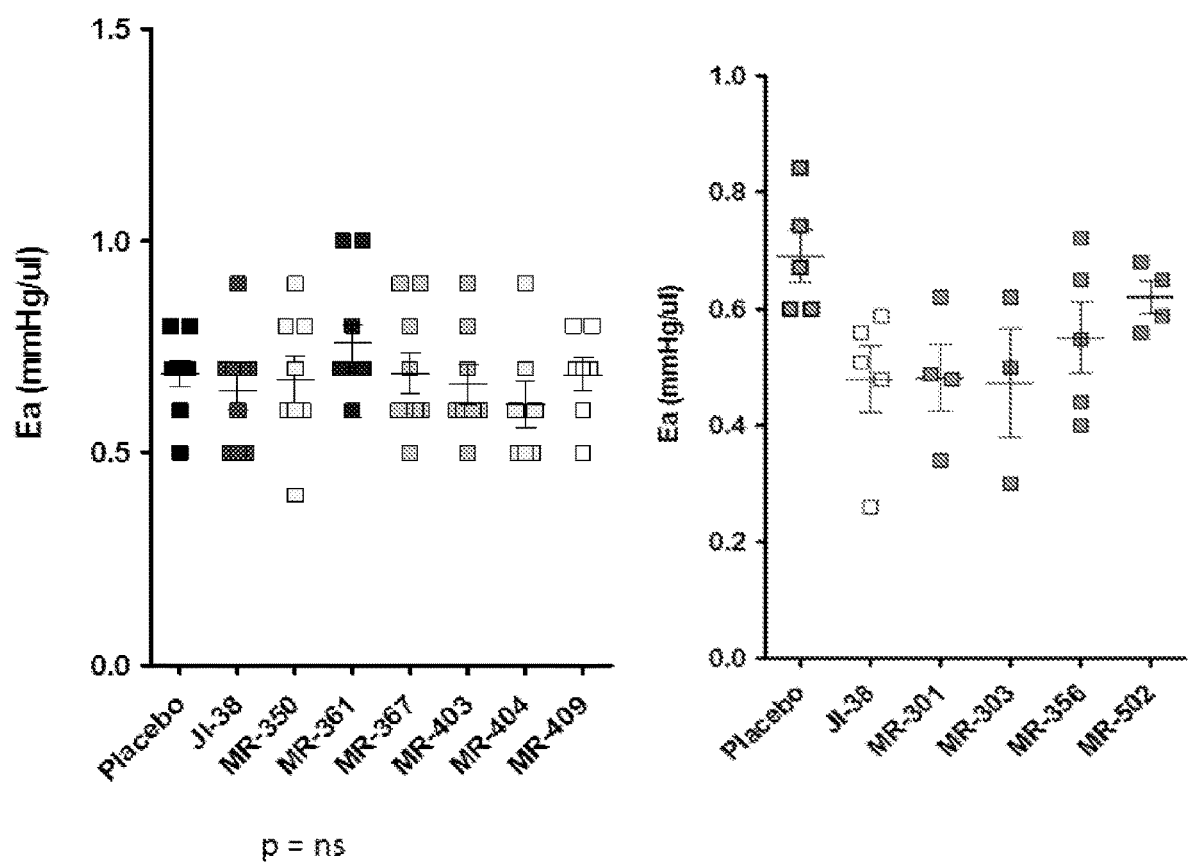
FIG. 26 illustrates arterial elastance (Ea) measurements in rats treated with various GHRH analogs, according to an embodiment.
Figure 27:
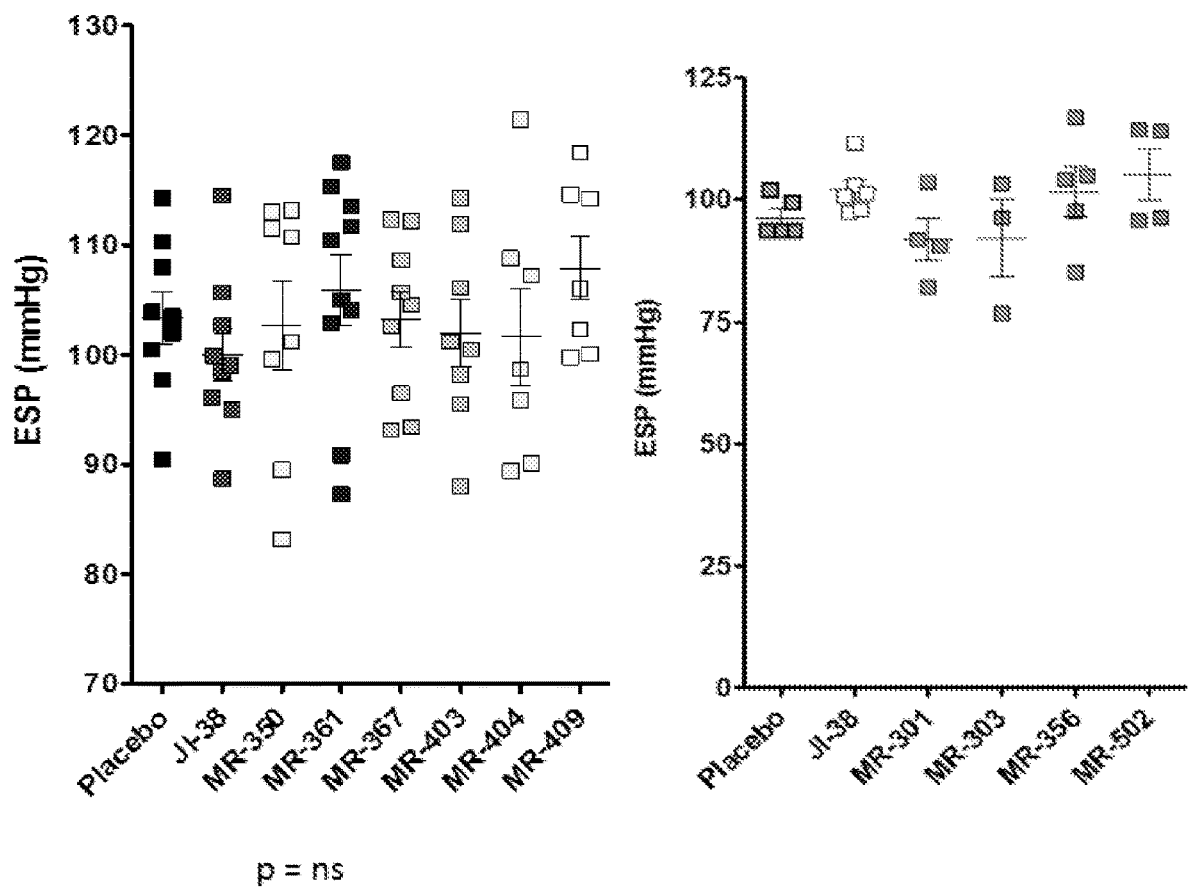
FIG. 27 illustrates end-systolic pressure (ESP) measurements in rats treated with various GHRH analogs, according to an embodiment.
Figure 28:
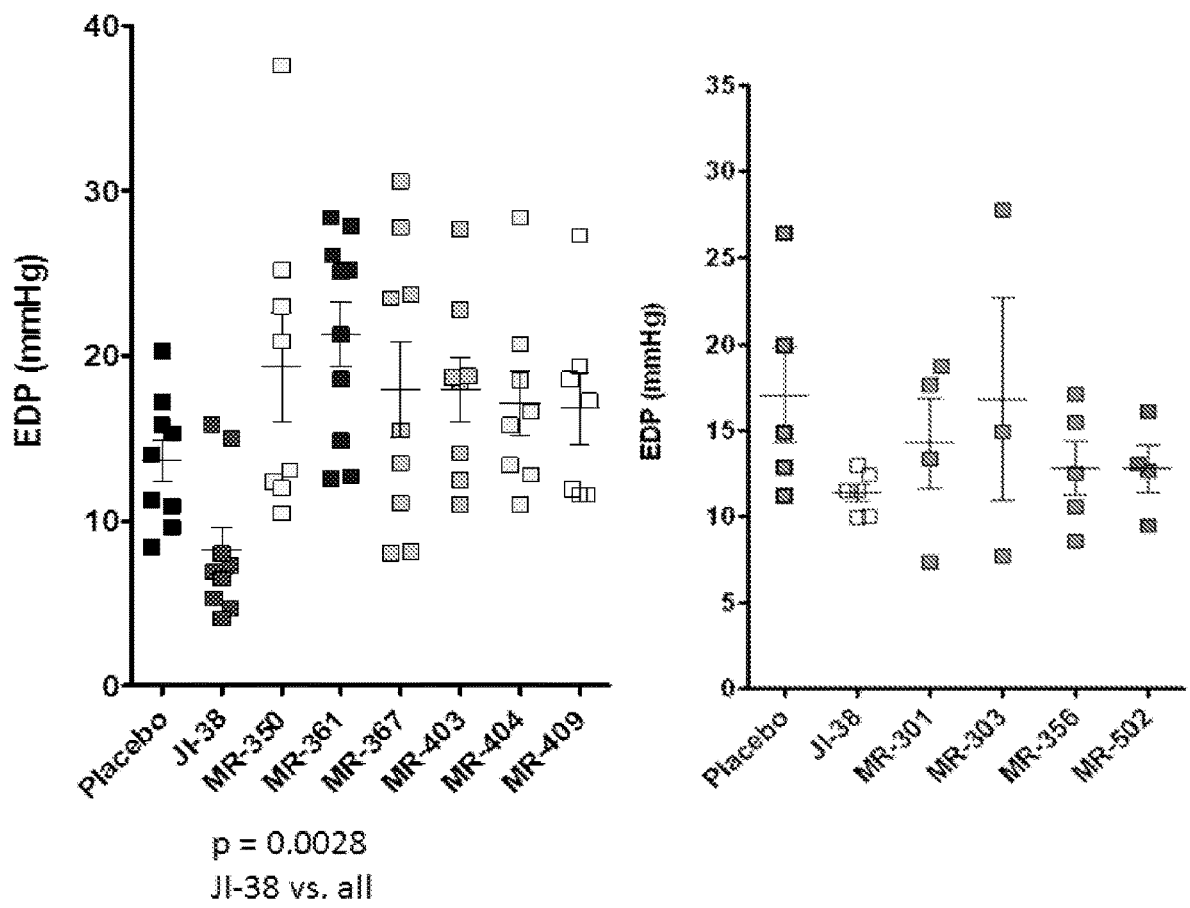
FIG. 28 illustrates end-diastolic pressure (EDP) measurements in rats treated with various GHRH analogs, according to an embodiment.
Figure 29:
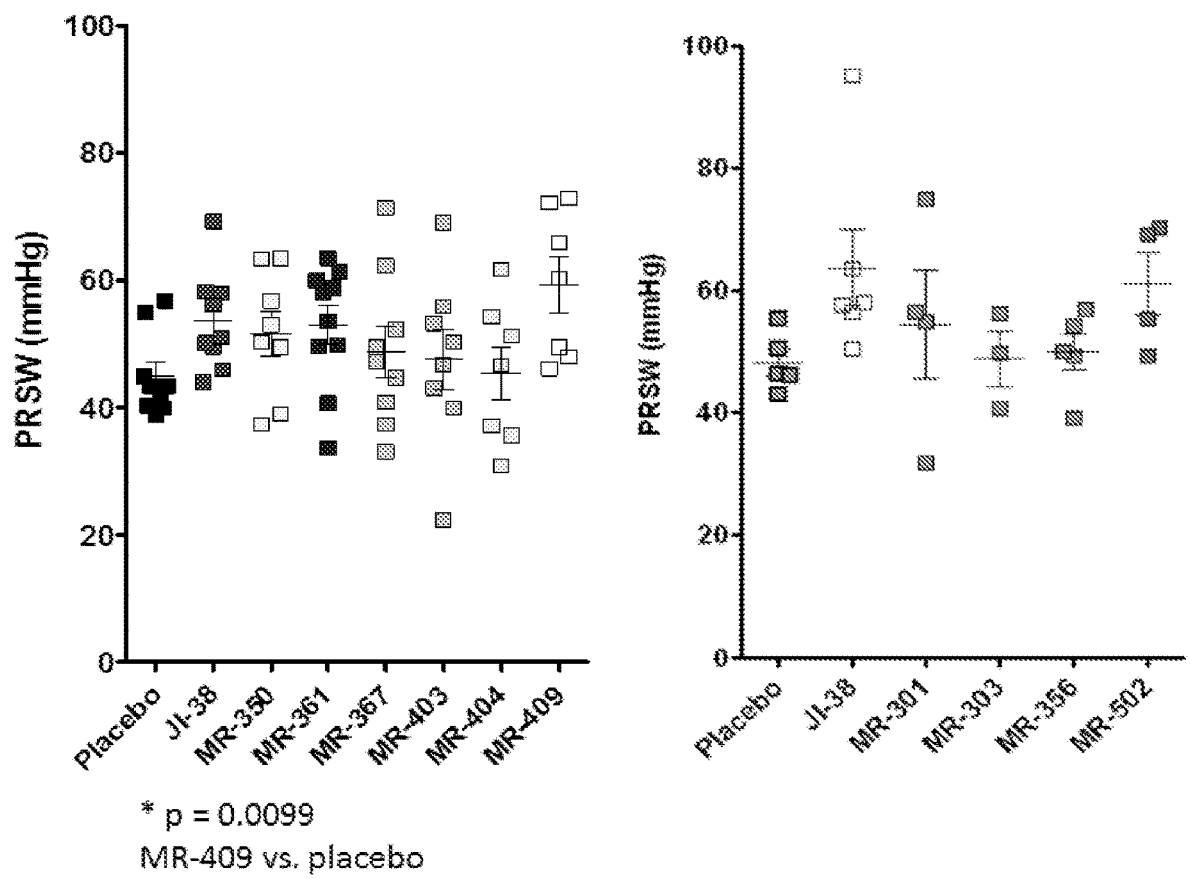
FIG. 29 illustrates preload recruitable stroke work (PRSW) measurements in rats treated with various GHRH analogs, according to an embodiment.
Figure 30:
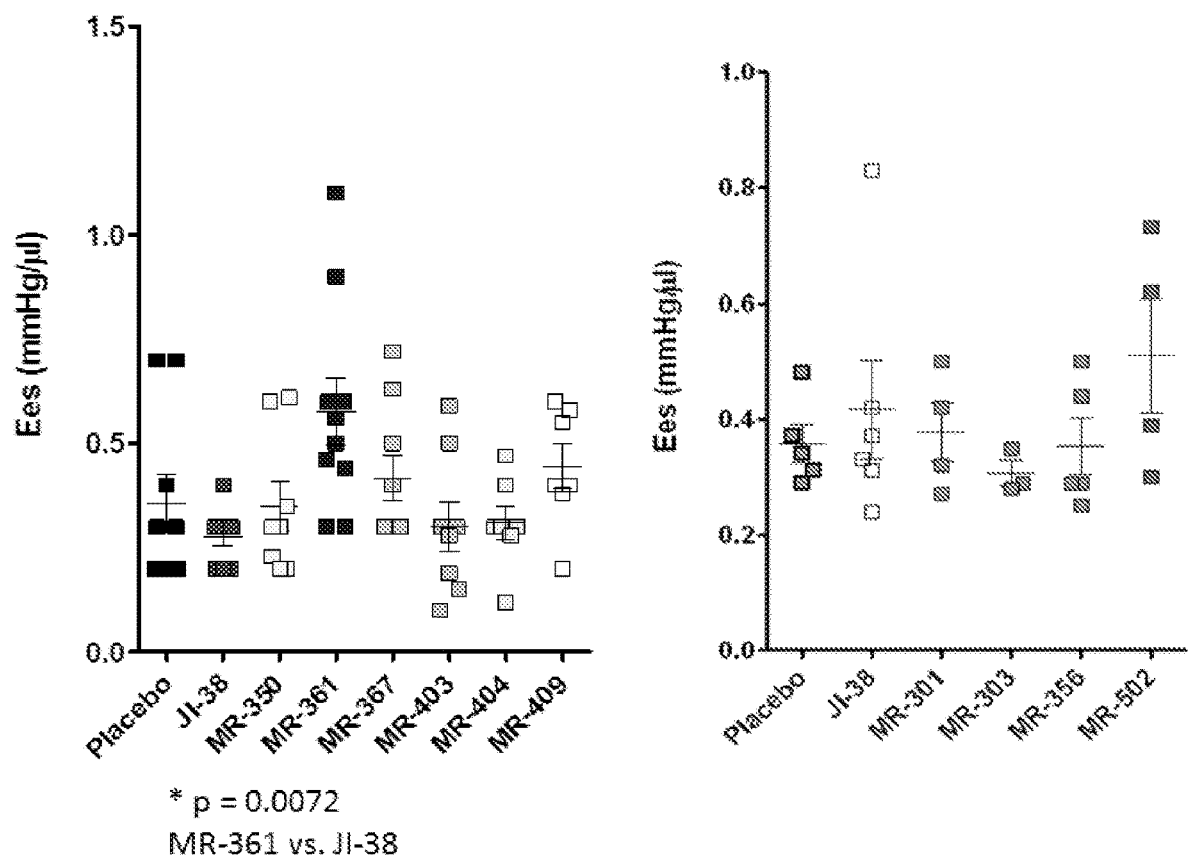
FIG. 30 illustrates end-systolic elastance (Ees) measurements in rats treated with various GHRH analogs, according to an embodiment.
Figure 31:
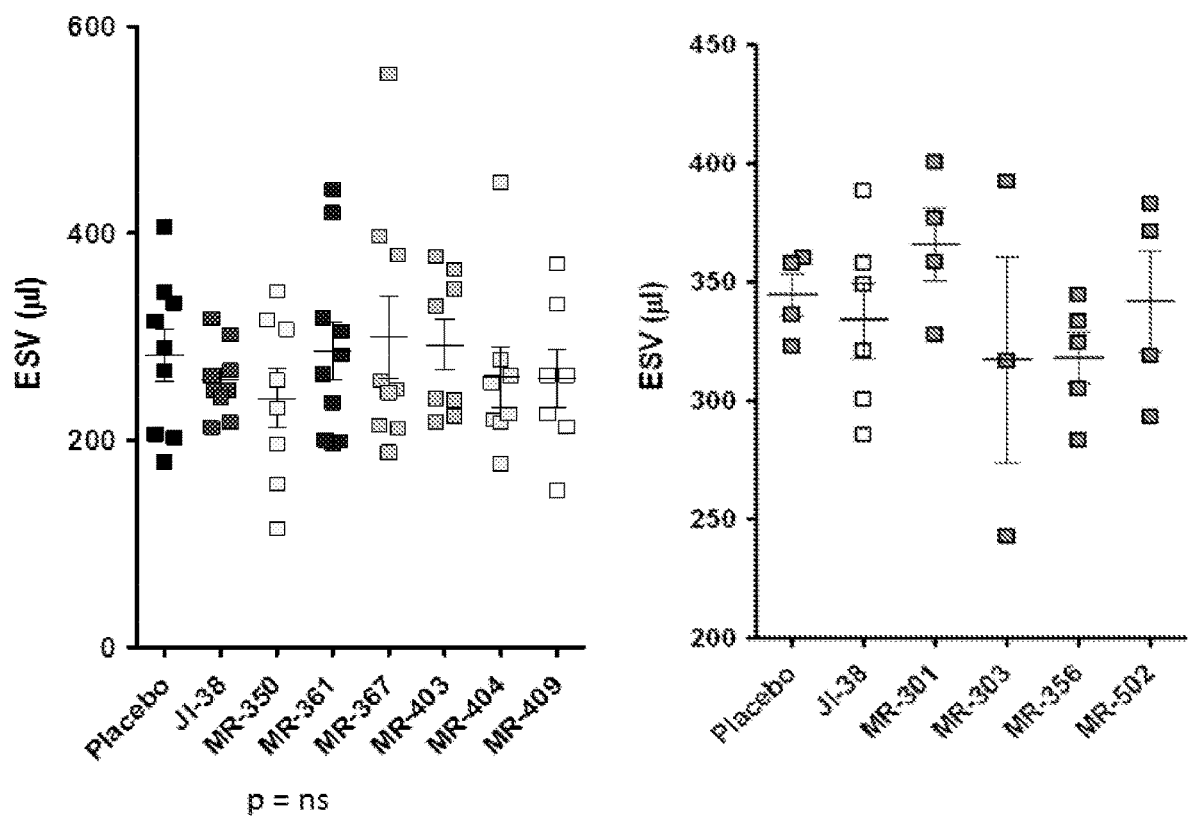
FIG. 31 illustrates end-systolic volume (ESV) measurements in rats treated with various GHRH analogs, according to an embodiment.
Figure 32:
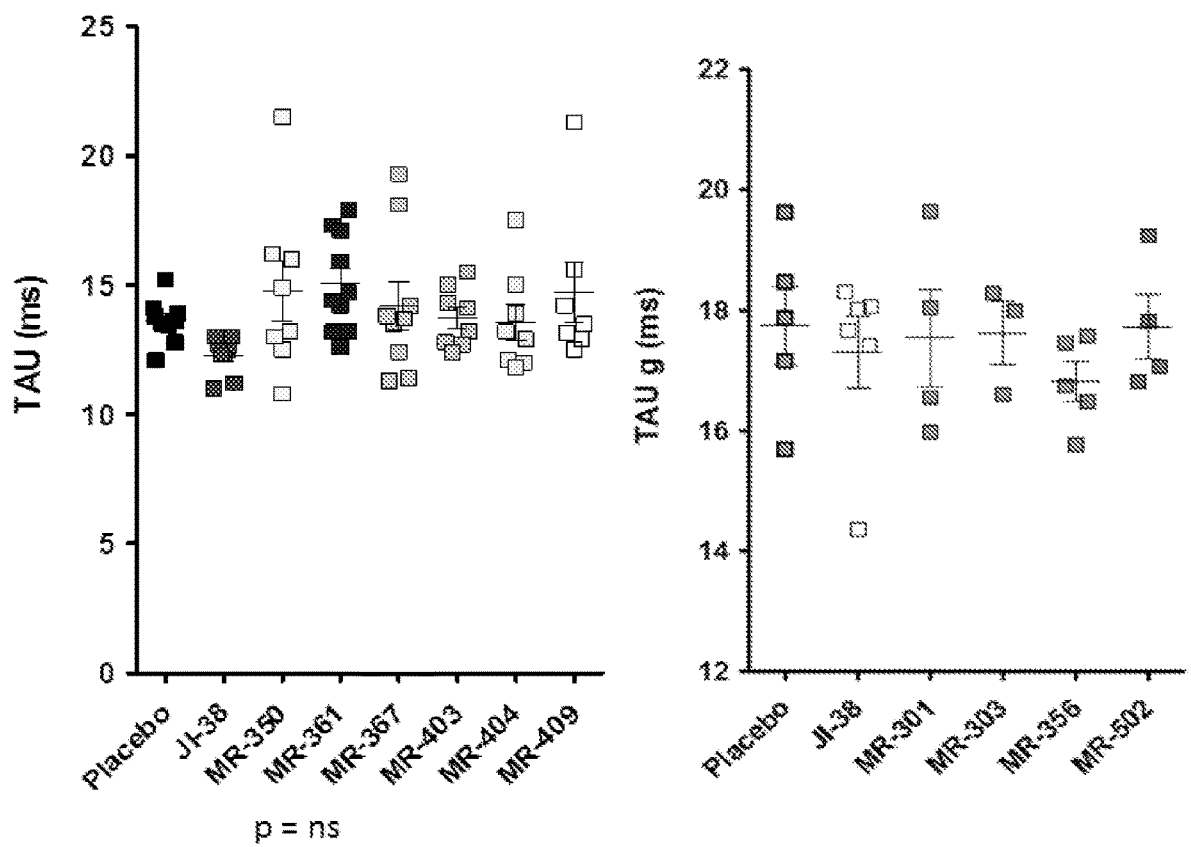
FIG. 32 illustrates relaxation time constant (TAU) measurements, as calculated by Weiss method, in rats treated with various GHRH analogs according to an embodiment.
Figure 33:
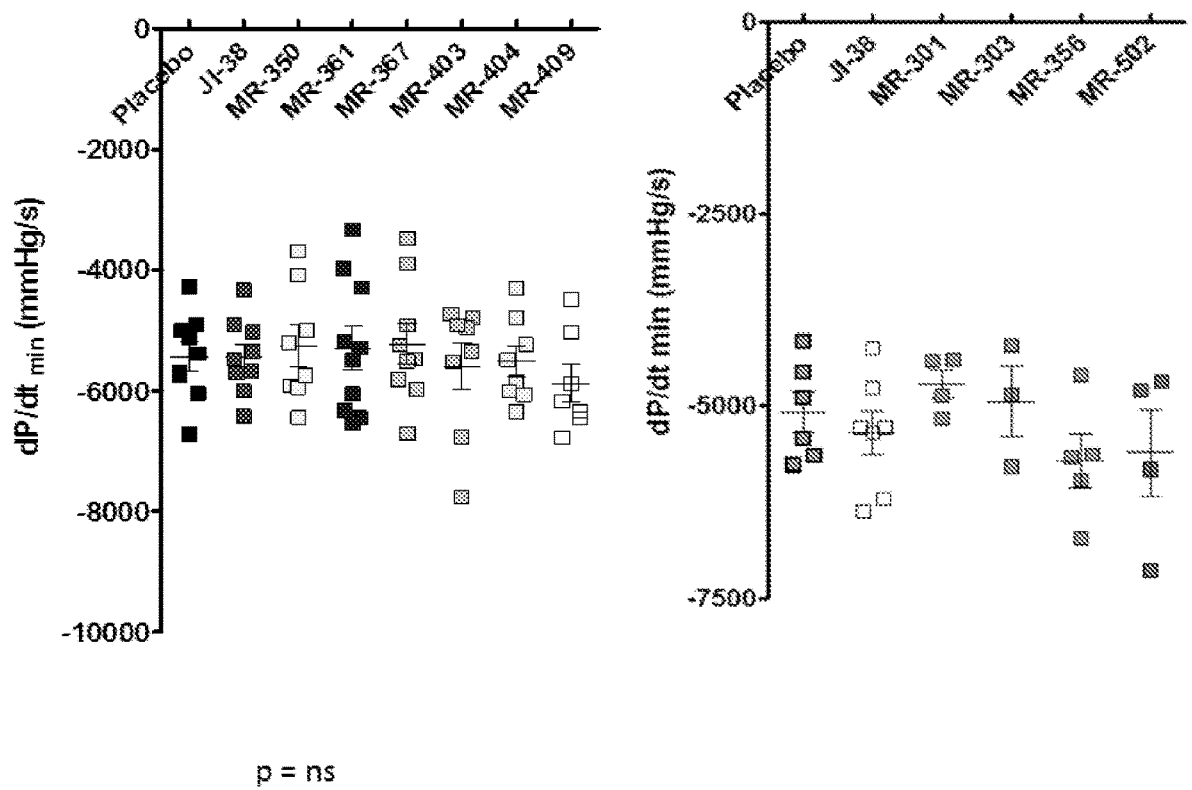
FIG. 33 illustrates measurements of peak rate of the pressure rise (dP/dt) in rats treated with various GHRH analogs according to an embodiment.
Figure 34:
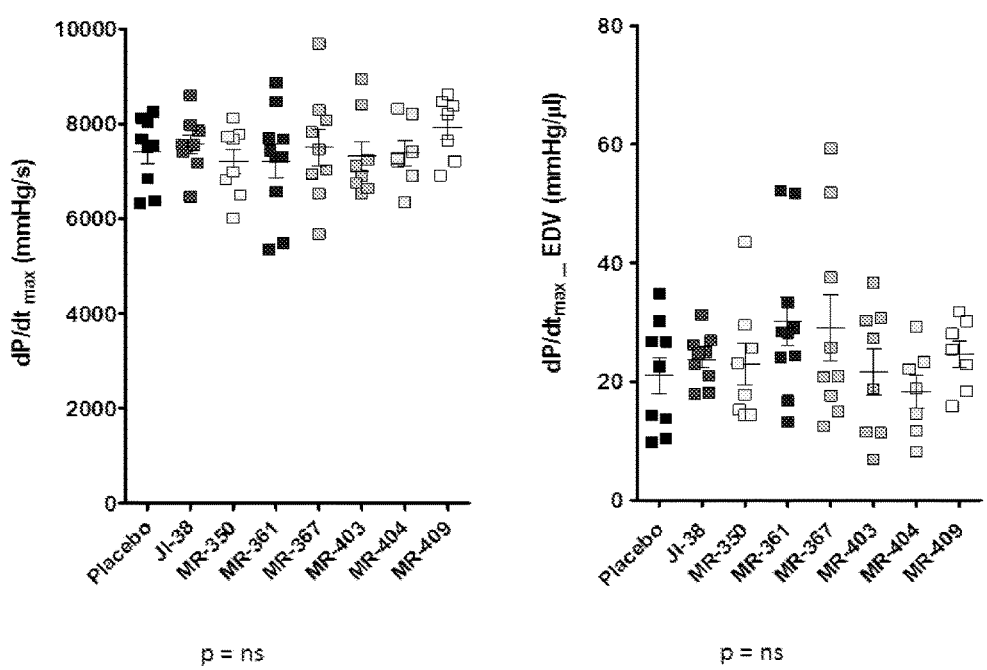
FIG. 34 illustrates contractile measurements in rats treated with various GHRH analogs according to an embodiment.

At baseline and after MI, ejection fractions (EF) were similar in all groups. To facilitate comparisons, the percentage of change was calculated in EF at 4 weeks relative to day 2 post-MI in each group. MI control (placebo group) had a negative treatment effect, as EF decreased over time; in contrast, treatment with the new agonists of GHRH preserved or improved EF (FIG. 9). In addition, the echocardiographic measurements at day 2 post-MI revealed that EF tended to be slightly better preserved in JI-38, MR-356 and MR-361 than all other groups.

Figure 8:
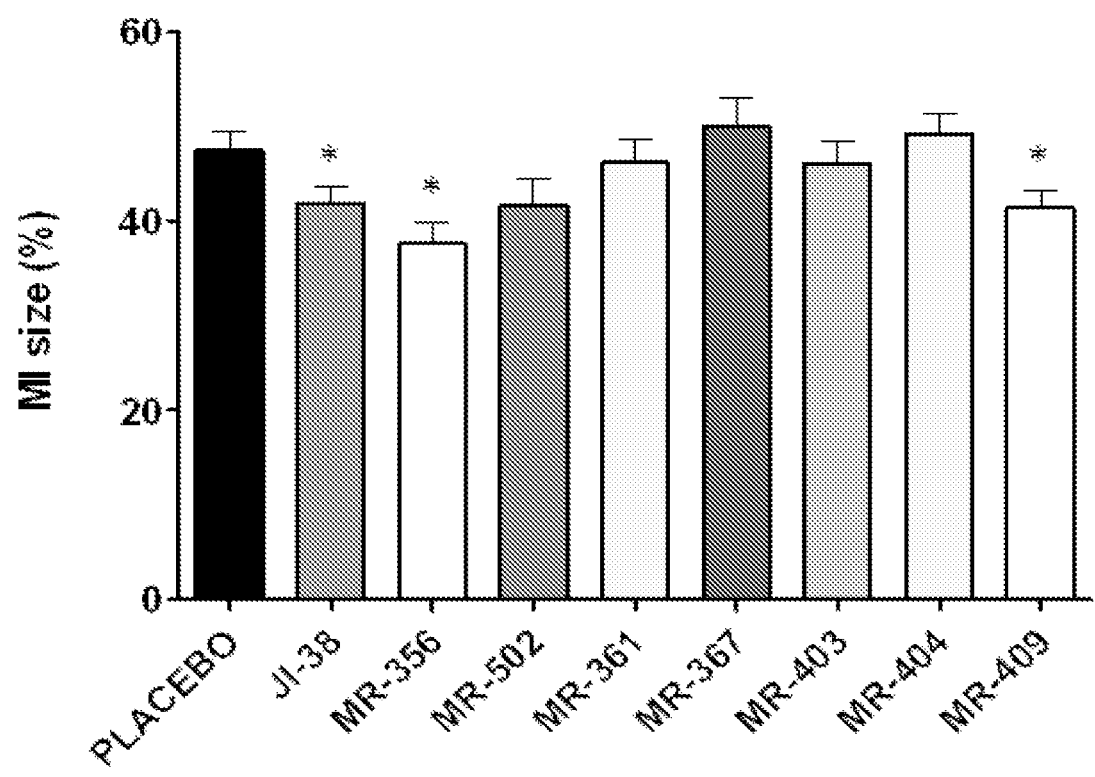
FIG. 8 depicts the impact of GHRH agonists on myocardial infarct burden (MI %). Bar graphs show percentage of infarct size. MI % was significantly attenuated in the groups treated with JI-38, MR-356 and MR-409 (*p<0.05 vs. placebo).

The cardioprotective effects of JI-38, MR-356 and MR-409 were confirmed by substantial reductions in the infarct size when compared to the placebo group (FIG. 8).

TABLE 12

Effects of subcutaneous administration of hGHRH(1-29)NH$_2$ analogs on GH release in male rats

| Peptide | Dose (µg/kg) | Serum GH level at selected time after injection (ng/ml) | | | Relative potency compared to GHRH(1-29) | | compared to JI-38 | |
|---|---|---|---|---|---|---|---|---|
| | | 0 min | 15 min | 30 min | 15 min | 30 min | 15 min | 30 min |
| GHRH (1-29) | 100 | 34.5 ± 10.2 | 140.9 ± 24.2 | 65.1 ± 16.5 | 1.00 | 1.00 | | |
| | 200 | 74.6 ± 14.1 | 240.0 ± 27.2 | 96.2 ± 3.4 | | | | |
| JI-38 | 3 | 33.2 ± 2.8 | 230.0 ± 15.1 | 128.7 ± 13.3 | 63.1 | 111.8 | 1.00 | 1.00 |
| MR-326 | 3 | 43.7 ± 6.4 | 309.2 ± 33.5 | 225.9 ± 19.8 | 92.7 | 303.4 | 1.47 | 2.71 |
| MR-327 | 3 | 31.5 ± 3.4 | 258.7 ± 31.1 | 138 ± 27.9 | 73.5 | 126.5 | 1.16 | 1.16 |
| MR-351 | 3 | 30.6 ± 7.2 | 90.8 ± 20.3 | 65.4 ± 10.1 | 18.8 | 33.6 | 0.30 | 0.30 |
| MR-356 | 3 | 25.3 ± 3.9 | 305.4 ± 40.0 | 152.4 ± 21.8 | 91.2 | 150.9 | 1.45 | 1.35 |
| MR-361 | 3 | 46.1 ± 6.3 | 275.9 ± 46.4 | 142.6 ± 18.4 | 80 | 134.1 | 1.27 | 1.20 |
| MR-367 | 3 | 41.1 ± 5.6 | 244.0 ± 25.1 | 141.2 ± 12.3 | 68.1 | 131.7 | 1.08 | 1.18 |
| MR-401 | 3 | 24.6 ± 5.3 | 217.9 ± 37.0 | 204.1 ± 23.7 | 58.8 | 253.4 | 0.93 | 2.27 |
| MR-403 | 3 | 39.4 ± 5.3 | 608.7 ± 35.3* | 281.7 ± 18.6* | 223.8 | 448.9 | 3.55* | 4.02* |
| MR-404 | 3 | 29.5 ± 3.2 | 320.5 ± 32.7 | 151 ± 28.5 | 97.1 | 148.4 | 1.54 | 1.33 |
| MR-405 | 3 | 21.8 ± 5.9 | 227.9 ± 10.5 | 143.3 ± 6.1 | 62.3 | 135.2 | 0.99 | 1.21 |
| MR-406 | 3 | 21.3 ± 4.8 | 492.6 ± 21.8* | 282 ± 17.8* | 170 | 449.7 | 2.69* | 4.02* |
| MR-407 | 3 | 36.7 ± 10.2 | 248.0 ± 40.5 | 135.2 ± 10.8 | 69.6 | 122 | 1.10 | 1.09 |
| MR-408 | 3 | 37.6 ± 15.5 | 213.3 ± 32.0 | 121.2 ± 8.4 | 57.2 | 100.5 | 0.91 | 0.90 |
| MR-409 | 3 | 18.9 ± 3.1 | 427.4 ± 62.4* | 256.7 ± 20.7* | 141.3 | 380.6 | 2.24* | 3.4* |
| MR-410 | 3 | 34.1 ± 1.2 | 334.0 ± 54.0 | 250.4 ± 28.6* | 102.5 | 363.2 | 1.58 | 3.25* |
| MR-420 | 3 | 35.5 ± 7.6 | 256.2 ± 46.0 | 126.1 ± 15.8 | 72.6 | 107.8 | 1.15 | 0.96 |
| MR-421 | 3 | 44.0 ± 8.9 | 252.4 ± 33.3 | 137.3 ± 17.5 | 71.2 | 125.4 | 1.13 | 1.12 |
| MR-502 | 3 | 61.7 ± 8.1 | 266.7 ± 21 | 153.2 ± 33.3 | 76.5 | 152.3 | 1.21 | 1.36 |
| MR-504 | 3 | 25.4 ± 4.1 | 200.0 ± 10.7 | 130.0 ± 19.1 | 52.6 | 113.8 | 0.83 | 1.02 |
| MR-702 | 3 | 43.7 ± 5 | 103.7 ± 23.1 | 85 ± 27.8 | 22.4 | 53.5 | 0.35 | 0.48 |

Data are shown as mean ± SEM;
*p < 0.05 vs JI-38 (ANOVA followed by Tukey's test)

TABLE 13

Effects of intravenous administration of GHRH analogs on GH release

| Injection | Dose (µg/kg) | Serum GH level at selected time after injection (ng/ml) | | | Relative potency | |
|---|---|---|---|---|---|---|
| | | 0 min | 5 min | 15 min | 5 min | 15 min |
| JI-38 | 1 | 48.0 ± 10.4 | 538 ± 58.3 | 198 ± 18.1 | 1 | 1 |
| GHRH(1-29) | 1 | 50.1 ± 6.4 | 441 ± 76.0 | 105 ± 23.7* | 0.82 | 0.53* |
| MR-356 | 1 | 37.8 ± 5.7 | 632 ± 110 | 250 ± 58.1 | 1.17 | 1.26 |
| MR-403 | 1 | 47.7 ± 4.1 | 642 ± 29.7 | 268 ± 21.1 | 1.19 | 1.35 |
| MR-502 | 1 | 59.9 ± 15.9 | 1253 ± 185* | 575 ± 20.9* | 2.05* | 2.90* |
| MR-504 | 1 | 25.7 ± 6.3 | 832 ± 214 | 297 ± 45.6 | 1.55 | 1.50 |
| MR-702 | 1 | 47.7 ± 3.4 | 578 ± 87.7 | 273 ± 40.8 | 1.07 | 1.38 |

Data are shown as mean ± SEM;
*p < 0.05 versus JI-38

TABLE 14

IC$_{50}$ values and relative binding affinities of our new GHRH(1-29) agonists to the membrane receptors or human pituitary cells

| GHRH agonists | IC$_{50}$ (nM) | Relative affinity[a] (Binding potency) | |
|---|---|---|---|
| | | compared to hGHRH(1-29) | compared to JI-38 |
| hGHRH(1-29) | 7.65 | 1.00 | |
| JI-38 | 2.74 | 2.79 | 1.00 |
| MR-326 | 0.98 | 7.81 | 2.80 |
| MR-327 | 2.04 | 3.75 | 1.34 |
| MR-351 | 3.87 | 1.98 | 0.71 |
| MR-356 | 1.02 | 7.50 | 2.69 |
| MR-361 | 1.19 | 6.42 | 2.30 |
| MR-367 | 1.09 | 7.01 | 2.51 |
| MR-401 | 2.60 | 2.94 | 1.05 |
| MR-403 | 0.74 | 10.30 | 3.69 |
| MR-404 | 1.12 | 6.83 | 2.45 |
| MR-405 | 2.51 | 3.04 | 1.09 |
| MR-406 | 0.93 | 8.22 | 2.95 |
| MR-407 | 5.01 | 1.52 | 0.54 |
| MR-408 | 6.32 | 1.21 | 0.53 |
| MR-409 | 1.01 | 7.57 | 2.71 |
| MR-410 | 1.28 | 5.98 | 2.14 |
| MR-420 | 2.70 | 2.83 | 1.01 |

TABLE 14-continued

IC$_{50}$ values and relative binding affinities of our new GHRH(1-29) agonists to the membrane receptors or human pituitary cells

| GHRH agonists | IC$_{50}$ (nM) | Relative affinity$^a$ (Binding potency) | |
|---|---|---|---|
| | | compared to hGHRH(1-29) | compared to JI-38 |
| MR-421 | 3.05 | 2.50 | 0.90 |
| MR-502 | 2.16 | 3.54 | 1.27 |
| MR-504 | 2.85 | 2.68 | 0.96 |
| MR-702 | 3.30 | 2.31 | 0.83 |

$^a$Expressed relative to hGHRH(1-29)NH$_2$ = 1 and JI-38 = 1. Values were calculated from duplicate tubes.

Discussion

Fourteen of the new analogs demonstrated enhanced GH release stimulation in vivo as well as increased hGHRH receptor binding affinities in vitro when compared to agonist JI-38. The structural design of these new agonists was based on previous potent hGHRH analogs of the "JI" series. Therefore, in the synthesis strategy for the new analogs, several key features of JI-34, JI-36 and JI-38 were maintained. These included substitutions of Orn$^{12, 21}$, Gln$^8$, Nle$^{27}$ and Asp$^{28}$, each of which inhibited isomerization or degradation; and a replacement of Gly by Abu at position 15, which appeared to increase affinity for the GHRH receptor. On the basis of their structures, the selected new hGHRH agonists could be classified into three groups (Table 11). Thus, of three analogs, which belonged to the Agm$^{29}$ group, including MR-356 (N-Me-Tyr$^1$-JI-38), MR-361 (NMe-Tyr$^1$, D-Ala$^2$-JI-38) and MR-367 (N-Me-Tyr$^1$, D-Ala$^2$, Asn$^8$-JI-38), showed improved receptor binding affinity when compared to JI-38. In particular, MR-356 displayed a 2.7 fold increase in GHRH receptor binding affinity, and 1.4 times greater potency of GH release at 15 minutes and 30 minutes after subcutaneous administration. This was slightly better than that of MR-361 and MR-367. These findings suggested a correlation between the introduction of the N-Me-Tyr$^1$ residue into the peptide and the consequent enhancement in receptor binding. Dat$^1$ in JI-38 or acetylated N-Me-Tyr, as it in MR-351, showed weaker GH-releasing potency and GH receptor binding affinity than those of N-Me-Tyr$^1$, Agm$^{29}$ agonists. This implied that the methylation on alpha amino group of Tyr and the resulting secondary amino group of N-Me-Tyr appeared to be favorable for receptor binding and GH releasing capability. Interestingly, a replacement of Ala$^2$ in MR-356 by D-Ala$^2$ in MR-361 or D-Ala$^2$, Asn$^8$ in MR-367 resulted in a reduced GH-releasing capability and slightly weakened binding affinity. These results suggested that the structure of Ala$^2$, Gln$^8$ in MR-356 is the more favorable addition to Agm$^{29}$ agonists with regard to the issue of endocrine potency.

Group II featured a replacement of Agm$^{29}$ by Arg$^{29}$-NH—CH$^3$ or Arg$^{29}$-NH—CH$_2$—CH$_3$ at the C-terminal end of the GHRH agonist and was therefore called the Arg$^{29}$-NH—CH$_3$ or Arg$^{29}$-NH—CH$_2$—CH$_3$-GH—RH agonist group. The peptide with Arg$^{29}$-NH—CH$_3$, as in MR-403, was more potent than the peptide with Arg$^{29}$-NH—CH$_2$—CH$_3$, as in MR-420. The most potent compounds of this group were MR-403 (N-Me-Tyr$^1$, DAla$^2$, Arg$^{29}$-NH—CH$_3$-JI-38), MR-406 (N-Me-Tyr$^1$,Arg$^{29}$-NH—CH$_3$-JI-38) and MR-409 (N-Me-Tyr$^1$,DAla$^2$,Asn$^8$,Arg$^{29}$-NH—CH$_3$-JI-3 8) (Table 11). Among these, MR-403 was the most potent and exhibited the highest GH-releasing potency and binding affinity. Compared to JI-38, the receptor binding affinity of MR-403 was enhanced nearly 3.7-fold and GH-releasing activity in vivo also escalated 3.6-4.0-fold. All three peptides of Group II exhibited significantly increased GH-releasing activities and binding affinities. The replacement of Agm$^{29}$ with Arg$^{29}$-NH—CH$_3$ yielded a significant increase of GH-release and receptor binding affinities. MR-406 appeared to be less potent (GH-release) than MR-403 but was more potent than MR-409. Although MR-406 and MR-409 showed slightly lower GH-releasing potency than MR-403 at 15 minutes after s.c. administration, they all exhibited a significantly higher relative potency than JI-38 at 30 minutes. The calculated potencies of MR-403, MR-406 and MR-409 at 30 minutes relative to JI-38 were 4.0, 4.0, and 3.4, respectively, indicating their stability and long half-life in vivo. Since neither N-Me-Tyr at the N-terminal end nor Arg-NH—CH$_3$ at the C-terminus were present in JI-38, their incorporation in place of Dat$^1$ and Agm$^{29}$ of JI-38 suggested that both substitutions contributed to the improvement of endocrine activity. However, the C-terminal Arg$^{29}$-NH—CH$_3$, but not the N-terminal NMe-Tyr, led to increased proteolytic stability. Hence, this structure was responsible for the higher relative s.c. potencies at 30 minutes. Aside from their similarity at the N- or C-terminal ends, the major structural differences between the Arg$^{29}$-NH—CH$_3$ agonists were at positions 2 and 8, where a replacement of Gln$^8$ in MR-403, by Asn$^8$ in MR-409, or a substitution of D-Ala$^2$ in MR-403 with Ala$^2$ in MR-406 slightly decreased the GH-releasing activities and binding affinities. Consequently, the results indicated that D-Ala$^2$, Gln$^8$ in MR-403 was the most favorable form.

The Third Group of agonists that have a C-terminal Apa$^{30}$-NH$_2$ were represented by MR-326 (N-Me-Tyr$^1$, D-Ala$^2$,Arg$^{29}$, Apa$^{30}$-NH$_2$-JI-38), or Gab$^{30}$-NH$_2$ as in MR-502 (D-Ala$^2$, Fpa5$^6$, Asn$^8$, Ser$^{28}$, Arg$^{29}$, Gab$^{30}$-NH$_2$-JI-38). In this group, MR-326 showed the highest potency for stimulating GH release; its relative potency at 15 and 30 minutes after s.c. injections was 1.5-fold and 2.7-fold greater than that of JI-38, respectively. However with intravenous administration, MR-502 had the highest potency for GH release, even higher than that of MR-403. With repeated s.c. tests, MR-502 was only 1.2-1.4 times greater (GH release) than that of JI-38. MR-356 and MR-403 showed consistently higher potencies than MR-502 in s.c. tests. The relative potency of GH-RH (1-29)-NH$_2$ also appeared greater in i.v. tests than in s.c. tests. The greater potency of MR-502 in i.v. tests was possibly related to the substituent Fpa5$^6$, and an elongated C-terminal Gab$^{30}$-NH$_2$. The substitution with D-Abu$^2$ in MR-504, Fpa5$^6$ in MR-404, Ser$^{28}$ in MR-405 or D-Arg$^{29}$ in MR-401 did not increase their potencies.

MR-326 and five Arg$^{29}$-NH—CH$_3$ or Arg$^{29}$-NH—CH$_2$-CH$_3$ agonists MR-401, MR-403, MR-406, MR-409, and MR-410 had significantly higher potencies at 30 minutes than at 15 minutes. Most of these agonists, except for MR-406, contained a D-configuration residue. The D-amino acid residue and the specific C-terminal structure may improve resistance to enzymatic degradation and lead to prolonged endocrine potency.

Example 15

Effect of GHRH agonists on cardiac function after injury.

Myocardial infarction (MI) was induced by permanent ligation of the left coronary artery in female 6-month-old Fisher-344 rats. Following experimental myocardial infarction (MI), rats were randomly assigned to receive either placebo, JI-38, or one of the following new analogs of GHRH: MR-30 l(P-21301), MR-303(P-21303), MR-356(P-

20356), MR-502(25502), MR-350(P-20350), MR-361(P-20361), MR-367(P-20367), MR-403(P-27403), MR-404(P-27404), and MR-409(P-27409) (10 rats per each group). The GHRH peptide agonists were administered starting 2 hours post-surgery, 1 week, 2 week, and 4 week intervals. All treatment was given subcutaneously twice daily. Cardiac performance was assessed by serial echocardiography and hemodynamic analysis derived from pressure-volume loops as described before.

The echocardiographic experiments are shown in FIGS. 10-15 and the results are summarized in Table 15 (results were expressed in comparison to JI-38; downward arrow denotes lower than JI-38; upward arrow denotes greater than JI-38; =denotes same as JI-38; and double arrow denotes greater effect). Overall, the new analogs showed similar or better effects than JI-38 on cardiac structure and function, as assessed by echocardiography.

TABLE 15

|  | MR-301 | MR-303 | MR-356 | MR-502 | MR-350 | MR-361 | MR-367 | MR-403 | MR-404 | MR-409 |
|---|---|---|---|---|---|---|---|---|---|---|
| LVEDD | ↑ | = | ↓↓ | = | ↓ | = | ↑ | ↑ | ↑ | ↓↓ |
| LVESD | ↑ | = | ↓↓ | = | = | = | ↑ | ↑ | = | ↓↓ |
| VD | ↑ | ↑ | = | ↑ | = | = | ↑ | ↑ | ↑ | = |
| VS | ↑ | ↑ | = | ↑ | = | ↑ | ↑ | ↑ | ↑ | = |
| EF | ↓ | ↓ | = | = | = | ↓ | = | = | = | ↑↑ |
| FS | = | = | ↑↑ | = | = | = | = | ↓ | = | ↑↑ |

LVEDD: Left Ventricular End Diastolic Diameter;
LVESD: Left Ventricular End Systolic Diameter;
VD: Ventricular Diastole;
VS: Ventricular Systole;
EF: Ejection Fraction;
FS: Fraction Shortening.

The hemodynamic studies are shown in FIGS. 16-33 and the results are summarized in Table 16 (results were expressed in comparison to JI-38; downward arrow denotes lower than JI-38; upward arrow denotes greater than JI-38; =denotes same as JI-38; and double arrow denotes greater effect). Results showed that many of the GHRH analogs showed improved effects, when compared to JI-38. Strikingly, PRSW, index of contractility, was markedly increased by MR-409. Further, MR-356 and MR-409 showed reduced cardiac dimensions (LVEDD and LVESD), and substantial improvement on cardiac performance (EF and FS) after MI.

TABLE 16

|  | MR-301 | MR-303 | MR-356 | MR-502 | MR-350 | MR-361 | MR-367 | MR-403 | MR-404 | MR-409 |
|---|---|---|---|---|---|---|---|---|---|---|
| SV | = | = | = | ↓ | = | ↓ | = | = | ↑ | = |
| CO | = | = | = | ↓ | ↑ | = | ↑ | ↑ | ↑ | ↑↑ |
| SW | ↓ | = | = | = | ↓ | ↓ | ↓ | = | = | = |
| EF | ↓ | ↑ | = | ↓ | ↑ | = | = | = | ↑ | ↑↑ |
| Ea/Ees | ↑ | = | = | = | = | ↓ | ↓ | ↓ | = | ↓ |
| Ea | = | = | ↑ | ↑ | = | ↑ | = | = | = | = |
| ESP | ↓ | ↓ | = | = | ↑ | ↑ | ↑ | = | = | ↑ |
| EDP | ↑ | ↑ | = | = | ↑ | ↑ | ↑ | ↑ | ↑ | ↑ |
| ESV | ↑ | = | = | = | = | ↑ | ↑ | ↑ | = | = |
| PRSW | = | ↓ | = | = | = | = | = | = | = | ↑↑ |
| Ees | = | ↓ | = | ↑ | = | ↑ | = | = | = | ↑↑ |
| dP/dt max | ↓ | ↓ | = | = | = | = | = | = | = | ↑↑ |
| dP/dt max_EDV | ↓ | ↓ | = | = | = | ↑ | = | = | = | = |
| dP/dt min | = | = | = | = | = | = | = | = | = | = |
| TAU | = | = | = | ↓ | = | ↑ | = | = | = | = |

SV: Stroke Volume;
CO: Cardiac Output;
SW: Stroke Work;
Ea: arterial Elastance;
ESP: End-Systolic Pressure;
EDP: End-Diastolic Pressure;
ESV: End-Systolic Volume;
PRSW: Preload Recruitable Stroke Work;
Ees: End-systolic Elastance;
dP/dt: peak rate of the pressure rise;
TAU: relaxation time constant calculated by Weiss method.

What is claimed is:

1. A method of promoting vasculogenesis in a subject, the method comprising administering a therapeutically effective amount of a GHRH agonist peptide to the subject, wherein the GHRH agonist peptide is P-27409 [N-Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$ or a pharmaceutically acceptable salt of the foregoing.

* * * * *

UNITED STATES PATENT AND TRADEMARK OFFICE
CERTIFICATE OF CORRECTION

| | |
|---|---|
| PATENT NO. | : 10,555,987 B2 |
| APPLICATION NO. | : 15/820079 |
| DATED | : February 11, 2020 |
| INVENTOR(S) | : Andrew Schally et al. |

It is certified that error appears in the above-identified patent and that said Letters Patent is hereby corrected as shown below:

In the Specification

The paragraph at Column 1, Lines 15-19, is replaced with the following:
--This invention was made with government support under HL 107110 awarded by National Institutes of Health and under BX005051 awarded by The Department of Veterans Affairs. The government has certain rights in the invention.--

Signed and Sealed this
Twelfth Day of July, 2022

Katherine Kelly Vidal
*Director of the United States Patent and Trademark Office*